(12) United States Patent
Gregory et al.

(10) Patent No.: US 9,834,787 B2
(45) Date of Patent: Dec. 5, 2017

(54) TARGETED INTEGRATION INTO STEM CELLS

(75) Inventors: Philip D. Gregory, Orinda (CA); Dirk Hockemeyer, Cambridge, MA (US); Michael C. Holmes, Oakland, CA (US); Rudolf Jaenisch, Cambridge, MA (US); Frank Soldner, Cambridge, MA (US); Fyodor Urnov, Point Richmond, CA (US); Shuyuan Yao, San Diego, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 398 days.

(21) Appl. No.: 12/798,749

(22) Filed: Apr. 8, 2010

(65) Prior Publication Data

US 2011/0027235 A1    Feb. 3, 2011

Related U.S. Application Data

(60) Provisional application No. 61/212,265, filed on Apr. 9, 2009, provisional application No. 61/269,432, filed on Jun. 24, 2009.

(51) Int. Cl.

| | |
|---|---|
| *C12P 21/02* | (2006.01) |
| *C12Q 1/02* | (2006.01) |
| *A61K 35/12* | (2015.01) |
| *C12N 5/10* | (2006.01) |
| *C12N 15/86* | (2006.01) |
| *C12N 9/22* | (2006.01) |

(52) U.S. Cl.
CPC ............... *C12N 15/86* (2013.01); *C12N 9/22* (2013.01); *C12N 2710/10343* (2013.01); *C12N 2740/15043* (2013.01); *C12N 2800/30* (2013.01); *C12N 2830/008* (2013.01)

(58) Field of Classification Search
CPC .... C12N 9/22; C12N 15/86; C12N 2830/008; C12N 2740/15043; C12N 2800/30; C12N 2710/10343
USPC ......... 424/93.7; 435/29, 325, 435, 366, 69.1
See application file for complete search history.

(56) References Cited

U.S. PATENT DOCUMENTS

| | | |
|---|---|---|
| 5,356,802 A | 10/1994 | Chandrasegaran |
| 5,420,032 A | 5/1995 | Marshall et al. |
| 5,436,150 A | 7/1995 | Chandrasegaran |
| 5,487,994 A | 1/1996 | Chandrasegaran |
| 5,639,618 A | 6/1997 | Gay |
| 5,789,538 A | 8/1998 | Rebar et al. |
| 5,925,523 A | 7/1999 | Dove et al. |
| 5,928,638 A | 7/1999 | Uchida et al. |
| 6,007,988 A | 12/1999 | Choo et al. |
| 6,013,453 A | 1/2000 | Choo et al. |
| 6,090,618 A | 7/2000 | Parmacek et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox et al. |
| 6,689,558 B2 | 2/2004 | Case |
| 6,824,978 B1 | 11/2004 | Cox et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,153,949 B2 | 12/2006 | Kim et al. |
| 7,163,824 B2 | 1/2007 | Cox et al. |
| 7,951,925 B2 * | 5/2011 | Ando et al. ................... 536/23.1 |
| 2002/0114788 A1 | 8/2002 | Isacson et al. |
| 2003/0003581 A1 * | 1/2003 | Economides et al. ........ 435/455 |
| 2003/0232410 A1 | 12/2003 | Liljedahl et al. |
| 2004/0096432 A1 * | 5/2004 | Fleischmann et al. .... 424/93.21 |
| 2004/0219563 A1 * | 11/2004 | West et al. ........................ 435/6 |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0188987 A1 | 8/2006 | Guschan et al. |
| 2006/0240556 A1 * | 10/2006 | Cibelli .......................... 435/440 |
| 2007/0134796 A1 | 6/2007 | Holmes et al. |
| 2007/0218528 A1 | 9/2007 | Miller et al. |
| 2008/0131962 A1 | 6/2008 | Miller |
| 2008/0159996 A1 | 7/2008 | Ando et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Faust et al., Blood, 96(2): 719-726, 2000.*
Gupta et al., Mol. And Cell. Biol., 18(12): 7243-4258, 1998.*
Takahashi et al., Cell, 131: 12-12, Nov. 30, 2007.*
Abuin et al., Molecular and Cellular Biology, 16(4): 1851-1856, 1996.*
Wu et al., Cell Molecular Life Sci., 64(200: 2933-2944, 2007.*
Davis et al., Nature Protocols, 3(10): 1550-1558, 2008.*
Qian et al., Stem Cells, 32(5): 1230-1238, 2014.*
DeKelver et al., Genome Research, 20: 1133-1142.*

(Continued)

*Primary Examiner* — Thaian N Ton
(74) *Attorney, Agent, or Firm* — Pasternak Patent Law; Susan Abrahamson

(57) ABSTRACT

Disclosed herein are methods and compositions for targeted integration of sequences of interest such as lineage-specific or cell fate reporter constructs or protein encoding sequences into stem cells.

7 Claims, 21 Drawing Sheets

(56) References Cited

U.S. PATENT DOCUMENTS

| | | | |
|---|---|---|---|
| 2008/0216185 | A1 | 9/2008 | Chesnut et al. |
| 2008/0299580 | A1 | 12/2008 | DeKelver et al. |
| 2009/0117617 | A1 | 5/2009 | Holmes et al. |
| 2009/0305419 | A1 | 12/2009 | Miller et al. |

FOREIGN PATENT DOCUMENTS

| | | | |
|---|---|---|---|
| WO | WO 96/06166 A1 | 2/1996 | |
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/60970 A2 | 8/2001 | |
| WO | WO 01/88197 A2 | 11/2001 | |
| WO | WO 02/16536 A1 | 2/2002 | |
| WO | 02/064748 A2 | 8/2002 | |
| WO | WO 02/077227 A2 | 10/2002 | |
| WO | WO 02/099084 A2 | 12/2002 | |
| WO | WO 03/016496 A2 | 2/2003 | |
| WO | 2006/076374 A1 | 7/2006 | |
| WO | 2006/127809 A2 | 11/2006 | |
| WO | WO 2007/014275 A2 | 1/2007 | |
| WO | WO 2008/089396 A1 | 7/2008 | |
| WO | WO 2008/126083 A2 | 10/2008 | |
| WO | WO 2008/133938 A2 | 11/2008 | |

OTHER PUBLICATIONS

Hockemeyer et al., Nature Biotechnology, 27(9): 851-857, Sep. 2009.*
Liu et al., PLoS One, 7(5): e37071, pp. 1-8, 2012.*
Argast, et al., "I-PPOI and I-CREI Homing Site Sequence Degeneracy Determined by Random Mutagenesis and Sequential in Vitro Enrichment," *J. Mol. Biol.* 280:345-353 (1998).
Ashworth, et al., "Computational Redesign of Endonuclease DNA Binding and Cleavage Specificity," *Nature* 441:656-659 (2006).
Beerli, et al., "Engineering Polydactyl Zinc-Finger Transcription Factors," *Nature Biotechnology* 20:135-141 (2002).
Belfort, et al., "Homing Endonucleases: Keeping the House in Order," *Nucleic Acids Research* 25:3379-3388 (1997).
Bitinate, et al., "Foki Dimerization Is Required for DNA Cleavage," *PNAS USA* 95:10570-10575 (1998).
Boch, et al., "Breaking the Code of DNA Binding Specificity of TAL-Type III Effectors," *Science* 326:1509-1512 (2009).
Brambrink et al., "Sequential Expression of Pluripotency Markers During Direct Reprogramming of Mouse Somatic Cells," *Cell Stem Cell* 2:151-159 (2008).
Chevalier, et al., "Design, Activity, and Structure of a Highly Specific Artificial Endonuclease," *Molecular Cell* 10:895-905 (2002).
Chisaka, et al., "Regionally Restricted Developmental Defects Resulting From Targeted Disruption of the Mouse Homeobox Gene HOX-1.5," *Nature* 350:473-479 (1991).
Choo, et al., "Advances in Zinc Finger Engineering," *Curr. Opin. Struct. Biol.* 10:411-416 (2000).
Creaser, et al., "Comparative and Functional Analysis of the AP2 Promoter Indicates That Conserved Octamer and Initiator Elements Are Critical for Activity," *Nucleic Acids Res* 24:2597-2606 (1996).
DePalma, et al., "Promoter Trapping Reveals Significant Differences in Integration Site Selection Between MLV and HIV Vectors in Primary Hematopoietic Cells," *Blood* 105:2307-2315 (2005).
Dimos, et al., "Induced Pluripotent Stem Cells Generated From Patients With ALS Can Be Differentiated Into Motor Neurons," *Science* 321:1218-1221 (2008).
Donovan, et al., "The End of the Beginning for Pluripotent Stem Cells," *Nature* 414:92-97 (2001).
Dujon, et al., "Mobile Introns: Definition of Terms and Recommended Nomenclature," *Gene* 82:115-118 (1989).

Eliopoulos, et al., "Bone Marrow-Derived Mesenchymal Stromal Cells (MSCS) as Efficient in Vivo Cellular Vehicles for Plasma Soluble Protein Delivery," *Blood Cells, Molecules and Diseases* 40:263-264 (2008).
Epinat, et al., "A Novel Engineered Meganuclease Induces Homologous Recombination in Yeast and Mammalian Cells," *Nucleic Acids Research* 31:2952-2962 (2003).
Gimble, et al., "Substrate Recognition and Induced DNA Distortion by the PI-SCEI Endonuclease, an Enzyme Generated by Protein Splicing," *J. Mol. Biol.* 263:163-180 (1996).
Hockemeyer, et al., "A Drug-Inducible System for Direct Reprogramming of Human Somatic Cells to Pluripotency," *Cell Stem Cell* 3:346-353 (2008).
Isalan et al., "A Rapid, Generally Applicable Method to Engineer Zinc Fingers Illustrated by Targeting the HIV-1 Promoter," *Nat Biotechnol* 19:656-660 (2001).
Isman, et al., "Adenovirus-Based Targeting in Myoblasts Is Hampered by Nonhomologous Vector Integration," *Human Gene Therapy* 19:1000-1008 (2008).
Jasin, et al., "Genetic Manipulation of Genomes With Rare-Cutting Endonucleases," *Trends Genet* 12:224-228 (1996).
Kim, et al., "Chimeric Restriction Endonuclease," *PNAS USA* 91:883-887 (1994).
Kim, et al., "Insertion and Deletion Mutants of FOKI Restriction Endonuclease," *J. Biol. Chem.* 269:31978-31981 (1994).
Levasseur, et al., "OCT4 Dependence of Chromatin Structure Within the Extended NANOG Locus in ES Cells," *Genes Dev* 22:575-580 (2008).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Lovell-Badge, et al., "The Future for Stem Cell Research," *Nature* 414:88-91 (2001).
Miller, et al., "An Improved Zinc-Finger Nuclease Architecture for Highly Specific Genome Editing," *Nature Biotech* 25:778-785 (2007).
Moscou, et al., "A Simple Cipher Governs DNA Recognition by TAL Effectors," *Science* 326:1501 (2009).
Nakagawa, et al., "Generation of Induced Pluripotent Stem Cells Without MYC From Mouse and Human Fibroblasts," *Nat Biotech* 26:101-106 (2008).
Pabo, et al., "Design and Selection of Novel CYS2—HIS2 Zinc Finger Proteins," *Ann. Rev. Biochem.* 70:313-340 (2001).
Paques, et al., "Meganucleases and DNA Double-Strand Break-Induced Recombination: Perspectives for Gene Therapy," *Current Gene Therapy* 7:49-66 (2007).
Pedersen, et al., "Studies of in Vitro Differentiation With Embryonic Stem Cells," *Reproduc Fertil Dev* 6:543-552 (1994).
Perez, et al., "Establishment of HIV-1 Resistance in CD4+ T Cells by Genome Editing Using Zinc-Finger Nucleases," *Nature Biotechnology* 26:808-816 (2008).
Perler, et al., "Protein Splicing Elements: Inteins and Exteins a Definition of Terms and Recommended Nomenclature," *Nucleic Acids Research* 22:1125-1127 (1994).
Porteus, et al., "Isolation and Characterization of a Novel CDNA Clone Encoding a Homeodomain That Is Developmentally Regulated in the Ventral Forebrain," *Neuron* 7:221-229 (1991).
Price, et al., "A Mouse Gene Related to Distal-Less Shows a Restricted Expression in the Developing Forebrain," *Nature* 351:748-751 (1991).
Robertson, "Derivation and Maintenance of Embryonic Stem Cell Cultures," *Meth Mol Biol* 75:173-184 (1997).
Roelink, et al., "Expression of Two Members of the WNT Family During Mouse Development-Restricted Temporal and Spatial Patterns in the Developing Neural Tube," *Genes Dev* 5:381-388 (1991).
Segal, et al., "Custom DNA-Binding Proteins Come of Age: Polydactyl Zinc-Finger Proteins," *Curr. Opin. Biotechnol.* 12:632-637 (2001).
Simeone, et al., "Two Vertebrate Homeobox Genes Related to the *Drosophila* Empty Spiracles Gene Are Expressed in the Embryonic Cerebral Cortex," *EMBO J* 11:2541-2550 (1992).

(56) References Cited

OTHER PUBLICATIONS

Smith, et al., "Robust, Persistent Transgene Expression in Human Embryonic Stem Cells Is Achieved With AAVS1-Targeted Integration," *Stem Cells* 26:496-506 (2008).

Soldner, et al., "Parkinson's Disease Patient-Derived Induced Pluripotent Stem Cells Free of Viral Reprogramming Factors," *Cell* 36:964-977 (2009).

Strathdee, et al., "Expression of Transgenes Targeted to the GT(ROSA)26SOR Locus Is Orientation Dependent," *Plos ONE* 1(e4):1-9 (2006).

Urnov, et al., "Highly Efficient Endogenous Human Gene Correction Using Designed Zinc-Finger Nucleases," *Nature* 435:646-651 (2005).

Bruce, S. J. et al., "In vitro differentiation of murine embryonic stem cells toward a real lineage", Differentiation, vol. 75, No. 5, Jun. 1, 2007 (Jun. 1, 2007), pp. 337-349.

Lombardo, et al., "Gene Editing in Human Stem Cells Using Zinc Finger Nucleases and Integrase-Defective Lentiviral Vector Delivery," Nature Biotechnology 25(11):1298-1306 (2007).

Porteus, et al., "Gene Targeting Using Zinc Finger Nucleases," Nature Biotechnology 23(8):967-973 (2005).

Moehle, et al., "Targeted Gene Addition Into a Specified Location in the Human Genome Using Designed Zinc Finger Nucleases," *PNAS USA* 104(9):3055-3060 (2007).

Zhao, et al., "Generation of Embryonic Stem Cells and Transgenic Mice Expressing Green Fluorescence Protein in Midbrain Dopaminergic Neurons," European Journal of Neuroscience, vol. 19, pp. 1133-1140 (2004).

\* cited by examiner

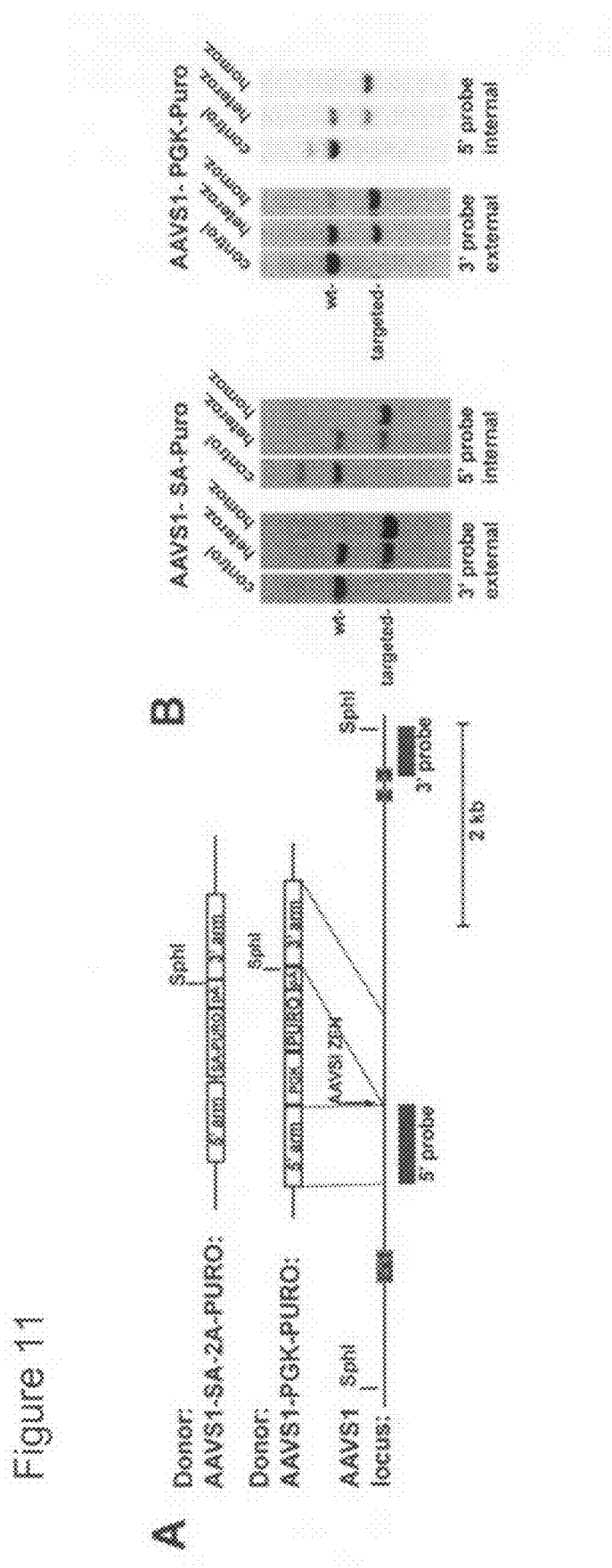

SEQUENCE LISTING

<160> NUMBER OF SEQ ID NOS: 63

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Gly Asp Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ser Ser Asp Leu Arg Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Arg Gly Thr Leu Ala Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Asp His Leu Thr Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Ser Ala Leu Ser Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic

```
                    peptide

<400> SEQUENCE: 6

Arg Ser Asp Asn Leu Arg Glu
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Arg Ser His Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ser Gly His Leu Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Ala Asn Leu Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Val Leu Ser Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Gly His Leu Ser Arg
1               5

<210> SEQ ID NO 12
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Ser Asp Leu Ser Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Ser Asp Leu Ser Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Ala Asp Arg Thr Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Ala His Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp Asn Leu Ser Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Arg Ser Ala Asn Leu Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Asp Ala Leu Ala Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly Asn Leu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ser Asp Ala Leu Ser Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Arg Ser Asp Arg Thr Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Ser Asp His Leu Thr Asn
1               5

<210> SEQ ID NO 23
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 23

Asp Arg Ala Asn Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Asp Asn Leu Ser Val
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Asn Ala Thr Arg Ile Asn
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Gly Ser Leu Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp His Leu Ser Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Arg Ser Asn Arg Lys Thr
1               5

```
<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Ala Ala Leu Ser Arg
1               5

<210> SEQ ID NO 30
<211> LENGTH: 28
<212> TYPE: DNA
<213> ORGANISM: Homo sapiens

<400> SEQUENCE: 30
gccaggtctg ggcagctgca ggtgacca                                          28

<210> SEQ ID NO 31
<211> LENGTH: 28
<212> TYPE: DNA
<213> ORGANISM: Homo sapiens

<400> SEQUENCE: 31
cccaggagag gagcaggcag ggtcagct                                          28

<210> SEQ ID NO 32
<211> LENGTH: 28
<212> TYPE: DNA
<213> ORGANISM: Homo sapiens

<400> SEQUENCE: 32
tcctgggtgc caggtctggg cagctgca                                          28

<210> SEQ ID NO 33
<211> LENGTH: 28
<212> TYPE: DNA
<213> ORGANISM: Homo sapiens

<400> SEQUENCE: 33
aggagcaggc agggtcagct gccctggc                                          28

<210> SEQ ID NO 34
<211> LENGTH: 28
<212> TYPE: DNA
<213> ORGANISM: Homo sapiens

<400> SEQUENCE: 34
aagctggtct ggtggctagg tagatcct                                          28

<210> SEQ ID NO 35
<211> LENGTH: 28
<212> TYPE: DNA
<213> ORGANISM: Homo sapiens

<400> SEQUENCE: 35
gggctctgga aggcccactt cagggcct                                          28

<210> SEQ ID NO 36
<211> LENGTH: 28
<212> TYPE: DNA
<213> ORGANISM: Homo sapiens
```

```
<400> SEQUENCE: 36
atgtaacaaa ggactactct tcccccag                                          28

<210> SEQ ID NO 37
<211> LENGTH: 28
<212> TYPE: DNA
<213> ORGANISM: Homo sapiens

<400> SEQUENCE: 37
atgagtcagt gaacagggaa tgggtgaa                                          28

<210> SEQ ID NO 38

<400> SEQUENCE: 38

000

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Asp His Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ser Ala Thr Arg Thr Asn
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp His Leu Ser Gln
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Asp Val Arg Lys Asn
1               5

<210> SEQ ID NO 43
```

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ser Asp Ala Leu Ser Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp Ala Leu Thr Gln
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Asn Asp Asp Arg Lys Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Ala Thr Arg Thr Lys
1               5

<210> SEQ ID NO 47
<211> LENGTH: 28
<212> TYPE: DNA
<213> ORGANISM: Homo sapiens

<400> SEQUENCE: 47
gtgctctggg agctgggggt gcggagtg                                    28

<210> SEQ ID NO 48
<211> LENGTH: 28
<212> TYPE: DNA
<213> ORGANISM: Homo sapiens

<400> SEQUENCE: 48
ctgcaagggc caggagcaca gcggtaag                                    28

<210> SEQ ID NO 49
<211> LENGTH: 28
<212> TYPE: DNA
<213> ORGANISM: Homo sapiens

```
<400> SEQUENCE: 49
gtctgggggc cagggtgggg gcaggtca                                              28

<210> SEQ ID NO 50
<211> LENGTH: 28
<212> TYPE: DNA
<213> ORGANISM: Homo sapiens

<400> SEQUENCE: 50
cagaaaaggc ctcggcttcg ctgcccgg                                              28

<210> SEQ ID NO 51
<211> LENGTH: 28
<212> TYPE: DNA
<213> ORGANISM: Homo sapiens

<400> SEQUENCE: 51
tgacacagta cctggcacca tagttgta                                              28

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Asp Val Leu Ser Ala
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Ser Asn Arg Ile Lys
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Asp His Leu Ser Glu
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Ser Ala Ser Arg Lys Asn
```

<210> SEQ ID NO 56
<211> LENGTH: 28
<212> TYPE: DNA
<213> ORGANISM: Homo sapiens

<400> SEQUENCE: 56
gtactagggg tatggggata aaccagac                                            28

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Asp Ser Leu Ser Val
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ser Ser Thr Arg Ile Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Ala Ser Thr Arg His Cys
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Lys Ser Thr Leu His Ala
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

-continued

```
Asp Asn Ala Asn Arg Thr Lys
1               5

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gctagcgata tcgtcgacca tatgggatcc                                     30

<210> SEQ ID NO 63
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cagacctggc acccaggaga ggagcaggca gggtcagct                            39
```

TARGETED INTEGRATION INTO STEM CELLS

CROSS-REFERENCE TO RELATED APPLICATIONS

The present application claims the benefit of U.S. Provisional Application No. 61/212,265, filed Apr. 9, 2009 and U.S. Provisional Application No. 61/269,432, filed Jun. 24, 2009, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the fields of genome modification of stem cells and uses thereof.

BACKGROUND

Stem cells are undifferentiated cells that exist in many tissues of embryos and adult mammals. Both adult and embryonic stem cells are able to differentiate into a variety of cell types and, accordingly, may be a source of replacement cells and tissues that are damaged in the course of disease, infection, or because of congenital abnormalities. (See, e.g., Lovell-Badge (2001) *Nature* 414:88-91; Donovan et al. (2001) *Nature* 414:92-97). Various types of putative stem cells exist which; when they differentiate into mature cells, carry out the unique functions of particular tissues, such as the heart, the liver, or the brain. Pluripotent stem cells are thought to have the potential to differentiate into almost any cell type, while multipotent stem cells are believed to have the potential to differentiate into many cell types (Robertson (1997) *Meth. Cell Biol.* 75:173; and Pedersen (1994) *Reprod. Fertil. Dev.* 6:543). For example, human induced pluripotent stem cells (hiPSCs) are pluripotent cells derived from somatic cells by the ectopic expression of reprogramming factors (see for example Nakagawa et al, (2008) *Nat. Biotechnol* 26:101-106). These cells share all the key characteristics of human embryonic stem cells (hESC) and can be generated from cells isolated from human patients with specific diseases (see for example Dimos et al, (2008) *Science* 321:1218-1221).

Stable transgenesis and targeted gene insertion into stem cells have a variety of applications. Stably transfected stem cells can be used as a cellular vehicle for protein-supplement gene therapy and/or to direct the stem cells into particular lineages. See, e.g., Eliopoulos et al. (2008) *Blood Cells, Molecules, and Diseases* 40(2):263-264. In addition, insertion of lineage-specific reporter constructs would allow isolation of lineage-specific cells, and would allow drug discovery, target validation, and/or stem cell based studies of gene function and the like based upon those results. For example, U.S. Pat. No. 5,639,618 describes in vitro isolation of a lineage-specific stem cell by transfecting a pluripotent embryonic stem cell with a construct comprising a regulatory region of a lineage-specific gene operably linked to a DNA. However, current strategies of stem cell transfection often randomly insert the sequence of interest (reporter) into the stem cell. See, e.g., Islan et al. (2008) *Hum Gene Ther* October; 19(10):1000-1008; DePalma et al. (2005) *Blood* 105(6):2307-2315. The inability to control the location of genome insertion can lead to highly variable levels of expression throughout the stem cell population due to position effects within the genome.

Additionally, current methods of stable transgenesis and amplification of transgenes often result in physical loss of the transgene, transgene silencing over time or upon stem cell differentiation, insertional mutagenesis by the integration of a transgene and autonomous promoter inside or adjacent to an endogenous gene, the aberrant expression of endogenous genes caused by the heterologous regulatory elements associated with the randomly integrating transgene, the creation of chromosomal abnormalities and expression of rearranged gene products (comprised of endogenous genes, the inserted transgene, or both), and/or the creation of vector-related toxicities or immunogenicity in vivo from vector-derived genes that are expressed permanently due to the need for long-term persistence of the vector to provide stable transgene expression. Furthermore, the correct expression pattern of a given endogenous gene such as a gene that is a lineage marker emerges out of the combined action of a large number of cis-regulatory elements. See, e.g. Levasseur et al (2008) *Genes Dev.* 22: 575-580.

Zinc finger nucleases can be used to efficiently drive targeted gene insertion at extremely high efficiencies using a homologous donor template to insert novel gene sequences via homology-driven repair (HDR). See, for example, United States Patent Publications 20030232410; 20050208489; 20050026157; 20050064474; and 20060188987, and International Publication WO 2007/014275, the disclosures of which are incorporated by reference in their entireties for all purposes. Zinc finger nuclease-driven gene insertion can use the transient delivery of a non-integrating vector, and this does not require long-term persistence of the delivery vector, avoiding issues of insertional mutagenesis and toxicities or immunogenicity from vector-derived genes.

However, there remains a need for controlled, site-specific integration into a stem cell population.

SUMMARY

Disclosed herein are compositions and methods for targeted integration of one or more sequences of interest into the genome of a stem cell. Sequences inserted into the stem cells may include protein encoding sequences, and/or lineage-specific reporter constructs, insertion of reporter genes for other endogenous genes of interest, reporters for endogenous genes involved in cell fate determination, and non-protein-coding sequences such as micro RNAs (miRNAs), shRNAs, RNAis and promoter and regulatory sequences. Reporter constructs may result in constitutive, inducible or tissue-specific expression of a gene of interest. Stem cells labeled with lineage-specific reporters can be used for various differentiation studies, and also for purification of differentiated cells of a selected lineage-specific (or mature) cell type. Stem cells marked with lineage-specific reporters can be used to screen for compounds such as nucleic acids, small molecules, biologics such as antibodies or cytokines, and/or in vitro methods that can drive a population of stem cells down a particular lineage pathway of interest towards a lineage-specific cell type. Stem cells comprising lineage-specific reporters can also be used as a tracking system to follow the in vivo position and ultimately the final location, differentiation fate, and mechanism of action (e.g. integration into tissues) of the stem cells following introduction into a subject. Stem cells may contain suicide cassettes comprising inserted sequences encoding certain reporter proteins (e.g., HTK). In some embodiments, suicide cassettes are used to facilitate the identification and isolation of a specific type of differentiated subpopulation of cells from a larger cell population. In other embodiments, suicide cassettes are used to destroy stem cells which have differentiated into any undesirable state in vivo, for example if the cells differentiated and formed a teratoma. Likewise, stem cells expressing one or more polypeptides can be used as cellular vehicles for protein-supplement gene therapy. In contrast to traditional integration methods in which a construct is randomly integrated into the host cell genome, integration of constructs as described herein to a specified site allows, in the case of e.g., lineage-specific reporter constructs, correct expression only upon differentiation into the cognate mature cell type, and in the case of protein expression constructs, uniform expression between cells of the population.

Patient derived hiPSCs from patients with specific diseases can also be used to establish in vitro and in vivo models for human diseases. Genetically modified hESCs and hiPSCs could be used to improve differentiation paradigms, to overexpress disease related genes, and to study disease pathways by loss of function experiments. Importantly, studies can be carried out within the context of the appropriate genetic or mutant background as that found in the patient population.

Thus, in one aspect, provided herein is a stem cell (or population of stem cells) comprising an exogenous sequence (e.g. a transgene) integrated into a selected region of the stem cell's genome. In certain embodiments, the transgene comprises a lineage-specific promoter and/or a gene product (e.g., protein coding sequence, non-protein coding sequence such as transcribed RNA products including micro RNAs (miRNAs), shRNAs, RNAis and combinations thereof) and, when integrated into the selected region of the stem cell is transcribed or translated upon initiation of, or during a differentiation pathway and/or upon differentiation of the stem cell into a lineage-specific or mature cell type. The gene product may be expressed only during the differentiation pathway into a particular cell type. In addition, the gene product may be expressed in one, some or all of the cell types into which the stem cell is capable of differentiating. In certain embodiments, the gene product is a lineage-specific or cell-fate gene, for example a promoterless gene that is integrated into a selected locus such that its expression is driven by the regulatory control elements (e.g., promoter) present in the endogenous locus into which the gene is integrated. The stem cell may be a mammalian stem cell, for example, a hematopoietic stem cell, a mesenchymal stem cell, an embryonic stem cell, a neuronal stem cell, a muscle stem cell, a liver stem cell, a skin stem cell, an embryonic stem cell, an induced pluripotent stem cell and combinations thereof. In certain embodiments, the stem cell is a human induced pluripotent stem cells (hiPSC). The gene product may be expressed constitutively, inducibley or tissue-specifically.

In certain embodiments, the gene product is a promoterless reporter gene that is integrated into a lineage-specific or cell fate gene such that the expression of the reporter is driven by the regulatory elements of the lineage-specific or cell fate gene.

In any of the stem cells described herein, the transgene may be flanked by recombination sites and/or may be a suicide cassette.

In certain embodiments, the stem cells described herein comprise two reporters linked to two endogenous gene promoter sequences. In certain embodiments, one reporter may be used to isolate or exclude cells heading towards a particular differentiation lineage or fate. For example, a reporter that reports on whether a cell has committed to an undesired cell lineage or fate could be used to exclude those cells from a pool of cells otherwise differentiating towards a desired lineage or fate. The second reporter (marker) may be linked to an endogenous gene known to be expressed in the desired lineage-specific or mature cell type.

Doubly tagged stem cells are useful in studying complicated processes such as the development of a cancer stem cell from a differentiated cell population. In certain embodiments, doubly tagged differentiated cells are isolated from a stem cell population using a reporter gene linked to a lineage-specific or cell fate reporter, as described previously, and comprising the second reporter linked to an endogenous gene involved in de-differentiation are used to determine what external or internal conditions cause a cell to de-differentiate, potentially into a cancer stem cell.

Doubly tagged differentiated cell populations isolated using a reporter of lineage or cell fate as described previously are used with a second suicide marker linked to an endogenous gene involved in de-differentiation such that if the cells begin to revert to a potentially troublesome stem cell-like state, the de-differentiation would induce expression of the suicide gene and lead to the killing of these de-differentiating cells only. This embodiment could potentially address safety concerns regarding the use of stem cells in vivo as therapeutics.

In addition, insertion of wild type copies of genes into stem cells derived from donors with a mutant endogenous gene also allows for various therapies. For example, in hemophilia B, patients suffer from the lack of a competent Factor IX protein. Factor IX encodes one of the serine proteases involved with the coagulation system, and it has been shown that restoration of even 3% of normal circulating levels of wild type Factor IX protein can prevent spontaneous bleeding.

Thus, the present disclosure provides methods and compositions for integrating a sequence (e.g., a lineage-specific or cell fate reporter construct or polypeptide encoding sequence) into a stem cell, for example a human, mouse, rabbit, pig or rat cell. Targeted integration of the construct is facilitated by targeted double-strand cleavage of the genome in the region of interest. Cleavage is targeted to a particular site through the use of fusion proteins comprising a zinc finger DNA binding domain, which can be engineered to bind any sequence of choice in the region of interest, and a cleavage domain or a cleavage half-domain. Such cleavage stimulates targeted integration of exogenous polynucleotide sequences at or near the cleavage site. In embodiments in which a lineage-specific or cell fate reporter construct is integrated into a stem cell, the reporter construct typically, but not necessarily comprises a promoter from a gene expressed during differentiation operably linked to a promoterless polynucleotide encoding a reporter sequence.

In one aspect, provided herein is a method for targeted integration of a lineage-specific reporter construct into a stem cell, the method comprising: (a) expressing a first fusion protein in the cell, the first fusion protein comprising a first zinc finger binding domain and a first cleavage half-domain, wherein the first zinc finger DNA binding domain has been engineered to bind to a first target site in a region of interest in the genome of the cell; (b) expressing a second fusion protein in the cell, the second fusion protein comprising a second zinc finger DNA binding domain and a second cleavage half domain, wherein the second zinc finger DNA binding domain binds to a second target site in the region of interest in the genome of the cell, wherein the second target site is different from the first target site; and (c) contacting the cell with a lineage-specific or cell fate reporter construct as described herein; wherein binding of the first fusion protein to the first target site, and binding of the second fusion protein to the second target site, positions the cleavage half-domains such that the genome of the cell is cleaved in the region of interest, thereby resulting in integration of the lineage-specific or cell fate reporter construct into the genome of the cell in the region of interest.

In another aspect, provided herein is a method for targeted integration of a coding sequence into a stem cell, the method comprising: (a) expressing a first fusion protein in the cell, the first fusion protein comprising a first zinc finger DNA binding domain and a first cleavage half-domain, wherein the first zinc finger DNA binding domain has been engineered to bind to a first target site in a region of interest in the genome of the cell; (b) expressing a second fusion protein in the cell, the second fusion protein comprising a second zinc finger DNA binding domain and a second cleavage half domain, wherein the second zinc finger DNA binding domain binds to a second target site in the region of interest in the genome of the cell, wherein the second target site is different from the first target site; and (c) contacting the cell with a coding sequence; wherein binding of the first fusion protein to the first target site, and binding of the second fusion protein to the second target site, positions the cleavage half-domains such that the genome of the cell is cleaved in the region of interest thereby resulting in integration of the coding sequence into the genome of the cell in the regions of interest. In certain embodiments, the coding sequence comprises a sequence encoding a therapeutic protein, a reporter gene or a positive or negative screening marker gene.

In another aspect, provided herein is a method for targeted integration of two or more gene products into a stem cell (e.g. protein coding sequences, non-protein coding sequences such as transcribed RNA products including micro RNAs (miRNAs), shRNAs, RNAis, lineage-specific or cell fate reporter sequences, or any combination thereof, the method comprising: (a) expressing a first fusion protein in the cell, the first fusion protein comprising a first zinc finger DNA binding domain and a first cleavage half-domain, wherein the first zinc finger DNA binding domain has been engineered to bind to a first target site in a region of interest in the genome of the cell; (b) expressing a second fusion protein in the cell, the second fusion protein comprising a second zinc finger DNA binding domain and a second cleavage half domain, wherein the second zinc finger DNA binding domain binds to a second target site in the region of interest in the genome of the cell, wherein the second target site is different from the first target site; and (c) expressing a third fusion protein in the cell, the third fusion protein comprising a third zinc finger DNA binding domain and a third cleavage half-domain, wherein the third zinc finger DNA binding domain has been engineered to bind to a third target site in a region of interest in the genome of the cell; wherein the third target site is different from the first and second, (d) expressing a fourth fusion protein in the cell, the fourth fusion protein comprising a fourth zinc finger DNA binding domain and a fourth cleavage half domain, wherein the fourth zinc finger DNA binding domain binds to a fourth target site in the region of interest in the genome of the cell, wherein the fourth target site is different from the first, second and third target sites; and (e) contacting the cell with two coding sequences or lineage-specific or cell fate reporter sequences, or any combination thereof; wherein binding of the first fusion protein to the first target site, and binding of the second fusion protein to the second target site, positions the cleavage half-domains such that the genome of the cell is cleaved in the first region of interest, thereby resulting in integration of the coding or lineage-specific or cell fate reporter sequence into the genome of the cell in the region of interest, and wherein binding of the third fusion protein to the third target site, and binding of the fourth fusion protein to the fourth target site, positions the cleavage half-domains such that the genome of the cell is cleaved in the second region of interest, thereby resulting in integration of the two coding or lineage-specific or cell fate reporter sequences into the genome of the cell in the regions of interest. In certain embodiments, the coding sequences comprise a sequence encoding a therapeutic protein, a reporter gene or a positive or negative screening marker gene.

In another aspect, described herein is a method of isolating cells of a selected cell type (cells in a differentiation pathway, lineage-specific cells or mature cells), the method comprising culturing a population of stem cells as described herein (e.g., containing a lineage-specific or cell fate promoter and/or lineage-specific or cell fate gene inserted through targeted integration and expressed in a selected lineage-specific or mature cell type) and isolating the cells that express the gene product, thereby isolating cells of the selected lineage-specific or mature cell type.

In yet another aspect, described herein is a method of determining the effect of a compound, nucleic acid or biologic on stem cell differentiation, the method comprising culturing a first population of stem cells comprising a lineage-specific or cell fate reporter sequence as described herein in the presence of the compound, nucleic acid or biologic, culturing a second population of the same stem cells comprising a lineage-specific or cell fate reporter sequence as the first population of stem cells in the absence of the compound, nucleic acid or biologic and evaluating expression of the gene product in the first and second populations. A difference in the expression of the gene product in the presence of the compound, nucleic acid or biologic indicates an effect of the compound, nucleic acid or biologic on stem cell differentiation.

In another aspect, described herein is a method of producing a gene product in a stem cell, the method comprising providing a population of stem cells as described herein comprising a sequence that is transcribed or translated into the gene product, wherein the sequence is integrated into a non-essential site in the stem cells, and culturing the population of stem cells, wherein the population of cultured stem cells uniformly expresses the gene product.

In another aspect, provided herein is a method of treating a disease characterized by reduced expression of a functional gene product in a subject in need of treatment, the method comprising: administering a population of stem cells as described herein that express the functional gene product. In certain embodiments, the functional gene product is Factor IX and the disease is hemophilia.

In any of the methods and compositions described herein, the inserted sequence(s) (e.g., lineage-specific or cell fate reporter construct, coding sequence, etc.) and/or zinc finger nuclease can be provided in any vector, for example, a plasmid, as linear DNA, an adenovirus vector or a retroviral vector. In certain embodiments, the sequence to be inserted and zinc finger nuclease-encoding sequences are provided on the same vector. In other embodiments, the sequence to be integrated (e.g. reporter construct) is provided on an integration deficient lentiviral vector (IDLY) and one or both of the fusion proteins comprising the first and second zinc finger proteins are provided on an adenovirus (Ad) vector, for example an Ad5/F35 vector. In certain embodiments, the zinc finger nuclease encoding sequences are supplied as mRNA. In any methods and compositions described herein, the inserted sequence can be a sequence which corrects a deficiency in a stem cell and/or deficiency in a patient. In some embodiments, the inserted sequence can be a nucleotide sequence encoding a wild type Factor IX protein.

In some embodiments, the methods and compositions described herein can be used to modify both alleles of a cell with two different donors. For example, modification of a safe harbor gene (for example, AAVS1, also known as PPP1R12C) with a regulatable gene expression construct (for example, an expression construct built to be responsive to doxycyclin (DOX)) on one allele may be paired in a cell with an AAVS1 gene that has been simultaneously modified with the regulated promoter's transactivator (for example M2rtTA) on the homologous allele. This would eliminate positional variation effects of the expression of the inserted transgenes.

In any of the embodiments described herein, the reporter gene of the construct may comprise for example, chloramphenicol acetyl transferase (CAT), Red fluorescent protein (RFP), GFP, luciferase, thymidine kinase and/or β-galactosidase. Further, the control element (e.g., promoter) driving expression of the reporter gene can be isolated from any gene that is expressed during differentiation of a stem cell. Use of such reporter systems can be for gaining mechanistic insight into the process of in vitro reprogramming of cells. In certain embodiments, the control element is derived from an adipose specific marker gene, for example ap2. In some embodiments, the reporter gene expression construct may be flanked by sequences such as lox or FRT allowing for its subsequent removal through transient expression of specific recombinases such as Cre and FLP. These recombinase removal systems may be used to remove any other donor sequences as desired. Likewise, any coding sequence can be targeted to a particular region of the genome of a stem cell. In certain embodiments, the coding sequence comprises a plasma-soluble protein such as erythropoietin (EPO), FIX, VEGF, immunoglobulins, soluble cell surface receptors, soluble intercellular adhesion molecules, P-selectin and the like. In some embodiments, the soluble proteins may be of therapeutic value.

The methods and compositions as described herein find use in any adult or fetal (embryonic) stem cell, including but not limited to hematopoietic stem cells, mesenchymal stem cells, neural, muscle, liver or skin stem cells, embryonic stem cells, induced pluripotent stem cells and the like. In certain embodiments, the stem cell is a mammalian stem cell, for example a mouse, rat, rabbit, pig or human stem cell.

BRIEF DESCRIPTION OF THE DRAWINGS

FIG. 2B shows control amplification of the GAPDH locus to normalize for DNA input levels.

FIG. 6A shows GFP expression in Jurkat cells (left side) and K562 cells (right side). FIG. 6B shows GFP expression in human mesenchymal stem cells (hMSCs).

FIG. 10, panels A to C, show targeting of the OCT4 locus. FIG. 10A discloses SEQ ID NO: 63. Probes used for Southern blot analysis are shown as red boxes, exons of the OCT4 locus are shown as blue boxes and arrows indicate the genomic site cut by the respective ZFN pair. Donor plasmids used to target the OCT4 locus are shown above; SA-GFP: splice acceptor eGFP sequence, 2A: self-cleaving 2A peptide sequence, PURO: puromycin resistance gene, polyA: polyadenylation sequence. Inset in the upper left depicts a cartoon of two ZFNs binding at a specific genomic site (yellow) leading to the dimerization of the FokI nuclease domains.

FIG. 11, panels A and B, depict a targeting strategy for PPP gene. FIG. 11A depicts a schematic overview of the targeting strategy for the PPP1R12C gene in the AAV locus. Probes used for Southern blot analysis are shown as red boxes, the first 3 exons of PPP1R12C gene are shown as blue boxes and arrows indicate the genomic site cut by the ZFN. Donor plasmids used to target the locus are shown above; SA-Puro: splice acceptor sequence followed by a 2A self-cleaving peptide sequence and the puromycin resistance gene, pA: polyadenylation sequence, PGK: human phosphoglycerol kinase promoter, Puro: puromycin resistance gene. FIG. 11B shows southern blot analysis of BGO1 cells targeted with the indicated donor plasmids using the AAVS1 ZFNs. Genomic DNA was digested with SphI and hybridized with a $^{32}$P-labeled external 3'-probe or with the internal 5'-probe. Fragment sizes are: PGK-Puro: 5' probe: wt=6.5 kb, targeted=4.2 kb; 3' probe: wt=6.5 kb, targeted=3.7 kb. SA-Puro: 5' probe: wt=6.5 kb, targeted=3.8 kb; 3' probe: wt=6.5 kb, targeted=3.7 kb.

In FIG. 18A, DNA was isolated from cells 3 days following transfection. Lane 1 contains PCR products isolated from K562 cells that were transfected with only donor DNA in the absence of Factor-IX-specific ZFNs which had been digested with NheI. In lanes 2-5, Factor-IX specific ZFNs containing a wildtype Fok1 dimerization domain were used with increasing amounts of donor plasmid. In lanes 6-9, Factor-IX specific ZFNs containing the ELD/KKK Fok1 dimerization domain were used with increasing amounts of donor plasmid. The percentage of NheI sensitive DNA is indicated below each lane. FIG. 18B depicts similar results 10 days after transfection.

DETAILED DESCRIPTION

Figure 1:
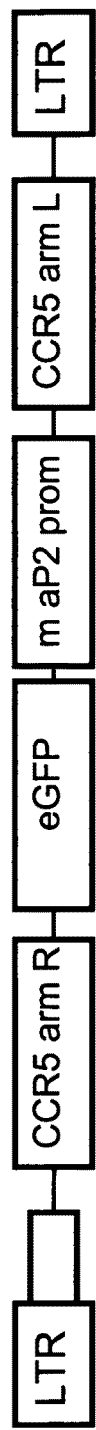
FIG. 1 is a schematic depicting an integration defective lentiviral vector (IDLY) containing homology arms to CCR5 flanking a reporter cassette in which the aP2 promoter/enhancer sequence drives expression of GFP.

Described herein are compositions and methods for targeted integration of a sequence of interest (e.g. a lineage-specific reporter construct and/or a coding sequence) into stem cells.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (IQ) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains, for example the recognition helix of a zinc finger, can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970; WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. Suitable programs for calculating the percent identity or similarity between sequences are generally known in the art, for example, another alignment program is BLAST, used with default parameters. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detectian of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474; 2007/0218528 and 2008/0131962, incorporated herein by reference in their entireties.

A "conditional mutation" is a mutation that has a wild-type phenotype under certain environmental conditions (known as "permissive") and a mutant phenotype under certain "restrictive" conditions. Conditional mutations may be cold sensitive, where the mutation results in an altered phenotype at cooler temperatures, but upon exposure to warmer temperatures, the phenotype returns more or less to wild-type. Conversely, conditional mutations may be heat sensitive (often termed "thermal sensitive") where the wild type phenotype is seen at cooler temperatures but becomes altered upon exposure to warmer temperatures. "Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids, include DNA and RNA, can be single or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases. An exogenous molecule can also be the same type of molecule as an endogenous molecule but derived from a different species than the cell is derived from. For example, a human nucleic acid sequenced may be introduced into a cell line originally derived from a mouse or hamster.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also refer to a nucleic acid from a different species, for example, a human gene inserted into a hamster genome.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Lineage-specific" genes are those wherein their expression is the hallmark of a particular cell type such as a differentiated cell or a cell undergoing the process of differentiation into a lineage-specific cell type or a mature cell type.

"Cell fate" genes are those that are involved in determining or driving the designation of a cell to a particular function and/or a lineage-specific or mature cell type.

A "differentiation pathway" is a pathway followed by a stem cell as it heads towards a lineage-specific or mature cell type and so begins with a stem cell and ends with a lineage-specific or mature, differentiated cell. A stem cell following such a pathway can go through many stages. For example, a stem cell differentiating into a mature B cell or T cell must first differentiate into a lymphoid precursor cell. The lymphoid precursor cell then enters into either the pathway towards becoming a mature B cell or a mature T cell.

A "suicide gene" is a gene that when expressed, causes death of the cell in which it is expressed. Suicide genes may encode enzymes (for example, cytosine deaminase) that act upon prodrug small molecules (5-flurocytosine in the case of cytosine deaminase) and convert them into cytotoxic compounds (5-flurouracil) within the cell, or they may encode enzymes such as Herpes simplex virus thymidine kinase (HSV-TK or HTK) or Varicella zoster thymidine kinase (VSV-tk) that cause a cell to become sensitized to a specific compound, such as Ganciclovir. Suicide genes also include those which when expressed, induce the cell to become apoptotic, necrotic or otherwise lose viability. Examples include pro-apoptotic receptor agonists (for example, tumor necrosis factor-related apoptosis-inducing ligand (TRAIL)), that when stimulated, cause the initiation of apoptosis.

"Gene expression" refers to the conversion of the information, contained in a gene, into a gene product. A gene product can be the direct transcriptional product of a gene (e.g., mRNA, tRNA, rRNA, antisense RNA, shRNAs, micro RNAs (miRNAs) ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be complete (knockout) or partial (e.g., a hypomorph in which a gene exhibits less than normal expression levels or a product of a mutant gene that shows partial reduction in the activity it influences).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A "safe harbor" locus is a locus within the genome wherein a gene may be inserted without any deleterious affects on the host cell. Most beneficial is a safe harbor locus in which expression of the inserted gene sequence is not perturbed by any read-through expression from neighboring genes. Examples of safe harbor loci in mammalian cells are the AAVS1 gene (see U.S. Publication No. 20080299580) or the CCR5 gene (see U.S. publication 20080159996).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

Typical "control elements" include, but are not limited to transcription promoters, transcription enhancer elements, cis-acting transcription regulating elements (transcription regulators, a cis-acting element that affects the transcription of a gene, for example, a region of a promoter with which a transcription factor interacts to modulate expression of a gene), transcription termination signals, as well as polyadenylation sequences (located 5' to the translation stop codon), sequences for optimization of initiation of translation (located 5' to the coding sequence), translation enhancing sequences, and translation termination sequences. Control elements are derived from any include functional fragments thereof, for example, polynucleotides between about 5 and about 50 nucleotides in length (or any integer therebetween); preferably between about 5 and about 25 nucleotides (or any integer therebetween), even more preferably between about 5 and about 10 nucleotides (or any integer therebetween), and most preferably 9-10 nucleotides. Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "reporter gene" or "reporter sequence" refers to any sequence that produces a protein product that is easily measured, preferably in a routine assay. Suitable reporter genes include, but are not limited to, Mel1, chloramphenicol acetyl transferase (CAT), light generating proteins such as GFP, luciferase and/or β-galactosidase. Suitable reporter genes may also encode markers or enzymes that can be measured in vivo such as thymidine kinase, measured in vivo using PET scanning, or luciferase, measured in vivo via whole body luminometric imaging. Selectable markers can also be used instead of, or in addition to, reporters. Positive selection markers are those polynucleotides that encode a product that enables only cells that carry and express the gene to survive and/or grow under certain conditions. For example, cells that express neomycin resistance (Ned) gene are resistant to the compound G418, while cells that do not express Ned are skilled by G418. Other examples of positive selection markers including hygromycin resistance and the like will be known to those of skill in the art. Negative selection markers are those polynucleotides that encode a product that enables only cells that carry and express the gene to be killed under certain conditions. For example, cells that express thymidine kinase (e.g., herpes simplex virus thymidine kinase, HSV-TK) are killed when gancyclovir is added. Other negative selection markers are known to those skilled in the art. The selectable marker need not be a transgene and, additionally, reporters and selectable markers can be used in various combinations.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Inserted Sequences

Described herein are methods of targeted insertion of any sequence of interest into a stem cell. Sequences to be inserted include lineage-specific or cell fate reporter gene expression cassettes comprising control elements selected from a gene or groups of genes whose expression is known to be associated with a particular differentiation lineage of a stem cell. Sequences comprising genes involved in cell fate or other markers of stem cell differentiation can also be inserted. For example a promoterless construct containing such a gene can be inserted into a specified region (locus) such that the endogenous promoter at that locus drives expression of the gene product.

A significant number of genes and their control elements (promoters and enhancers) are known which direct the developmental and lineage-specific expression of endogenous genes. Accordingly, the selection of control element (s) and/or gene products inserted into stem cells will depend on what lineage and what stage of development is of interest. In addition, as more detail is understood on the finer mechanistic distinctions of lineage-specific expression and stem cell differentiation, it can be incorporated into the experimental protocol to fully optimize the system for the efficient isolation of a broad range of desired stem cells.

Any lineage-specific or cell fate regulatory element (e.g. promoter) or cell marker gene can be used in the compositions and methods described herein. Lineage-specific and cell fate genes or markers are well-known to those skilled in the art and can readily be selected to evaluate a particular lineage of interest. Non-limiting examples of include, but not limited to, regulatory elements obtained from genes such as Ang2, Flk1, VEGFR, MHC genes, aP2, GFAP, Otx2 (see, e.g., U.S. Pat. No. 5,639,618), Dlx (Porteus et al. (1991) *Neuron* 7:221-229), Nix (Price et al. (1991) *Nature* 351: 748-751), Emx (Simeone et al. (1992) *EMBO J.* 11:2541-2550), Wnt (Roelink and Nuse (1991) *Genes Dev.* 5:381-388), En (McMahon et al.), Hox (Chisaka et al. (1991) *Nature* 350:473-479), acetylcholine receptor beta chain (ACHRβ) (Otl et al. (1994) *J. Cell. Biochem. Supplement* 18A:177). Other examples of lineage-specific genes from which regulatory elements can be obtained are available on the NCBI-GEO web site which is easily accessible via the Internet and well known to those skilled in the art.

For example, to identify the lineage of cardiomyocytes, control elements from an alpha MHC gene can be used. For identifying smooth muscle lineages, the SM22α promoter can be used. See, e.g., U.S. Pat. No. 6,090,618. For identifying adipocyte lineage, aP2 control elements can be used. For identifying the lineage of neurons, control elements from neuron specific genes such as synapsis or neuron specific enolase can be used. For identifying glial cells, control elements from glial fibrillary acidic protein (GFAP) gene can be used.

The control element (e.g., promoter) may be from the same species as the target cell (e.g., human promoter used in a construct for introduction into human cells), from a different species (e.g., mouse promoter used in a construct for introduction into human cells), or a mixed control element (e.g., some control elements from a mouse gene combined with some control elements of a human gene). The control element(s) can be derived from any gene of interest by methods known in the art (e.g., PCR using primers flanking the control sequences of interest).

Lineage-specific or cell fate promoters can be obtained from a gene of interest by methods known in the art. For example, commercial databases (e.g., ENTREZ and GEN-BANK—National Center for Biotechnology Information; EMBL—The European Bioinformatics Institute, Hinxton, UK) and contemporary scientific literature (MEDLINE B The National Library of Medicine, 8600 Rockville Pike, Bethesda, Md.) can be searched for information about a selected gene including locations of coding and regulatory sequences. Alternatively, methods of identifying regulatory sequences associated with a particular gene are known in the art, for example, deletion analysis or PCR amplification of fragments derived from 5' non-coding regions of a selected gene where these fragments are then operably linked to a reporter gene to identify regulatory (or control) sequences.

Such reporter genes with associated regulatory sequences can be screened, for example, in cultured cells.

Additional non-limiting examples of cell marker gene products and/or lineage-specific or cell fate promoters that can be inserted into stem cells include sequences encoding the cell markers and/or promoter sequences derived from the cell markers show in Table 1 below.

TABLE 1

Examples of Cell Markers

| Cell type | Examples of Potential Marker Genes |
| --- | --- |
| Adipocytes | Adiponectin (also known as Acrp30, AdipoQ, and GBP28), Adipoq, Adipsin, ALK7, ALBP/aP2 (adipocyte lipid-binding protein), C/EBP alpha/beta (CCAAT-enhancer binding protein), DOL54 (a pre-adipocyte marker), FABP (fatty acid binding protein), FABP4, GLUT4, GPDH (glycerol-3-phosphate dehydrogenase), Leptin, LPIN-1, LPL (lipoprotein lipase), Perilipin, PEPCK-C (Phosphoenolpyruvate carboxykinase), PPAR (peroxisome proliferator activated receptor), Pref-1 (Preadipocyte factor-1), Resistin, S-100, UCP-1/UCP-2 (Uncoupling protein), Mest/Peg1, aP2 |
| Alveolar cells | Alkaline phosphatase, Cytokeratin, HTI56, MEP-1, MPA (Maclura pomifera lectin), MPA binding glycoproteins (MPA-gp330), P2X7 and GABRP, pro-SPC, RAGE (receptor for advanced glycation endproducts), RTI(40), SBA (Soybean agglutinin), SPA (surfactant protein A, SP-A), SPB (surfactant protein B, SP-B), SPC (surfactant protein C, SP-C) |
| Ameloblasts | Ameloblastin, Amelogenin, Amelotin, AP-1 family proteins (c-Jun, JunB, JunD, c-Fos, FosB, Fra-1, and Fra-2), APC (adenomatous polyposis coli gene protein), Connexin43 (Cx43), Cytokeratin 14, Enamel matrix proteins (EMP), IGF-I receptor (Insulin-like growth factor-I receptor), TGF-beta 1, TSLC1 (Tumor suppressor in lung cancer-1) |
| Apud cells | Neuron-specific enolase (NSE) |
| eBasal cells | 34betaE12 (high molecular weight cytokeratin), Bcl-2, CD44, Keratin 14, p63, P-Cadherin, S100A6 (Calcyclin) |
| Basophils | BB1 (Basogranulin), Bsp-1, CCR3 (eotaxin-receptor), CD11a/CD11b/CD11c, CD13 (WS-80274, clone A8), CD44 and CD54, CD63 (gp53), CD69, CD107a (WS-80280, clone E63-880), CD164 (WS-80160, clone N6B6 and WS-80162, clone 67D2), CD203c (E-NPP3), CDw17 (lactosylceramide), IL-3, IL-4 Receptors, beta 1, beta 2, and beta 7 integrins, Interleukin-4 (IL-4), MBP (Major Basic Protein), MMCP-8, NCA, PSGL-1 (CD162), TLR4 (Toll-like receptor-4), |
| B-cells | B220, BLAST-2 (EBVCS), Bu-1, CD19, CD20 (L26), CD22, CD24, CD27, CD57, CD72, CD79a, CD79b, CD86, chB6, D8/17, Immunoglobulin Beta (B29), FMC7, L26, M17, MUM-1, Pax-5 (BSAP), PC47H |
| Cancer stem cells | CD7, CD10, CD18 (Integrin β2), CD19, CD20, CD24 (HSA), CD27, CD29 (Integrin β1), CD31 (PECAM-1), CD33, CD34 (Mucosialin), CD38, CD44, CD49b (Integrin α2), CD49f (Integrin α6), CD74, CD90 (Thy-1), CD96 (Tactile), CD105 (Endoglin), CD117 (c-Kit), CD123 (IL-3Rα), CD133 (Prominin-1), CD138 (Syndecan-1), CD166 (ALCAM), CD184 (CXCR4), CD324 (E-cadherin), CD338 (ABCG2), Dll1, EpCAM (TROP-1), Jagged-2, Nestin, Notch1, Notch3, Notch4, Podoplanin, SSEA-1, SSEA-3, SSEA-4, TRA-1-60, TRA-1-80 |
| Cardiomyocytes | Adrenomedullin, ALCAM (CD166), alpha-Actinin, Annexin 5, Annexin 6, ANP (atrial natriuretic peptide), bFGF, BNP (brain natriuretic peptides), Cardiac troponin I (cTnI), Cardiac troponin-T (cTnT), CARP (cardiac adriamycin-responsive protein), Caveolin-2, Caveolin-3, CHAMP, CNP (C-type natriuretic peptide), Connexin-43, Desmin, dHAND, eHAND, GATA-4, GATA-6, H-FABP, Insulin-like growth factor 1 (IGF-1), MEF2C, MHC (myosin heavy chain), MLC (myosin light chain), N-cadherin, Nkx2.5 (cardiac homeobox protein), Oct-4, Pnmt (Phenylethanolamine N-methyltransferase), Sarcomeric alpha Actin/Actinin, Sarcomeric Myosin, Sarcomeric Tropomyosin, Skeletal alpha-Actin |
| Chondrocytes | Aggrecan, Annexin VI, beta 1 Integrin (CD29), COMP (Cartilage oligomeric matrix protein), Cathepsin B, CD44, CD151, and CD49c, CEP-68 (Chondrocyte expressed protein-68), CMP (cartilage matrix protein, Matrilin-1), Collagen II, Collagen IX, Collagen X, IGF-I and IGF-II, MIA (Melanoma Inhibitory Activity), MMP13 (matrix metalloproteinase-13), Osteonectin (SPARC), PCNA, p21, Sox9, Syndecan-3, YKL39 and YKL40 |
| Clara cells | CC10 (Clara cell secretory protein), CC16 (Clara cell secretory protein), CC26, CCSP (Clara cellspan > s secretory protein), CYP2F2/CYP2B4, Cytochrome P-450 (CYP450), NADPH reductase, SP-A, SP-B, SP-C, SP-D, Urinary protein 1, Uteroglobin, UGRP1 |
| Dendritic cells | ADAM19 (MADDAM), BDCA-2, CD1a, CD11c, CD21, CD83, CD86, CD208, CLIP-170/restin, Clusterin, DC-LAMP (CD208), DEC-205, Estrogen Receptor-alpha, Fascin, HLA-DR, NLDC-145, S-100 |

TABLE 1-continued

Examples of Cell Markers

| Cell type | Examples of Potential Marker Genes |
|---|---|
| Endothelial cells | ACE (angiotensin-converting enzyme), BNH9/BNF13, CD31 (PECAM-1), CD34, CD54 (ICAM-1), CD62P (p-Selectin GMP140), CD105 (Endoglin), CD146 (P1H12), D2-40, E-selectin, EN4, Endocan (ESM-1), Endoglin (CD105), Endoglyx-1, Endomuci, Endosialin (tumor endothelial marker 1, TEM-1, FB5), Eotaxin-3, EPAS1 (Endothelial PAS domain protein 1), Factor VIII related antigen, FB21, Flk-1 (VEGFR-2), Flt-1 (VEGFR-1), GBP-1 (guanylate-binding protein-1), GRO-alpha, Hex, ICAM-2 (intercellular adhesion molecule 2), LYVE-1, MRB (magic roundabout), Nucleolin, PAL-E (pathologische anatomie Leiden-endothelium), RPTPmu (Receptor protein tyrosine phosphatase mu), RTKs, sVCAM-1, TEM1 (Tumor endothelial marker 1), TEM5 (Tumor endothelial marker 5), TEM7 (Tumor endothelial marker 7), TEM8 (Tumor endothelial marker 8), Thrombomodulin (TM, CD141), VCAM-1 (vascular cell adhesion molecule-1) (CD106), VE-cadherin (CD144), VEGF (Vascular endothelial growth factor), vWF (von Willebrand factor) |
| Enterocytes | Amino-Peptidase N, Carbonic Anhydrase (CA), Carbamoylphosphate Synthase (CPS), CD10, Dipeptidyl Peptidase IV (DDP IV, CD26), E-Cadherin, Enterocytin, Glucose Transporter-5 (GLUT5), IAP (intestinal alkaline phosphatase), I-FABP (intestinal fatty acid-binding protein), L-FABP (liver fatty acid-binding protein), Lactase, Lectins, Neutral Endopeptidase (Endopeptidase 24.11; NEP; neprilysin), Sodium Glucose co-Transporter 1 (SGLT1), Sucrase Isomaltase (SI), Villin, Zonula Occludens (ZO1, ZO-1) |
| Eosinophils | BMK-13, CD9, CD44 and CD69, ECP (Eosinophil Cationic Protein, EG1/EG2), EDN (eosinophil derived neurotoxin), Eosinophil Peroxidase (EPO), Eosinophil Protein-X (EPX), IL-5, LA Antigen, MBP1/MBP2 (major basic protein), |
| Epithelial cells | A6 antigen, A33 antigen, Adenosine 5'-Triphosphatase (ecto-ATPase), Aminopeptidase N, APN/CD13, AUA1, BG8 (Lewis Y blood antigen), Bmi-1 oncoprotein, BRCA1, BTEB1, CA-125, Calcyclin, CAR-5, Carcinoembryonic Antigen (CEA), Cathepsin E (CaE), CC10 (Clara cell-specific protein), Cystatin C, Cytokeratins 8, 14, 18, and 19, Connexin-43 (Cx43), Desmin, EMA, Exo-1 (Pa-G14), EZH2, Ezrin, Foxal, GABRP, Galectin-3, GGT (gamma-glutamyl transpeptidase), Glutamine Synthetase, H4, HLA-DR, HME1, Keratin 5 (K5), Keratins 13 and 19, KL-6, Lactoferrin, LAMP-1 (lysosomal-associated membrane protein 1), Lectins, Leu-7, LhS28, Ly110, M1, MBEC, MEP-1, MEP7, MOC-31, NSE (neuron-specific enolase), Neutral Aminopeptidase, P2X7, p16, p16 (INK4A), p63, P-Cadherin, Prostate Derived Factor (PDF), PHM-5, PR1A3, Prominin-1 (CD133), Prostate Antigen (PA), Protein Gene Product 9.5(PGP 9.5), Prostatic Binding Protein (PBP), PSCA (Prostate stem cell antigen), Rab13, RAGE, RLA (rat liver antigen), Rex-1 (zinc-finger protein-42, Zfp42), RTE 1, 2, 3, 7, 9 11, 12, 13, RTI40, Secretory Component (SC), SPA, SPB, SPC (surfactant proteins A, B, C), SPRR1B, SQM1 protein, Sucrase-isomaltase (SI), Thioesterase II, Transthyretin, VAT-1, Vimentin |
| Erythrocytes | BGP1, CD36, CD47, CD71 (transferrin receptor), Globin, Glycophorin A (GPA), Glycophorin B, Hemoglobin, Rh Polypeptides and Rh Glycoprotein, N-Acetyl-9-O-Acetylneuraminic Acid, TER119, VLA4 |
| Fibroblasts | ER-TR7, FSP1, prolyl 4-hydroxylase (5B5) |
| Germ cells | 43-9F, AFP (alpha-fetoprotein), Aggrus, AP-2gamma, Axdazl, BMP15 (bone morphogenetic protein 15, CA-125, c-Kit (CD117), DAZ-like 1(DAZL1), Dppa3, EGFR (Epidermal growth factor receptor), GCNA1 (germ cell nuclear antigen 1, GCNA-1), GDF9 (growth and differentiation factor 9, Glypican 3, GP90-MC301, Keratin 7, Lactate Dehydrogenase (LD), Lactate Dehydrogenase Isoenzyme, LDH (lactate dehydrogenase isoenzyme 1), M2A, M-CSF, MAGE-44, MATER, OCT ¾, p53, PD-GFA, PLAP, Podoplanin, Proacrosin, RBMA (RNA-binding motif), telomerase, Tesmin, TEX101, TRA-1-60, VASA, ZAR1, GCAP, sACE, Notch-1, c-kit, GFRalpha-1 |
| Glial cells | A2B5-antigen (A2B5), GD3, O4-antigen (O4), RC1, Sox-1/Sox-2. Vimentin |
| Goblet cells | CDX-2, CK7, CK20, ITF, Keratin polypeptide 20 (K20), Lectins, Muc2, MUC5AC, MUC5B, PKD (PKCmu), Trefoil Factor (Tff3) |
| Granulosa cells | AMH (anti-mullerian hormone), Aromatase (CYP19A1), chZPC, Follicle regulatory protein (FRP), Inhibin, MCAM (Melanoma cell adhesion molecule, CD146) |
| Hematopoietic Progenitors | AC133, BAALC, CD31, CD34, CD43, CD44, CD45, CD84, CD133/Prominin-1, CDCP1 (CUB-domain-containing protein 1). C-Kit/CD117, Endomucin, Flk-2, Flk-2/Flt3, Flt-3L, LR-1, Ly-5, MYADM, Sca1, SCGF, STK-1, TGF-beta2, Thy-1, |
| Hepatoblasts | alpha-Fetoprotein (AFP), C/EBP alpha, Cytokeratin 8, 14, and 18, Dlk/Pref-1, E-cadherin. Foxn1b, HNF4, Id3, Liv2 (liv-2), Prox1, SEK1, SMAD 5 |
| Interneurons | Paravalbumin, Calretinin, Calbindin, CB1 (type 1 cannabinoid receptor, CCKpan (Cholecystokinin), ChAT (choline acetyl-transferase), Chx10, |

TABLE 1-continued

Examples of Cell Markers

| Cell type | Examples of Potential Marker Genes |
|---|---|
| | DLX, EN1 (pan-Engrailed-1, EN-1), ER81, EVX1, GAD65, GABA(B) receptor 1-like (GBR1-L1), GAD65, GAD67, GATA, GluR-8, ISL1, Lhx 1, Lhx5, Lhx3, Lhx6, mGluR1alpha, MOR, Nkx2-2 (Nkx2.2), NMDAR2D, NOS, Pax2, SDF-1, SPO, Substance P Receptor (SPR) |
| Islet cells | Beta-2/NeuroD, FoxA1, FoxA3, GAD (glutamic acid decarboxylase), GAD65/GAD67, Gdf11, GLUT1, GLUT3, GLUT2, GLUT4, IA2/ICA512, IAPP/amylin, IGRP, INGAP (islet neogenesis-associated protein), IPF1, Islet-1, MafB, Neurogenin 3 (Ngn3), NKX6.1, Pax4, Pax6, PDX-1 (Pancreatic duodenal homeobox factor-1), PEK, STF-1 |
| Keratinocytes | Calmodulin, Calmodulin-like skin protein, CD24 (heat stable antigen, nectadrin), CD34, CD98, Epidermal calcium-binding protein (ECaBP), Filaggrin, GP37, gp80, hKPRP, ICAM-1, Involucrin, Keratinocyte transglutaminase, KL3, KPRP, Minoxidil Sulfotransferase, MTS24, p63, rSQ20 and hSQ16, SPR1 (small proline-rich protein-1), SPRR1, SPRR1A, SPRR1B, SPRR2A, SQM1 protein, Tob |
| Kupfer Cells | BGS-18, CD14, CD68, ED1, ED2, F4/80, Fucose Receptor, G6PD (glucose-6-phosphate dehydrogenase), Lectin, Lysozyme, TNF-α |
| Langerhans Cells | Acetylcholinesterase (AchE), ATPase, CD1a (Leu 6), E-Cadherin, Fascin, Fc gamma-receptor (FcR), HLA-DM, HLA-DR (Ia), KL-6, Langerin (CD207), MHC Class II, MT1, Neuron-Specific Enolase (NSE), OKT6, T6 (CD1) |
| Leydig Cells | 3 beta-HSD (3-hydroxysteroid dehydrogenase, 3b-HSD), 7-dehydrocholesterol reductase (7-DHCR), 11 beta-hydroxysteroid dehydrogenase, Calretinin, Cyp17 and Cyp11a1, Esterase, Inhibin-alpha, IGF-1 (insulin like growth factor-1), INSL3 (Insulin-like factor 3), Ley I-L (Leydig insulin-like gene), LRH-1 (liver receptor homolog-1), Luteinizing Hormone (LH) receptor, Melan-A, Nestin, Neuron-Specific Enolase (NSE), P450arom (cytochrome P450 aromatase), PBR (Peripheral-type benzodiazepine receptor), Relaxin-like factor (RLF), SCC (P450 side-chain cleavage enzyme), STAR (steroidogenic acute regulatory protein), Steroidogenic Factor-1 (SF-1, Nr5a1, and Ad4bp), Thrombospondin 2 (TSP2), 3βHSD VI, PGD-synthetase, EST, 17βHSD III, 3beta-hydroxysteroid dehydrogenase (3beta-HSD) VI, 17beta-hydroxysteroid dehydrogenase (17beta-HSD) III, vascular cell adhesion molecule 1, estrogen sulfotransferase, and prostaglandin D (PGD)-synthetase |
| Leukocytes | 8-OHdG (8-hydroxydeoxyguanosine), Beta2 Leukocyte Integrins (CD11/CD18), Cathepsin G, CD15 (leuM1), CD18 (MHM23), CD43 (leukosialin, leu-22), CD45, CD45RA/CD45RB/CD45RO, CD53 (Ox-44), CD68 (KPI, macrosialin), CD95 (fas), CD166, Diiodotyrosine (DIT), EFCC, Fecal Lactoferrin, Glucose-6-phosphatase (G-6-Pase), HLA (human leukocyte antigen), HLE (Human Leukocyte Elastase), ICAM-1, IL-8 (Interleukin-8), L1, Lactoferrin, LAM-1 (Leukocyte Adhesion Molecule-1), LAP (Leukocyte alkaline phosphatase), Lectins, L-selectin, LSP1 (Leukocyte-specific protein-1), Ly-9, M6 (leukocyte activation antigen), Mac-1, MPO (myeloperoxidase), VIP (Vasoactive Intestinal Polypeptide) |
| Macrophage | Carboxypeptidase M (CPM), Cathepsin K, Chitotriosidase, CD14, CD68 (Ki-M7, Y2/131, Y1/82A, EBM11), CD163, sCD163, CSF-1R (colony-stimulating factor-1 receptor), ED-1, ED-2, EMR1 (epidermal growth factor module-containing mucin-like receptor 1), Factor XIII-A, Ferritin, HAM-56, Ki-M1P, Lysozyme M, MAC-1/MAC-3, Myeloid-related protein (MRP) 14, RFD7/RFD9, RM3/1 |
| Mast cells | Carboxypeptidase A, Chymase, CD25, CD34, CD117 (c-Kit), Ki-MC1, Ki-M1P, LAMP-1/LAMP-2, Mast Cell Tryptase, PDG2 |
| Melanocytes | ETB (endothelin-B) receptor, HMB-45 (gp100), L-PGDS (lipocalin-type prostaglandin D synthase), MATP, Mel1/Mel2, Melan-A (A103), MelEM, Mitf (Microphthalmia-associated transcription factor), PNL2, Tyrosinase (T4), Tyrosinase-related proteins (TRPs)/gp75 |
| Mesenchymal stem cell | Msx1, TAX, Twist1 |
| Merkel Cells | CD56, Chromogranin A (CGA), Cytokeratin 20, Fli-1 and CD99, Go alpha (alpha subunit of guanine nucleotide-binding protein Go), Keratin 20, NSE (neuron-specific enolase), TROMA-1, Villin |
| Mesothelial Cells | Calretinin, Cancer Antigen (CA)125, CD44, CD44H, Cytokeratin 5/6, Desmin, E-Cadherin, HBME-1, Keratin, Keratin7 (K7), MCp130, ME1/ME2, Mesothelin, N-Cadherin, Protein Phosphatase Inhibitor-1 (I-1), Thrombomodulin, Vimentin, WT1 (Wilms' tumour susceptibility gene 1) |
| Monocytes | Adipophilin, Angiotensin Converting Enzyme, CB12, CD11a (LFA-1 alpha), CD11b, CD14, CD15, CD54, CD62L (L-selectin), CD163, Cytidine Deaminase (CDD, EC 3.5.4.5), DH59B, Fc-receptors, Flt-1 (VEGFR-1), HLA-DR, hMGL, Ki-M1p, Leucocyte tartrate-resistant acid phosphatase (FATRE), Leu-&, Lysozyme, Mannosyl Receptors, Peanut Agglutinin (PNA), Thromboplastin, Thymidine Phosphorylase (TP), TNF (Tumor necrosis factor), Urokinase (UK), VEP8 and VEP9, thiol-proteindisulfide-oxidoreductase |
| Motor Neurons | ChAT (choline acetyltransferase), Chox10, En1, Even-skipped (Eve) transcription factor, Evx1/2, Fibroblast growth factor-1 (FGF1 or acidic |

TABLE 1-continued

Examples of Cell Markers

| Cell type | Examples of Potential Marker Genes |
|---|---|
| Myeloid cells | FGF), HB9, Isl1 ( Islet-1), Isl2, Islet1/2, Lim3, Nkx6, p75(NTR) (p75 neurotrophin receptor), REG2, Sim1, SMI32 (SMI-32), Zfh1 Arginase-1, BM-1/BM-2/BM-3/BM-4 (Granulocyte), C1qR(P), CD11a/CD18, CD11b/CD11c, CD13, CD14, CD15, CD18 (beta(2) leukocyte integrin), CD31, CD33, CD34, CD38, CD43, CD123, CD138, CLL-1 (C-Type Lectin-Like Molecule-1), CSC-1, F4/80, Glut3, Elastase, GPIIb-IIIa, GR-1, Lactoferrin (LF), Ly498, Lysozyme, MAC-1, MC52, MO1(CD11b), MPO (myeloperoxidase), MY3, MY4, MY7, MY7/MY9, MY8, MYADM, VIM-D5, Ym1, |
| Myoblasts | Acetylcholinesterase (AChE), ADAM12, alpha- and beta-tropomyosin (pT), beta-Enolase, CD56, Desmin, Lactate Dehydrogenase (LDH), M-Cadherin (muscle cadherin), M-Cadherin (muscle cadherin), M-Calpain, M-CAM (melanoma cell adhesion molecule), MRF4 (myogenic/muscle regulating factor-4), Myf-5 (muscle regulatory factor-5), MyoD, Myogenin, Myosin, nls beta-Galactosidase, N-Cadherin (neural cadherin), p21, Phosphoprotein (pp(65;4.5)), Pax3, Pax7, PK-K (K-isozyme of pyruvate kinase), PK-M (M-isozyme of pyruvate kinase), Tbx3, Titn |
| Myocytes | ANP (Atrial natriuretic peptide), Arpp, BBF-1, BNP (B-type natriuretic peptide), Caveolin-3 (Cav-3), Connexin-43, Desmin, Dystrophin (Xp21), EGFP, Endothelin-1, FABP (Heart fatty-acid-binding protein), GATA-4, MEF-2 (MEF2), MLC2v, Myosin, N-cadherin, Nestin, Popdc2 (Popeye domain containing gene 2), Sarcomeric Actin, Troponin, Troponin I |
| Myoepithelial Cells (MEC) | 14-3-3sigma, alpha-SMA, Caldesmon (CALD), Calponin, Carbonic Anhydrase III (CAIII), CD10, CD29 and 14-3-3sigma, CD109, Cytokeratin 14, Cytokeratin 17, EGFR, L2E3, Maspin, Neuropilin-1, Osteonectin (SPARC), p63, p75 neurotrophin receptor (p75NTR), P-cadherin, SMMHC (Smooth Muscle Myosin Heavy Chain), Thy-1 (thymocyte differentiation antigen), Vimentin |
| Myofibroblasts | Actin, Cadherin-11, Desmin, EDA (ED-A fibronectin), GB 42, Palladin 4Ig, SMA-alpha (smooth muscle actin-alpha), Transforming growth factor (TGF) beta 1, Thy-1, Tropomyosin-1 |
| Natural Killer cells | 2B4, CD2, CD3, CD7, CD16 (Leu 11b), CD33, CD45, CD56, CD57/HNK1, CD69, CD107a, CD161, CS1, HP (Helix pomatia) Receptors, LAT (linker for activation of T cells), Ly24 (Pgp-1), NKG2A and NKp80, NKH1 (N901), Protocadherin 15 (PCDH15) |
| Neural stem cells | CD15, CD24 (HSA), CD29 (Integrin β1}, CD49f (Integrin α6), CD54 (ICAM-1), CD81, CD95 (FAS/APO-1), CD133, CD140a (PDGFRa), CD146, CD184 (CXCR4), CD338 (ABCG2), Nestin, Notch1, SSEA-1 |
| Neurons | ABCA2 (ATP-binding cassette transporter-A2), Acetylcholinesterase, Alz-50, ATF3 (Activating transcription factor 3), Bcl-2, BM88, Calbindin D28, Bag1, Beta-tubulin, c-Fos, Calbindin D28K, Calcineurin, Calretinin, Cerebellin, ChAT (choline acetyltransferase), Cytochrome oxidase, Cystathionine, DSS-3, ELF, HSV-1 (Herpes simplex virus type 1), importin alpha 5, MAG (myelin-associated glycoprotein), MAP2, MIT-23, NAA (N-Acetylaspartate), NADPH-diaphorase, Nestin, NeuN (neuronal nuclei), Neurofilament, Non-angiotensin II [(125)I] CGP42112, NSE (neuron specific enolase), NSP-C (Neuroendocrine-specific protein C), OMP (olfactory marker protein), Pax6, Pitx3, Tbr2, Tbr1, PGP9.5 (neuronal marker protein gene product 9.5), PKC (Protein kinase C), RC3/neurogranin, S199, SBDP120s, SSEA-1, Synapsin 1, TG-1, TGF-beta |
| Neutrophils | 8-hydroxydeoxyguanosine (8-OH-dGUA), B beta 30-43, CD11b, CD18, CD64, C-reactive protein (CRP), Gelatinase, Granulocyte Receptor-1 (Gr-1), HNE ANCAs, HNL (human neutrophil lipocalin), Human Neutrophil Peptides 1-3 (HNP-1-3), L-selectin, Lactoferrin, Lysozyme, Myeloperoxidase (MPO), Neutrophil Alkaline Phosphatase (NAP), Neutrophil Elastase (NE), NGAL (neutrophil gelatinase-associated lipocalin), Polymorphonuclear Meutrophil Elastase (PMN-E) |
| Odontoblasts | Alkaline Phosphatase (ALP), alpha 1 Type 1 Collagen (alpha I type I collagen), DMP1/DMP2 (dentin matrix protein), DPP (dentine phosphoprotein), DSP (dentin sialoprotein, dentinsialoprotein), DSPP (dentin sialophosphoprotein), Enamelysin, Mov13 allele, Nestin, OSAD (Osteoadherin), Osteopontin (OPN), Osteocalcin (OC), Phex (phosphate-regulating gene with homologies to endopeptidases on X-chromosome) |
| Oocytes | Bicaudal-D (Bic-D), BMP15 (bone morphogenetic protein 15), c-kit, c-Mos, GDF9 (growth and differentiation factor 9), HBPP (heparin-binding placental protein), IGFBP-1, Kit Ligand (KL), Leptin, LH Receptor (LH-R), MATER (maternal antigen that embryos require), MSY2, NALP9, Orb, Oskar, p180, Pentraxin 3, VASA, ZP (zona pellucida, ZP1, ZP2, ZP3 or ZPA, ZPB, ZPC), ZAR1 (zygotic arrest 1) |
| Osteoblasts | Alkaline Phosphatase (ALP), alpha 1(I) procollagen, Bone Gla Protein (BGP), Bone Sialoprotein (BSP), Cbfa1/Osf2, Collagen Type I, E11, Osteocalcin, Osteopontin, Phex, RP59 |
| Osteoclasts | acid ATPase, Calcitonin (CT) receptor (CTR), Carboxyterminal Telopeptide of Type 1 Collagen (1CTP), Cathepsin K, CKBB (creatine kinase BB), ED1, Kat1-antigen (Kat1-Ag), P1CP (procollagen carboxyterminal propeptide), RANK, Tartrate-resistant acid ATPase, |

TABLE 1-continued

Examples of Cell Markers

| Cell type | Examples of Potential Marker Genes |
|---|---|
| | TRAP (tartrate-resistant acid phosphatase), Vitronectin Receptor (VR, VNR) |
| Paneth cells | alpha-Defensins (cryptdins), Cryptdins, Cryptdin-1, Cryptdin-2, Cryptdin-3, Cryptdin-4, Defensins, Enhancing factor (EF), GM-CSF (granulocyte-macrophage colony-stimulating factor), HD-5 (Human Defensin 5), Lysozyme, Matrilysin, PLA2 (group II phospholipase A2), Trypsin |
| Pericytes | Alpha-smooth muscle actin (a-SMA), Angiopoietin-1, Angiopoietin-2 (Ang2), CD13, Desmin, Endosialin (CD248), NG2 Chondroitin sulfate proteoglycan, PDGFR-beta, RGS5, Thy-1 |
| Phagocytes | alpha-1-Antitrypsin, c-fms, CD11b/CD18 (beta 2 integrins), CD11c/CD18, CD14, CD36, CD64, CD68, CD204, CR3 (C3 receptor), CSF-1, ED1/ED2, F4/80, Mac-1, MARCO, M-CSF, MITF, MRP8/MRP14, Meloperoxidase (MPO), RFD7, S100 proteins, TAcP (Tartrate-resistant acid phosphatase), TFEC, TPP-ase |
| Platelet (thrombocyte) | AK (adenylate kinase), Annexin V, BTG (beta-thromboglobulin), CD31, CD36, CD49b, CD62, CD62P (P-selectin), CD63 (glycoprotein-53), Glycocalicin (GC), GMP-140 (platelet alpha-granule membrane protein), GPV (Glycoprotein V), LAMP2 (lysosome-associated membrane protein-2), PAC-1, PDMP (platelet-derived microparticles), Platelet-Associated Factor XIIIa, Platelet Factor 4 (PF4), P-selectin (CD62P), Serotonin (5-HT), Thrombospondin (TSP), Thromboxane B2 |
| Pneumocytes | Alkaline Phosphatase, Aquaporin 5 (Aqp-5), Bauhinia purpurea lectin (BPL), Caveolins (Cav-1, -2, and -3), CD44v6, CD208 (DC-LAMP), CP4, Cx43, DC-LAMP (CD208), gp600, HTI56, ICAM-1, KL-6, MUC1, T1alpha, Thomsen-Friedenreich antigen, TF antigen, Thyroid Transcription Factor 1 (TTF-1) |
| Podocytes | alpha-actinin-4, B7-1, CD2AP, CD10, Cortactin, Desmin, Dystroglycan (DG), Ezrin, FAT, GLEPP1 (Glomerular epithelial protein 1), Lmx1b, MAP-LC3 (Microtubule-associated protein 1 light chain 3), Myocilin, NEPH1, Nephrin, P-cadherin, PHM-5, (podocalyxin-like protein in humans), Podocin, Podoplanin, Podocalyxin (PC), Synaptopodin, T-/H-cadherin (CDH13), VEGF, Vimentin, Wilms' tumor-1 protein (WT-1), ZO-1 (zonula occludens-1) |
| Primordial germ cell (gonocyte) | Blimp1, Mili, Miwi, UTF1, AP-2, Eps8, GCNA1, OCT3/4, PLAP, VASA |
| Purkinje cells | Aldolase C (Zebrin II), CaM-PDE (Calmodulin-dependent phosphodiesterase), Car8 CD3 (Leu-4), Calbindin (CaBP, 28-kDa calbindin-D, calcium binding protein Calbindin-D28K), Cerebellin, cGMP-dependent protein kinase, Clusterin, ELF, GABA-T (gamma-aminobutyric acid transaminase), GAD67 (67-kDa isoform of glutamic acid decarboxylase), Guanosine 3':5'-phosphate-dependent protein kinase, HDAC6, HFB-16 (KIAA0864 Protein), Inositol 1, 4, 5-triphosphate receptors (IP3R), L7, MAP2 (microtubule-associated protein 2), MAP-120 kDa, NMDA-NR1 (NMDA-R1 receptor subtype), OMP (olfactory marker protein), P400 protein, P450scc (P450 side-chain cleavage), PCA-1/PCA-2, PCPP-260 (Purkinje cell phosphoprotein of Mr 260,000), PDE5/PDE1B, PDE9A, PEP-19 (PEP19), PMCA (plasma membrane calcium pump), SERCA, Spot 35 protein (S-35), Zebrin I and Zebrin II |
| Pyramid cells | CaMK (calcium/calmodulin-dependent protein kinase II, CaMKII), Emx1, GluR2/3, MAP2 (microtubule-associated protein 2), MATH-2, mGluR1/mGluR5, Neurogranin/RC3, PSD-95/SAP90, RPTPalpha, RPTPgamma (receptor protein tyrosine phosphatase gamma), RPTPzeta/beta, SCIP, SMI-32, Tbr1, Zfp312, Pax6, Tbr2/Eomes, NeuroD |
| Reed-Sternberg cells | CD15 (Leu-M1), CD30 (Ber-H2, Ki-1), CD74 (LN2), Fascin |
| Sertoli cells | ABP (androgen-binding protein), AMH (anti-Mullerian hormone), Calretinin, Cathepsin L, CK18, (Cytokeratin 18), Cytokeratin, Clusterin, Cyclic Potein-2 (CP-2), Dhh (Desert hedgehog), Desmin, Fas/FasL, GATA-1, GATA-4, Inhibin B, M2A, MIS (Mullerian inhibiting substance), Serotonin Receptor, SCF (stem cell factor), Sox9, Sulfated Glycoprotein-1 (SGP-1), Sulfated Gycoprotein-2 (SGP-2), Transferrin, Vimentin, WT1 (Wilms' Tumor suppressor 1, WT-1) |
| Spermatocytes | 8D11, Acrosin Binding Protein (ACRBP), GCNA1, GP90-MC301, Lactate Dehydrogenase-X, (LDH-X), p73/5.7, Pgk-2, Proacrosin, SCP1/SCP2/SCP3 (Synaptonemal Complex Protein), SOX-17, SPTRX-3, TEX101, XMR |
| Spermatozoa | Amidase, Aromatase, CD46, TEPA |
| Stellate cells | alpha-SMA (smooth muscle actin, alpha), c-Myb, CRP2 (cysteine- and glycine-rich protein 2), Desmin, FAP (Fibroblast Activation Protein), GFAP, Reelin, S100, Synaptophysin, Vimentin, Vinculin |
| Stromal cells | Cadherin-11, Calretinin, CD10, CD117, Desmin, Endoglyx-1, Endosialin (TEM1, CD248), Fibroblast-Activation Protein (FAP), Neural Ganglioside GD2, Nucleostemin, Snep (stromal nidogen extracellular matrix protein), Tenascin, CD13, CD29, CD44, CD63, CD73, CD90, CD166, STRO-1, HOP-26 (CD63), CD49a, SB-10 (CD166), Alpha and beta subunits of inhibin/activin, Alpha-smooth muscle actin |

TABLE 1-continued

Examples of Cell Markers

| Cell type | Examples of Potential Marker Genes |
| --- | --- |
| Stem cells | 4G10.3, AA4, AC133, Bcrp/ABCG2, c-Mpl, CD9, CD15, CD24, CD29, CD30, CD34, CD133 (Prominin-1), CDCP1, Connexin 43, Endoglin, ER-MP12, Fibroblast growth factor receptor-3, Flk-2, gpt, Human Rex-1 (hRex-1), importin alpha 1, Interleukin-2 receptors, Interleukin-3 receptor alpha chain, KDR, Keratin 19, c-kit, Lamin A/C, Macromolecular insoluble cold globulin (MICG), Musashi-1, Nanog, Nestin, N otch1, Nucleostemin, Oct4 (Oct-4), p63, Podocalyxin, R2/60, PSCA (Prostate stem cell antigen), Sox1, SOX2, SSEA-1, SSEA-3, Stem cell Antigen 1 and 2 (Sca-1 and Sca-2), Telomerase, Thy-1, Transcription factor Stat5, |
| Synaptic cells | Brain spectrin, Chromogranin A/Chromogranin C, Con A-binding glycoprotein, D2-protein, D3-protein, GAP-43 (Growth-Associated Protein-43), NCAM/N-CAM D2 (Neural cell adhesion molecule), p65, PSD95 (Post-Synaptic Density protein-95), Secretogranin II, Synapsin, Synaptin, Synaptobrevin, Synaptogyrin (p29), Synaptophysin, Synaptoporin, Synaptotagmin I, Syntaxin, SV2 (Synaptic vesicle protein 2), Vesicular glutamate transporters (VGLUT1 and VGLUT2) |
| T cells | ART2, CD1a, CD1d, CD2, CD3, CD4, CD5, CD7, CD8, CD11b (Mac-1), CD25 (interleukin 2 receptor alpha), CD38, CD45RO, CD72, CD134 (OX40), CD150, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), TSA-2 (Thymic shared Ag-2) |
| Theca cells | Alkaline phosphatase (AP), BMP-4, CYP17, NR5A1 (steroidogenic factor-1, SF-1) |
| Thymocytes | 20 alpha SDH, CD1, CD1a, CD2, CD4, CD5, CD8, CD25, CD26, CD45RA, CD53, CD69, CD71, CD150, CTX (cortical thymocyte-specific antigen of Xenopus), GIX, Granzymes, H-2, H-2D, HBA-71, ICT-1 antigen (thymocyte differentiation antigen), IL-7, Immature thymocyte antigen-1 (IMT-1), J11d (heat-stable antigen), JL1, LFA-1 (lymphocyte function associated antigen-1) beta, Ly-1/Ly-2, Ly-2/3, Ly-24 and Ly6C, M241, MRC OX-2, Peanut agglutinin (PNA) receptor, Sca-1/Sca-2 (stem cell antigen), T3 (OKT 3), T6 (OKT 6), TAP (T cell-activating protein), THAM (thymocyte-activating molecule), Thy-1, Thy-1.1, Thy-2, Thymic shared antigen-1 (TSA-1), TL antigens (thymus leukaemia antigens), TL3, H-2, TL, Ly 1 and Ly 2, Thy-1, Ly-1, Ly-2, T200,T1, T4, T5, T6, T8 |
| Trophoblasts | Cdkn1c, Cdx2, CHL1, Cytokeration, Cytokeratin-7 (CK7), Dlx3, FD0161G, Gcm1 (glial cells missing 1), H315, H316, Hand1, HASH2, hCG (human chorionic gonadotropin), hCG-beta (Human chorionic gonadotrophin beta), HLA-A/HLA-B/HLA-C/HLA-G, hPL (human placental lactogen), Id-1, Id2, I-mfa, Inhibin A, Integrins, Kip2, M30, Mash2, MNF116, NDOG1/NDOG2, OKT9, PAI-1 (plasminogen activator inhibitor-1), PHLDA2, Placental Lactogen (PL-1, PL-2), PLP-A/PLP-B/PLP-C/PLP-D/PLP-E/PLP-F/PLP-L/PLP-M/PLP-N, SBU-1, SP-1, TA1/TA2 (trophoblast antigens), Tfeb |

Thus, cell fate genes may also be used in the methods of the invention. These genes may be used for insertion into an endogenous, safe harbor locus such that expression of the cell fate specific gene(s) causes the cell to enter into or progress through a differentiation pathway towards a desired lineage-specific or mature differentiated cell type. In some embodiments, these cell fate genes are inserted into the safe harbor locus and do not include a promoter such that expression is driven by an endogenous promoter.

Reporter expression cassettes useful in the practice of the present invention can be constructed using any control element of interest operably linked to suitable reporter gene coding sequences. Reporter genes that encode easily assayable marker polypeptides are well known in the art. In general, a reporter gene is a gene that is not present or expressed by the recipient organism or tissue and that encodes a polypeptide whose expression is manifested by some easily detectable property, e.g. phenotypic change or enzymatic activity and thus when co-transfected into recipient cells with a gene of interest, provide a means to detect transfection and other events. Non-limiting examples of suitable reporters include fluorescent proteins (e.g. GFP or RFP), luciferase, LacZ, beta-galactosidase, chloramphenicol acetyl transferase (CAT) and the like. Selectable markers such as genes encoding for antibiotic resistance may also be employed. Additionally, endogenous genes with the stem cells may be utilized as reporter genes by the specific insertion of heterologous regulatory sequences that cause a differential and measurable change in expression of that endogenous gene.

The type of reporter gene employed will depend on the desired goal of the experiment. For example, to follow the differentiation pathway of a specific lineage, or, to test the developmental specificity of the enhancer, a reporter construct which allows tracking by visual observation is typically used in conjunction with a lineage-specific control element (i.e., histochemistry). This can be used for tracking and characterization of cell lineages and differentiation branch points. Once lineages are characterized, this same system can be used for the isolation of lineage and stage specific stem cells by simply substituting the type of reporter gene from a histochemical marker to a surface membrane protein. Promoter specificity will direct expression of the surface protein at the desired stage of isolation and fluorescent activated cell sorting (FACS) will allow the efficient isolation of the desired stem cell. Other immunological separation techniques such as panning may also be applicable for stem cell isolation.

Additional gene sequences that can be inserted may include, for example, wild type genes to replace mutated sequences. For example, a wild type Factor IX gene sequence may be inserted into the genome of a stem cell in which the endogenous copy of the gene is mutated. The wild type copy may be inserted at the endogenous locus; or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Targeted insertion of non-coding (including regulatory sequences and non-protein-coding sequences) nucleic acid sequence may also be achieved. Sequences encoding antisense RNAs, RNAi, shRNAs and micro RNAs (miRNAs) may also be used for targeted insertions. Additionally, regulatory sequences of other such nucleic acid elements such as unlinked promoters may be specifically introduced to create cell lines for later studies. Further, the control elements of the genes of interest can be operably linked to reporter genes to create chimeric genes (e.g., reporter expression cassettes). In some embodiments, the control elements of the genes are responsive to small molecules (tetracycline or doxycycline for example only).

In other embodiments, a sequence of interest encoding a functional polypeptide is inserted into a targeted spot in the genome of a stem cell, for example a sequence encoding a therapeutic polypeptide. Non-limiting examples of polypeptide-encoding sequences include sequences encoding EPO, VEGF, CCR5, ERα, Her2/Neu, Tat, Rev, HBV C, S, X, and P, LDL-R, PEPCK, CYP7, Fibrinogen, ApoB, Apo E, Apo (a), renin, NF-κB, I-κB, TNF-α, FAS ligand, amyloid precursor protein, atrial naturetic factor, ob-leptin, ucp-1, IL-1, IL-2, IL-3, IL-4, IL-5, IL-6, IL-12, G-CSF, GM-CSF, PDGF, PAF, p53, Rb, fetal hemoglobin, dystrophin, eutrophin, GDNF, NGF, IGF-1, VEGF receptors flt and flk, topoisomerase, telomerase, bcl-2, cyclins, angiostatin, IGF, ICAM-1, STATS, c-myc, c-myb, TR, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, Factor VIII, Factor IX, starch synthase, cellulose synthase, sucrose synthase, senescence-associated genes, heavy metal chelators, fatty acid hydroperoxide lyase, viral genes, protozoal genes, fungal genes, and bacterial genes. Suitable therapeutic proteins also include expression cassettes encoding whole antibodies, antibody fragments, single chain antibodies, intrabodies and the like. Protein aptamers, zetakines, modified or engineered T cell receptors and dominant negative or decoy proteins are also contemplated. Additional therapeutic proteins may be those used in enzyme replacement therapy such as imiglucerase, beta-glucocerebrosidase, alpha-galactosidase A, alpha-L-iduronidase, N-acetylgalactosamine 4-sulfatase and acid alpha-glucosidase. In general, suitable genes to be regulated include cytokines, lymphokines, growth factors, mitogenic factors, chemotactic factors, onco-active factors, receptors, potassium channels, G-proteins, signal transduction molecules, and other disease-related genes. In certain embodiments, the integrated sequences encodes a plasma-soluble polypeptide such as Epo, VEGF or the like.

Various forms of the different embodiments of the invention, described herein, may be combined.

Any stem cell from any species can be used in the compositions and methods described herein. Non-limiting examples of suitable stem cells include hematopoietic stem cells, mesenchymal stem cells, embryonic stem cells, neuronal stem cells, muscle stem cells, liver stem cells, skin stem cells, induced pluripotent stem cells, intestinal stem cells, and the like. Additional stem cells are well known to the skilled artisan.

Zinc Finger Nucleases

The reporter constructs described herein are advantageously integrated into to the genome of a cell using one or more zinc finger nucleases (ZFNs). ZFNs comprise a zinc finger protein (ZFP) and a nuclease (cleavage) domain.

A. Zinc Finger Proteins

Zinc finger DNA binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered (non-naturally occurring) zinc finger DNA binding domain can have a novel binding specificity, compared to a naturally-occurring zinc finger protein. Generally, a non-naturally occurring engineered recognition helix region provides the novel binding specificity. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger DNA binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. Examples of additional linker structures are found in U.S. Patent Publication No. 20090305419.

In certain embodiments, a four-, five-, or six-finger zinc finger binding domain as is fused to a cleavage half-domain, such as, for example, the cleavage domain of a Type IIs restriction endonuclease such as FokI. One or more pairs of such zinc finger/nuclease half-domain fusions are used for targeted cleavage, as disclosed, for example, in U.S. Patent Publication Nos. 20050064474 and 20070218528.

For targeted cleavage, the near edges of the binding sites can separated by 5 or more nucleotide pairs, and each of the fusion proteins can bind to an opposite strand of the DNA target. Following the present disclosure, ZFNs can be targeted to any sequence of any gene in the selected stem cell, including for example CCR5, PPP1R12C (also known as AAV S1) as well as others. See, International Patent Publication WO/2008/133938 and U.S. Patent Publication No. 2008015996 describing ZFNs targeted to CCR5 and AAV S1, incorporated by reference herein. In certain embodiments, the ZFNs are targeted to a "non-essential" gene in that targeted integration into that site does not interfere with the cells ability to proliferate and/or differentiate.

B. Cleavage Domains

The ZFNs also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31, 978-31, 982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively; a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:

I499L". As described in the examples a pair of ZFNs in which one ZFN comprises the "E490K:I538K" cleavage domain and other comprises "Q486E:I499L" cleavage domain is also referred to as a "EL/KK" ZFN pair. The engineered cleavage half-domains described herein are obligate heterodimer mutants in which aberrant cleavage is minimized or abolished when one or more pairs of nucleases containing these cleavage half-domains are used for cleavage. See, e.g., U.S. Patent Publication No. 20080131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively).

In another aspect, engineered cleavage half domains that display conditional activity are provided. In some embodiments, the conditional engineered cleavage half domains display a decrease in activity under decreased temperature conditions. In some embodiments, the conditional engineered cleavage half domains display a decrease in activity under increased temperature conditions.

In yet another aspect, engineered cleavage half domains may be incorporated into zinc finger nucleases comprising non-canonical zinc-coordinating residues (e.g. CCHC rather than the canonical C2H2 configuration).

Engineered cleavage half-domains described herein can be prepared using any suitable method, for example, by site-directed mutagenesis of wild-type cleavage half-domains (Fok I) as described in U.S. Patent Publication Nos. 20050064474 (Example 5) and 20070134796 (Example 38).

In yet another embodiment, two cleavage half-domains are used wherein one of the half domains is enzymatically inactive, such that a single-stranded nick is introduced at the target site (see for example co-owned U.S. Patent Publication No. 20100047805.

C. Additional Methods for Targeted Integration into Stem Cells

Any nuclease can be used in the methods disclosed herein. For example, naturally-occurring homing endonucleases and meganucleases have very long recognition sequences, some of which are likely to be present, on a statistical basis, once in a human-sized genome. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66.

In some embodiments, the DNA binding domain is an engineered domain from a TAL effector derived from the plant pathogen *Xanthomonas* (see Boch et al, (2009) *Science* 29 Oct. 2009 (10.1126/science.117881) and Moscou and Bogdanove, (2009) *Science* 29 Oct. 2009 (10.1126/science.1178817).

Thus, any naturally occurring or engineered nuclease having a unique target site can be used instead of, or in addition to, a zinc finger nuclease, for targeted integration of sequences such as lineage-specific reporters into stem cells. In addition, domains from these naturally occurring or engineered nucleases can also be isolated and used in various combinations. For example, the DNA-binding domain from a naturally occurring or engineered homing endonucleases or meganuclease can be fused to a heterologous cleavage domain or half domain (e.g., from another homing endonuclease, meganuclease or TypeIIS endonuclease). These fusion proteins can also be used in combination with zinc finger nucleases described above.

Delivery

The reporter constructs and nucleases (e.g., ZFNs) described herein may be delivered to a target stem cell by any suitable means.

Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Polynucleotides encoding nucleases (e.g. ZFNs) and the sequence to be integrated (e.g. lineage-specific reporter constructs) as described herein may also be delivered using vectors containing sequences encoding one or more of the ZFNs and/or sequences to be integrated. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors, may comprise one or more ZFN encoding sequences and/or one or more sequences of interest. For example, when one or more pairs of ZFNs are introduced into the cell, the ZFNs may be carried on the same vector or on different vectors. When multiple vectors are used, each vector may comprise a sequence encoding one or multiple ZFNs and/or one or multiple reporter constructs.

Conventional viral and non-viral based gene transfer methods can be used to introduce nucleic acids encoding ZFNs and/or integrating sequences (e.g., reporter constructs) in cells (e.g., mammalian cells) and target tissues. Such methods can also be used to administer such nucleic acids to stem cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994), incorporated by reference herein.

Methods of non-viral delivery of nucleic acids encoding engineered ZFPs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids. In addition, mRNAs encoding the engineered ZFPs may also be delivered to the cells by any suitable means known in the art.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.) and Copernicus Therapeutics Inc., (see for example U.S. Pat. No. 6,008,336).

Lipofection is described in for example, U.S. Pat. No. 5,049,386; U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral; lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In certain embodiments, the nucleic acids (e.g., encoding the ZFNs and/or sequences to be integrated) are delivered using viral vectors such as lentiviral vectors. Lentiviral transfer vectors can be produced generally by methods well known in the art. See, e.g., U.S. Pat. Nos. 5,994,136; 6,165,782; and 6,428,953. Preferably, the lentivirus donor construct is an integrase deficient lentiviral vector (IDLV). IDLVs may be produced as described, for example using lentivirus vectors that include one or more mutations in the native lentivirus integrase gene, for instance as disclosed in Leavitt et al. (1996) *J. Virol.* 70(2):721-728; Philippe et al. (2006) *Proc. Nat'l Acad. Sci. USA* 103(47):17684-17689; and WO 06/010834. In certain embodiments, the IDLV is an HIV lentiviral vector comprising a mutation at position 64 of the integrase protein (D64V), as described in Leavitt et al. (1996) *J. Virol.* 70(2):721-728. Additional IDLV vectors suitable for use herein are described in U.S. Patent Publication No. 20090117617, incorporated by reference herein.

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene-therapy trial. (Blaese et al., *Science* 270:475-480 (1995)). Transduction efficiencies of 50% or greater have been observed for MFG-S packaged vectors. (Ellem et al.,

*Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998). See, also, U.S. Patent Publication No. 20080159996 which describes use of Ad5/35 vectors for delivery of ZFNs, incorporated by reference herein.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many applications, it is desirable that the vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, or for re-infusion of the transfected cells (e.g., stem cells) into the host organism is well known to those of skill in the art. In a preferred embodiment, cells, are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients). Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)) or by selection for CD34+ human stem cells (D J Richel et al., (2000). *Bone Marrow Transplantation,* 25: 243-249).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of reporter construct into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

Applications

The methods and compositions disclosed herein have a variety of applications. Targeted integration of one or more sequences comprising promoters from endogenous genes (e.g., lineage-specific or cell fate promoters) operably linked to coding sequences (e.g., reporters) into a stem cell can be used to identify expression patterns of the endogenous gene. The endogenous promoters may be those associated with a specific differentiation state or determination of cell fate of the stem cell. In certain embodiments, the inserted sequences are integrated into a 'safe harbor' (non-essential gene) locus allowing for expression of a gene of interest without any deleterious effect on the genome, and without any spurious regulation from surrounding endogenous regulatory sequences.

Inserted sequences can be regulated by constitutive regulatory systems, tissue-specific regulatory sequences or may be used with inducible systems wherein expression is regulated by introduction of an exogenous factor such as a small molecule. Sequences inserted into the stem cells may include protein encoding sequences and/or lineage-specific reporter constructs, insertion of general reporter genes for other genes of interest, reporters for genes involved in cell fate determination, and non-protein-coding sequences such as micro RNAs (miRNAs), shRNAs, RNAis and promoter and regulatory sequences.

Stem cells comprising transgenes integrated into a specified region of the genome (e.g., lineage-specific or cell fate reporters, protein coding sequences, etc.) can be used for various differentiation studies, for purification of differentiated cells of a selected lineage and for protein production. For example, targeted insertion of lineage-specific or cell fate reporters into stem cells of any type allows for differentiation studies, and also for differential cell purification. With traditional integration methods, reporter cassettes are randomly integrated into the host cell genome. Position effects from the flanking sequences affect the reporter gene expression causing high and varied background or transgene silencing over time. Thus, in the stem cells described herein, target integrated reporter cassette will have the same chromatin environment, therefore are uniformly expressed in different cells. In addition, targeted integration also allows for expression of the transgene (e.g., lineage-specific or cell fate reporter construct) in only selected lineages maturing from the stem cell.

The stem cells described herein also include cells in which a promotorless marker construct is integrated into an endogenous locus such that expression of the gene product (e.g., lineage-specific or cell fate gene) is driven by the endogenous regulatory sequences at the selected locus, thereby converting said locus into a reporter of cell fate or developmental lineage.

Stem cells marked with lineage-specific or cell fate reporters can be used to screen for compounds such as nucleic acids or small molecules, and/or in vitro methods, that can drive a population of stem cells down a particular lineage pathway of interest into a lineage-specific or mature cell type. Stem cells marked with lineage-specific or cell fate reporters can also be used for a tracking system to follow the in vivo position and ultimately the final location, overall biodistribution, differentiation fate, and mechanism of action of tissue integration of the stem cells following introduction into a subject. Sequences may be inserted into one or more alleles of the host cell, and alternatively different alleles may carry different insertion sequences.

Stem cells can be marked with reporter proteins (e.g., HTK) or inserted sequences can be used for introduction of suicide cassettes. In addition, purification of a differentiated cell population may be achieved by insertion of a suicide gene under the control of a regulatory element that exerts control either only in non-differentiated cells, or in cells which have differentiated into a non-desired lineage. This purified subpopulation could then be used in screening and characterization studies for small molecule or other factors which could influence differentiation. In some embodiments, suicide cassettes are used to facilitate the identification and isolation of a specific type of differentiated subpopulation of cells from a larger cell population. In other embodiments, suicide cassettes are used to destroy stem cells which have differentiated into any undesirable state in vivo, for example if the cells differentiated and formed a teratoma.

Patient-derived hiPSCs from patients with specific diseases can also be used to establish in vitro and in vivo models for human diseases. Genetically modified hESCs and hiPSCs could be used to improve differentiation paradigms, to over-express disease related genes, and to study disease pathways by loss of function experiments.

Reporter-tagged stem cells, either wild type or patient-derived, can be used to study disease processes in a selected homogenous set of cells. For example, a promoter from a gene known to be involved in the pathology of a specific disease in a specific tissue could be linked to a reporter gene and introduced into a stem cell as described herein. Following differentiation of the stem cell into the selected cell type, the reporter system could be used to study the disease in this homogeneous cell population. These cells could be used for screening compounds that modulate expression of the tagged gene. Alternatively, reporters linked to genes known to be involved in tissue-specific toxicities (i.e. p450 in hepatocytes) could be used as tools for screening drug safety on a consistent and homogenous population of target cells differentiated from the marked stem cells.

Likewise, stem cells expressing one or more polypeptides can be used as cellular vehicles for protein-supplement gene therapy. In contrast to traditional integration methods in which a construct is randomly integrated into the host cell genome, integration of constructs as described herein to a specified site allows, in the case of e.g., lineage-specific or cell fate reporter constructs, correct expression only upon differentiation into the cognate lineage-specific cell type or mature cell type, and in the case of protein expression constructs, uniform expression between cells of the population. The targeted insertion of coding sequences into stem cells provides a cellular vehicle for protein-supplement gene therapy while minimizing or eliminating the risk of insertional mutagenesis caused by non-specific integration. Stem cells containing specific integrations of therapeutic proteins may be utilized in the treatment of a variety of diseases or conditions, e.g., in the treatment of Parkinson's Disease, Alzheimer's Disease, hemophilia, amyotrophic lateral sclerosis, spinal cord injury, burns, lung disease, sickle cell anemia, organ failure, heart disease, diabetes, Gaucher's disease, Fabry disease, Mucopolysaccharidosis and Pompe disease. By way of example only, genes encoding therapeutic proteins that could be utilized might include Factor IX, Erythropoeitin and the like. In addition, insertion of wild type copies of genes into stem cells derived from donors with a mutant endogenous gene also allows for various therapies.

In another embodiment, stem cells with two reporters linked to two endogenous genes are envisioned. One reporter could be used to isolate cells heading towards a particular cell fate. The second marker is linked to a gene known to be expressed in the desired lineage-specific or mature differentiated cell. In this way, differentiated cells comprising a tagged endogenous gene know to be involved in a particular metabolic pathway could be produced (i.e. insulin production in pancreatic beta cells).

Doubly tagged stem cells could be used to study complicated processes such as the development of a cancer stem cell from a differentiated cell population. Differentiated cells could be isolated from a stem cell population using a reporter gene linked to a cell fate reporter, as described previously, and then a second reporter could be linked to a de-differentiation marker in a effort to determine what external or internal conditions cause a cell to de-differentiate, potentially into a cancer stem cell.

Differentiated cell populations isolated using a reporter of lineage or cell fate as described previously could have a second marker gene comprising a suicide marker linked to a de-differentiation marker such that if the cells begin to revert to a potentially troublesome stem cell like state, the de-differentiation would induce the suicide gene and kill those cells. This could potentially address safety concerns regarding the use of stem cells in vivo as therapeutics.

Thus, the present disclosure provides methods and compositions for integrating a sequence (e.g., a lineage-specific or cell fate reporter construct or polypeptide encoding sequence) into a stem cell, for example a human, mouse, rabbit, pig or rat cell. Targeted integration of the construct is facilitated by targeted double-strand cleavage of the genome in the region of interest. Cleavage is targeted to a particular site through the use of fusion proteins comprising a zinc finger DNA binding domain, which can be engineered to bind any sequence of choice in the region of interest, and a cleavage domain or a cleavage half-domain. Such cleavage stimulates targeted integration of exogenous polynucleotide sequences at or near the cleavage site. In embodiments in which a lineage-specific or cell fate reporter construct is integrated into a stem cell, the reporter construct typically comprises a promoter from a gene expressed during differentiation operably linked to a polynucleotide encoding a reporter sequence.

The following examples set forth specific embodiments of the invention. It should be recognized that other lineage-specific regulatory regions from other genes that are markers of lineage-specific differentiation can be substituted for aP2 and that various reporter proteins, culture conditions and isolation methods can be substituted without departing from the scope of the invention. Likewise, it will be recognized that polypeptide-encoding sequences other than or in addition to Epo can be integrated into specific regions of a stem cell genome.

EXAMPLES

Example 1: Targeted Integration of an Adipocyte-Specific Reporter

An adipocyte-specific reporter construct was generated by operably linking the promoter sequence of adipocyte fatty acid-binding protein aP2 or ALBP to a GFP reporter sequence. See, e.g., Creaser et al. (1996) Nucleic Acids Res. 24(13):2597-2606 which describes human, mouse and chicken aP2 promoter sequences and is incorporated herein by reference.

Briefly, a 600 bp enhancer and a 200 bp basal promoter of the mouse aP2 gene were cloned and linked together. Subsequently, the linked aP2 control elements were cloned in place of hPGK promoter in the IDVL lentiviral vector designated CCR-LVGFP as described in U.S. Patent Publication No. 20090117617. The resulting reporter construct, designated CCR5-aP2-eGFP, includes the aP2 control elements (promoter/enhancer) driving expression of GFP and flanked by sequences exhibiting homology to the CCR5 gene. See, FIG. 1. In addition, as a control, an integrating lentiviral vector comprising CCR5 homology arms flanking aP2-GFP reporter cassette was also constructed.

Figure 2:
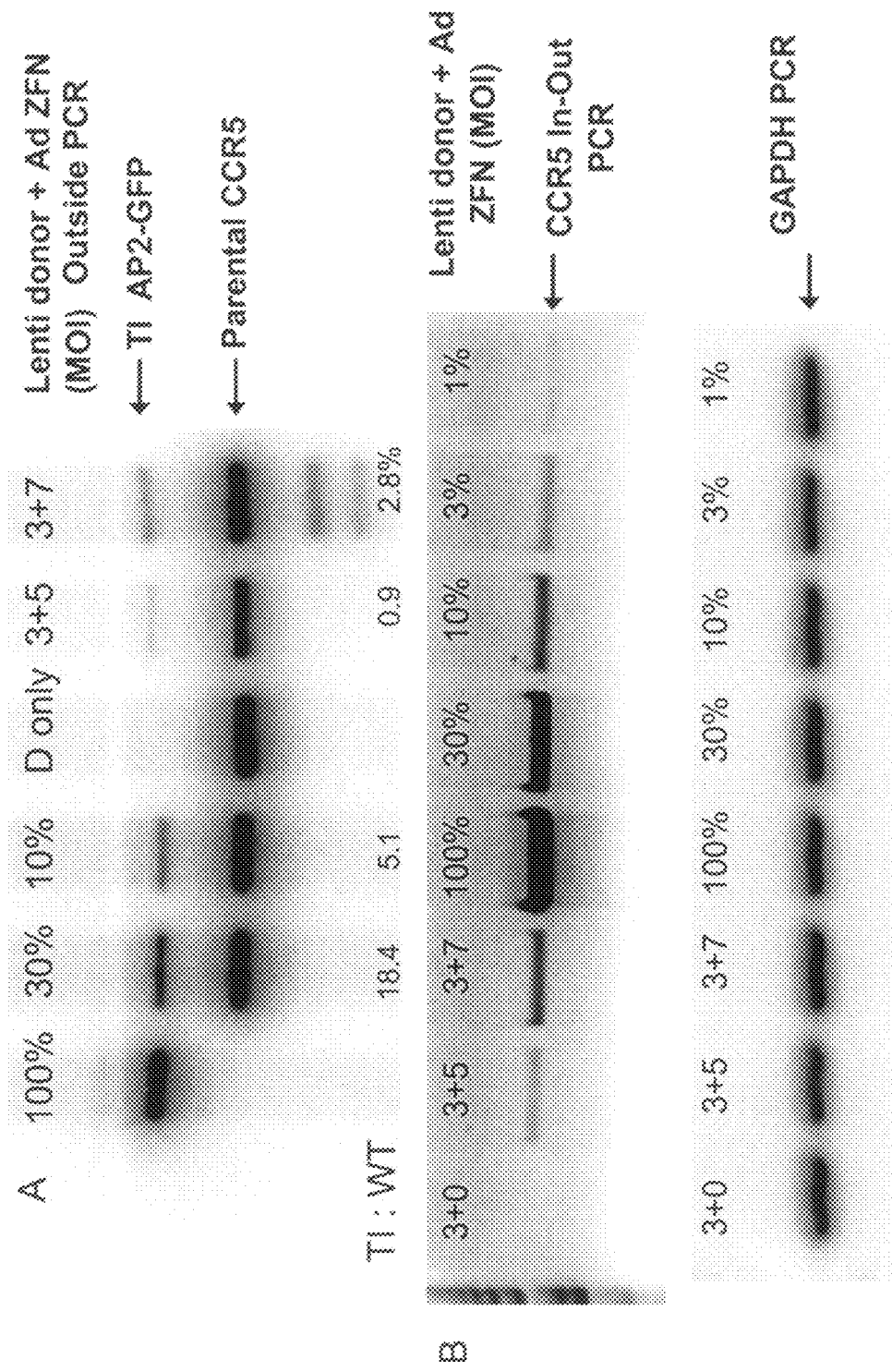
FIG. 2, panels A and B, show targeted integration of the adipocyte-specific IDLV shown in FIG. 1 into human mesenchymal stem cells (hMSCs) cells in the presence of CCR5-specific Zinc finger nuclease delivered by a non-replicating recombinant Ad5/F35 vector (referred to hereafter as Ad.ZFN). At the bottom of each lane of the top panel the percentage of cells with integrated reporter constructs is shown.

The integrating and integration defective lentiviral donor constructs were separately transduced into human mesenchymal stem cells (hMSCs) cells in the presence of CCR5-specific ZFNs delivered by an Ad5/F35 recombinant vector targeted to CCR5 at different MOI. See, U.S. Patent Publication No. 20080159996 for a complete description of the CCR5-specific ZFNs delivered by an Ad5/F35 vector, which publication is incorporated by reference herein. After 4 passages, genomic DNA was isolated from the transduced cells and PCR was performed to detect the mouse aP2-eGFP expression cassette target integration at CCR5 locus. FIG. 2 shows the results of the integration. Lanes marked '100%', '30%', '10%' etc., down to '1%' illustrate spiked controls where mixtures were made to simulate the results of either 100%, 30%, down to 1% targeted integration. At the bottom of the lanes is shown the results detected by the PCR. 'D only' indicates cells transduced with the Lentiviral donor only (without the ZFNs). Top panel shown the results of a PCR experiment where the primers are specific for regions outside the donor arms ('Outside PCR') while the middle panel shows the results of a PCT experiment where one primer is specific for a region outside the homology arm while the other is specific for a region within the donor sequence ('In-Out PCR').

As shown in FIG. 2, a clear PCR band was observed in all the samples from cells transduced with both the Lentiviral donor and the AdZFN. As a control, a GAPDH-specific PCR was also carried out to verify equal levels of DNA were loaded into the PCR reactions.

Figure 3:
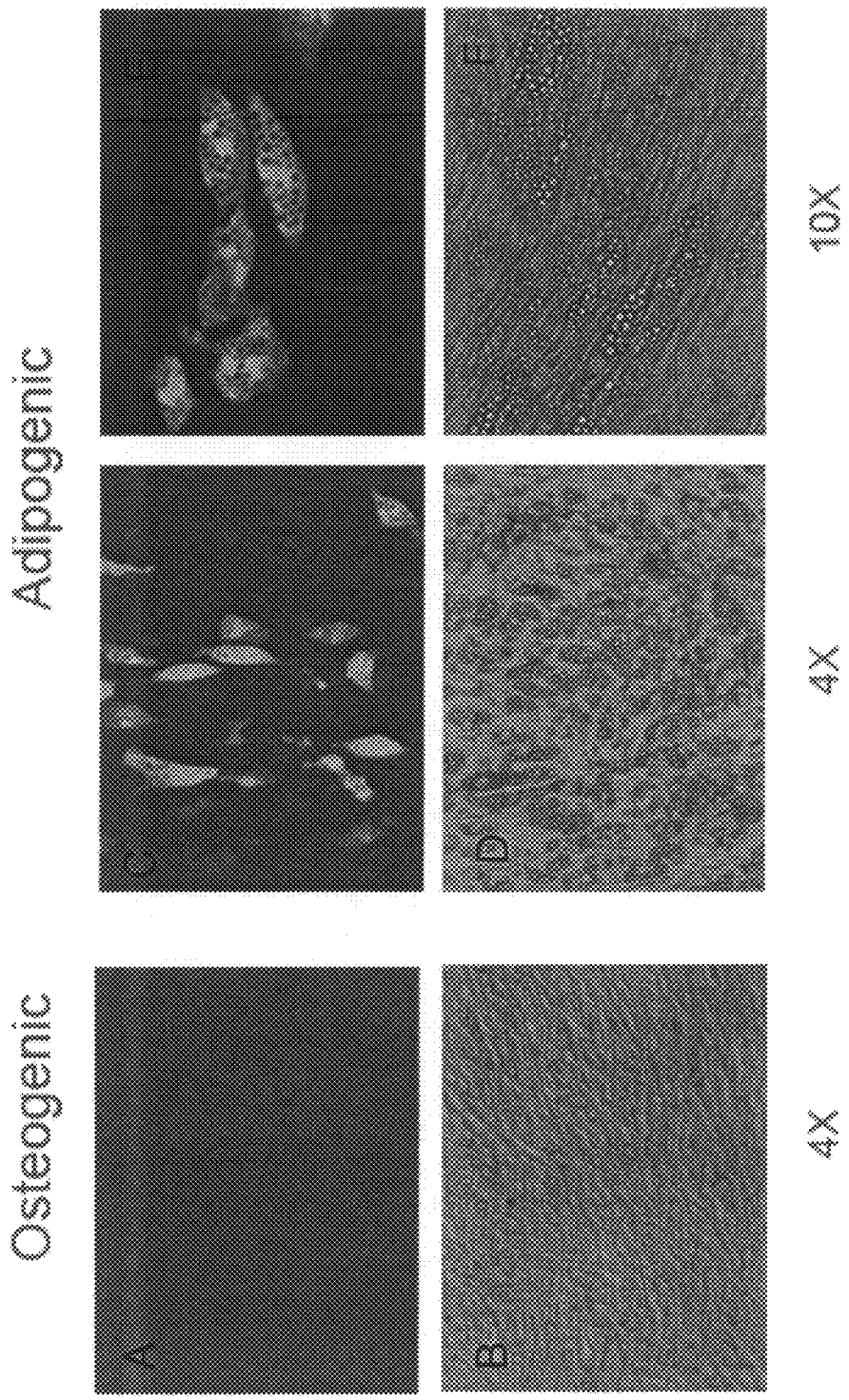
FIG. 3, panels A to F, depict GFP expression in differentiated hMSCs containing ZFN-mediated integration of aP2-GFP cassettes into the CCR5 locus delivered by IDLVs. The hMSCs were differentiated in vitro into osteogenic (FIGS. 3A and 3B) or adipogenic lineages (FIGS. 3C to 3F). Only the adipogenic lineages expressed GFP.
Figure 4:
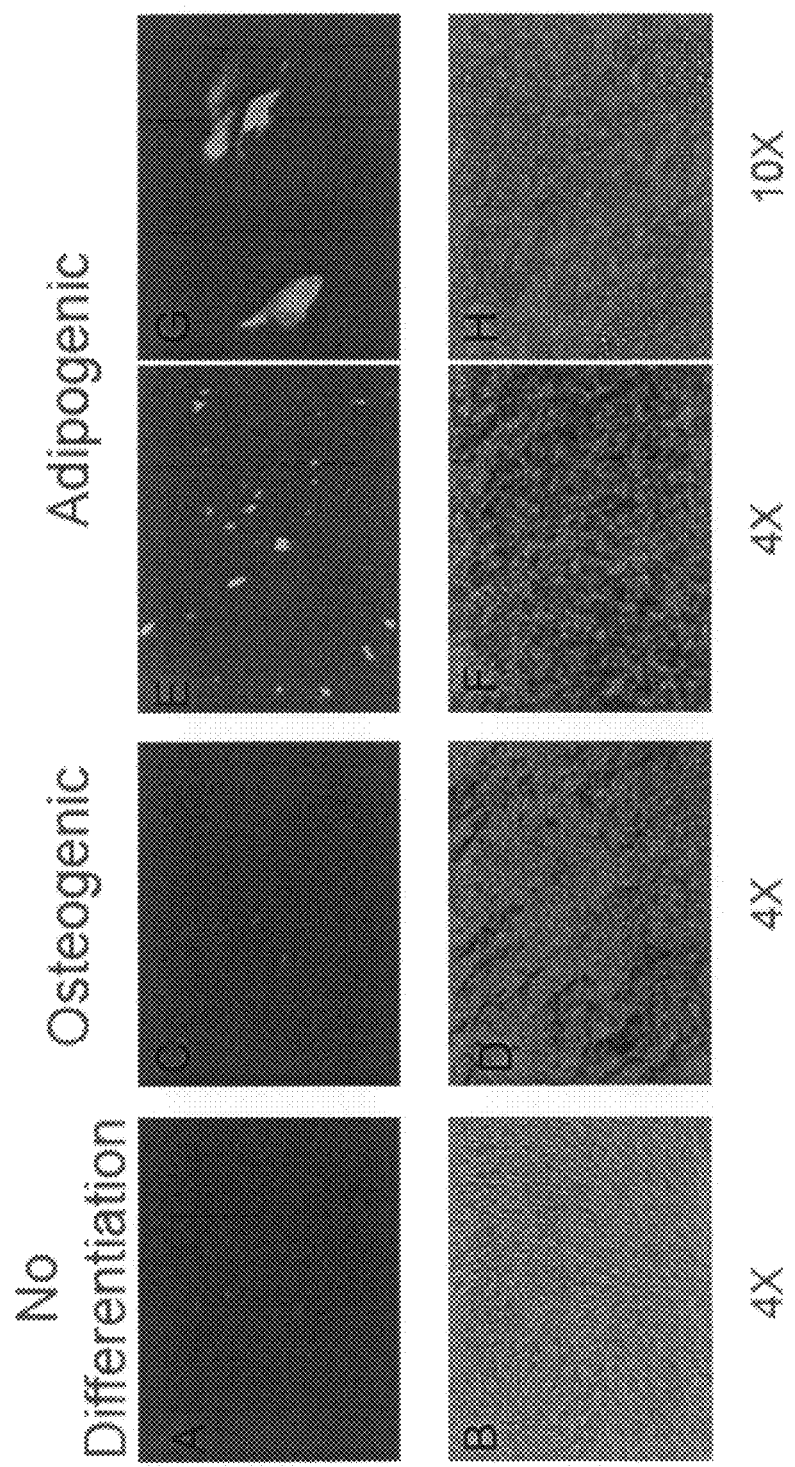
FIG. 4, panels A to H, depict GFP expression in differentiated hMSCs containing a randomly integrated aP2-GFP reporter construct that was introduced into these cells using a standard integrating lentiviral vector. hMSCs that have not been allowed to differentiate (FIGS. 4A and 4B) or those differentiated in vitro into osteogenic (FIGS. 4C and 4D) or adiopogenic lineages (FIGS. 4E to 4H) are depicted. While strong GFP expression is observed in the adipogenic lineages, weak GFP expression is seen in both non-differentiated MSCs and in the osteogenic lineages FIG. 5, panels A to C, are schematics depicting lentiviral donor constructs and targeted insertion of these constructs.

Cells with the integrated reporter constructs were also assayed for GFP expression following in vitro adipocyte or osteocyte differentiation of the hMSCs. In cells containing the integration defective reporter construct, no GFP signal was seen in either the non-differentiated cells or the differentiated osteocytes, while a clear GFP signal was seen in some of the differentiated adipocytes. See, FIG. 3. In cells containing the randomly integrated CCR5 aP2-eGFP donor lentiviral vector, even without differentiation, weak background GFP expression was observed, demonstrating and confirming position dependent leaky expression from a vector when randomly integrated into the genome. See, FIG. 4. A clear GFP signal increase was observed during adipocyte differentiation. This result shows the mouse aP2 promoter specificity in adipocytes, but also shows that the reporter aP2-eGFP expression is affected by genomic positional effects.

To qualify the above results, the undifferentiated cells, and cells that were allowed to undergo adipocyte and osteocyte differentiation were analyzed for GFP expression. For integrating lentiviral vector transduced cells, only an increase on GFP expression level was observed, while there was no increase in the percentage of GFP positive cells during adipocyte differentiation. In contrast, the hMSCs with aP2-eGFP target integrated at the CCR5 locus showed an increase in both the percentage of GFP positive cells, as well as an increase on GFP expression level.

These results show a clear advantage of targeting the insertion of a marker gene over random integration in stem cell lineage-specific reporter labeling.

Example 2: Targeted Integration of an EPO Coding Sequence

Figure 5:
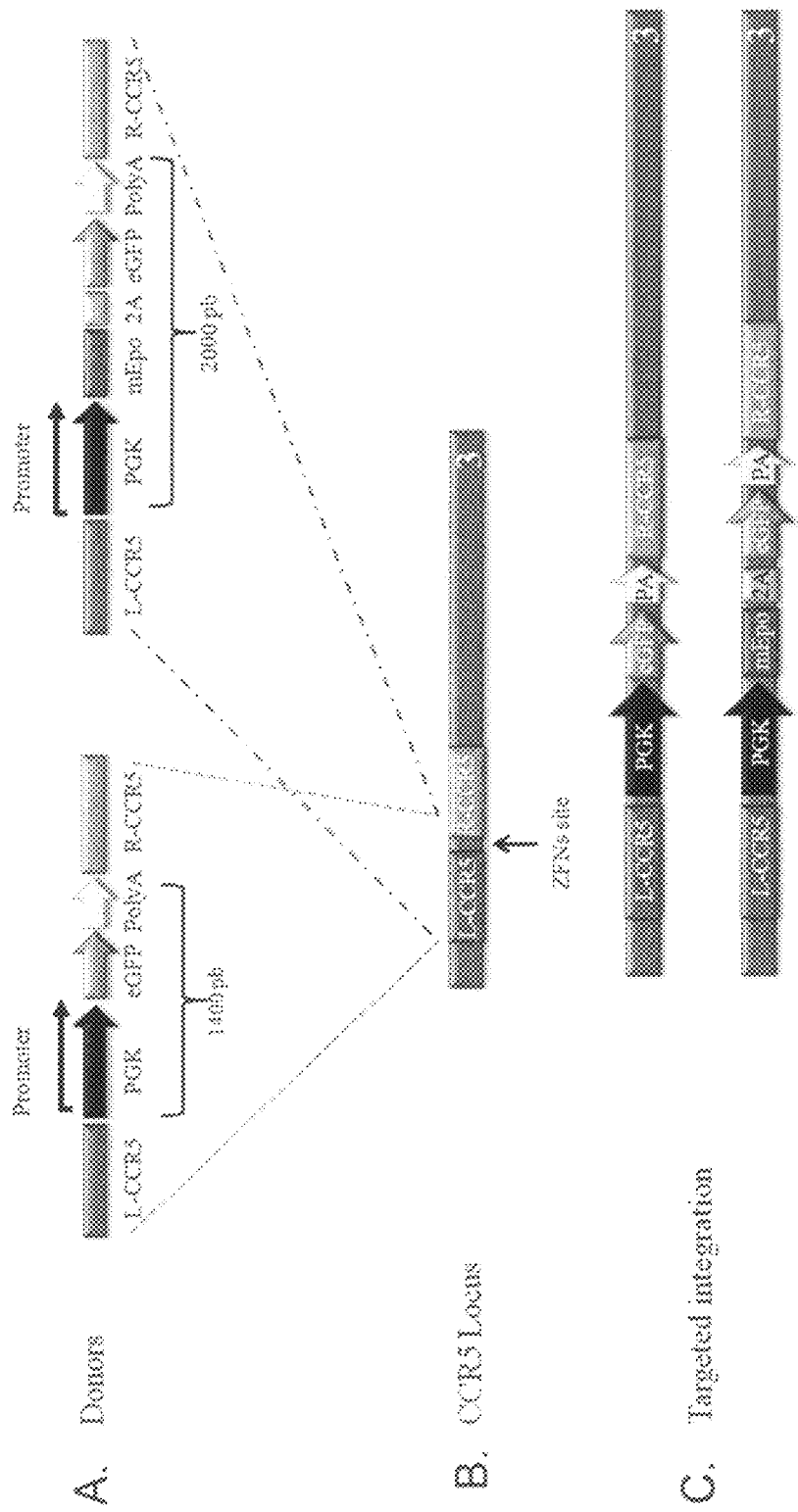
FIG. 5A depicts the eGFP expressing construct designated PGK-eGFP (left side) and the mEpo and eGFP expressing construct designated PGK-mEpo-2A-eGFP (right side).
FIG. 5B is a schematic representation of the position of the ZFN target site(s) within the endogenous CCR5 locus.
FIG. 5C is a schematic representation of the expected result following homologous recombination-mediated targeted gene integration of either PGK-eGFP or PGK-mEpo-2A-eGFP expression cassette.

Lentiviral donor vectors (integrating or non-integrating) were generated containing either a PGK promoter driving expression of eGFP (PGK-eGFP) or EPO and eGFP (PGK-mEpo-2A-eGFP) flanked by sequences homologous to the CCR5 gene. See, FIG. 5A, and U.S. Patent Publication No. 20090117617.

Figure 6:
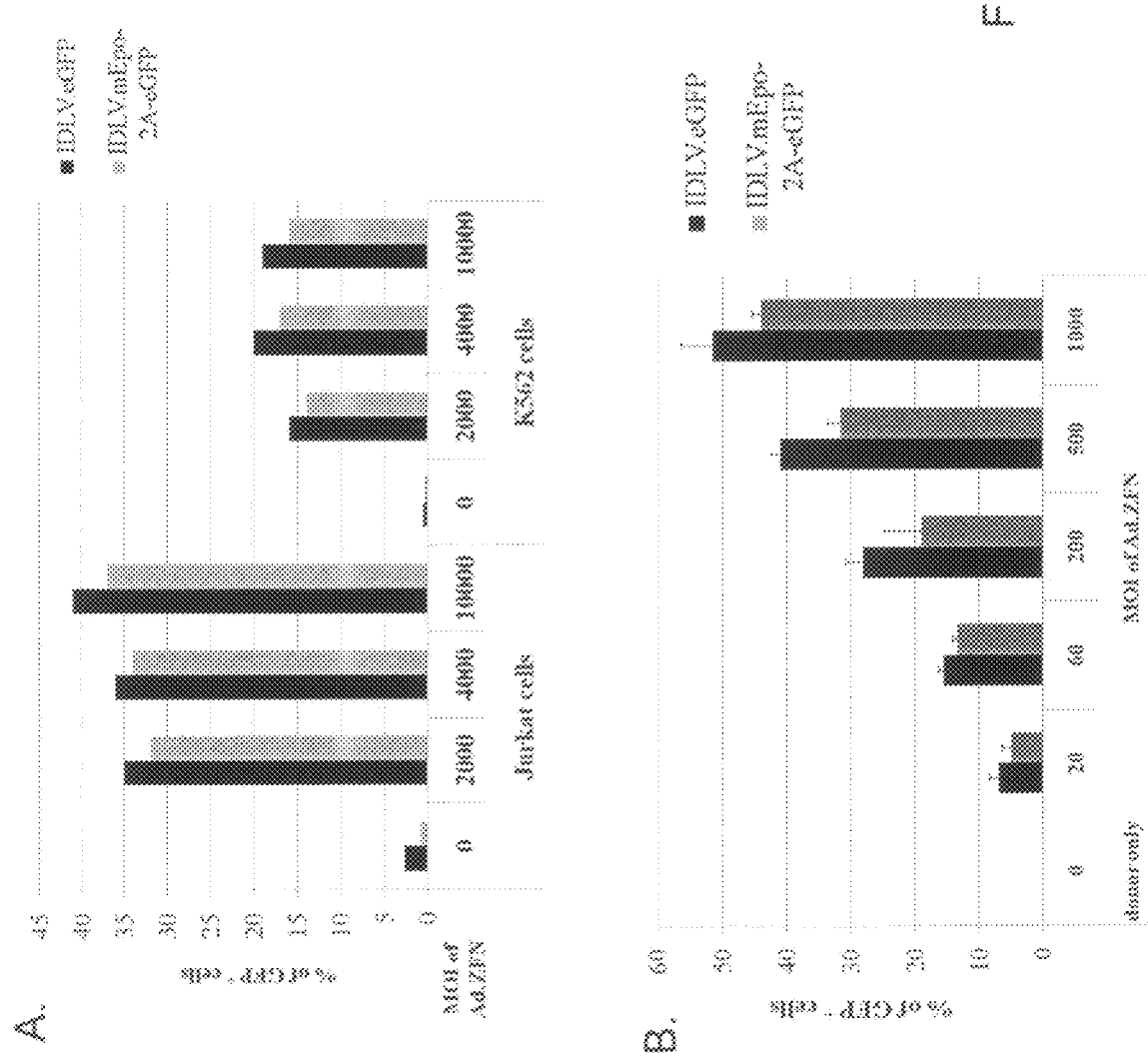
FIG. 6, panels A and B, are graphs depicting the percentage of cells expressing GFP following transduction with the indicated donor vectors at the indicated MOI of Ad.ZFN transduction, as measured by FACS. The black bars depict GFP expression in cells transduced with the IDLV-eGFP construct in the presence of CCR5-targeted ZFNs and the gray bars show GFP expression in cells transduced with the IDLV-mEpo-2A-eGFP construct, also in the presence of CCR5-targeted ZFNs.

Jurkat and K562 human cell lines and human mesenchymal stem cells derived from bone marrow (BM-MSCs) were transduced with IDLV CCR5-targeting donor (PGK-eGFP or PGK-mEpo-2AeGFP cassette) alone or in combination with ZFN-expressing Ad5/F35 at the indicated MOI, and analyzed by FACS for GFP expression 1 month after transduction. See, U.S. Patent Publication No. 20080159996 for a complete description of the CCR5 Ad5/35 ZFNs, which publication is incorporated by reference herein. 75 ng/mL of IDLV was used, as quantitated by a p24 ELISA assay (see for example Cell BioLabs Inc, Lentivirus p24 ELISA kit). As shown in FIG. 6, FACS analysis of Jurkat and K562 human cell lines (FIG. 6A) and human mesenchymal cells (FIG. 6B) showed that over 35% of Jurkat cells, approximately 15% of K562 cells and approximately 15% to 50% of human mesenchymal stem cells (depending on the MOI) expressed GFP following targeted integration of the donor constructs.

Figure 7A:
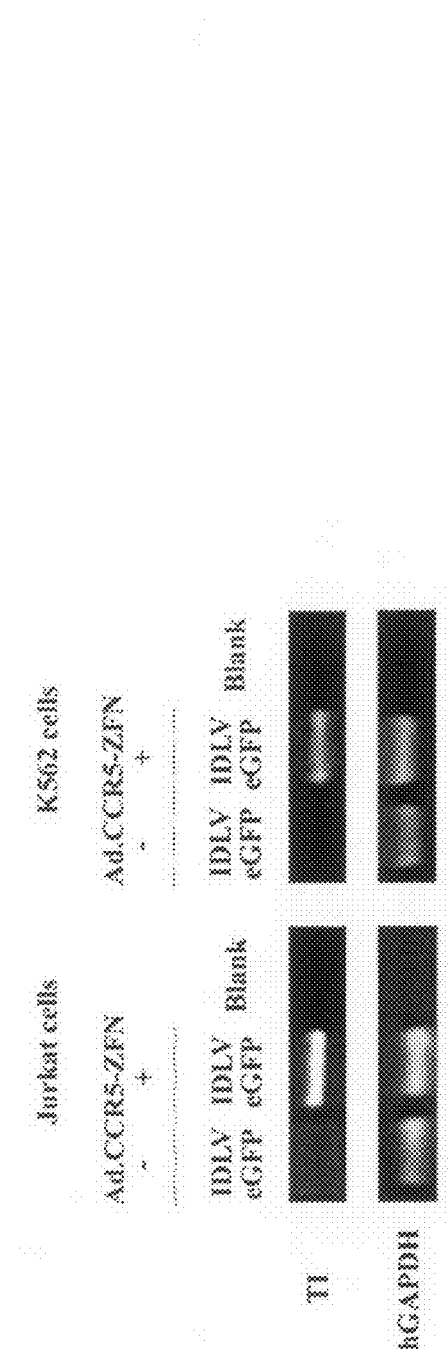
FIG. 7, panels A and B, show PCR analysis for targeted integration of the indicated donor constructs in the absence (lanes labeled Ad.CCR5-ZFN−) and presence of an Ad 5/F35 vector encoding the CCR5-ZFNs (lanes labeled Ad.CCR5-ZFN+) in Jurkat cells (FIG. 7A, left side), K562 cells (FIG. 7A, right side) and hMSCs (FIG. 7B). GAPDH PCR is shown at the bottom of each panel to control for DNA input levels.
Figure 7B:
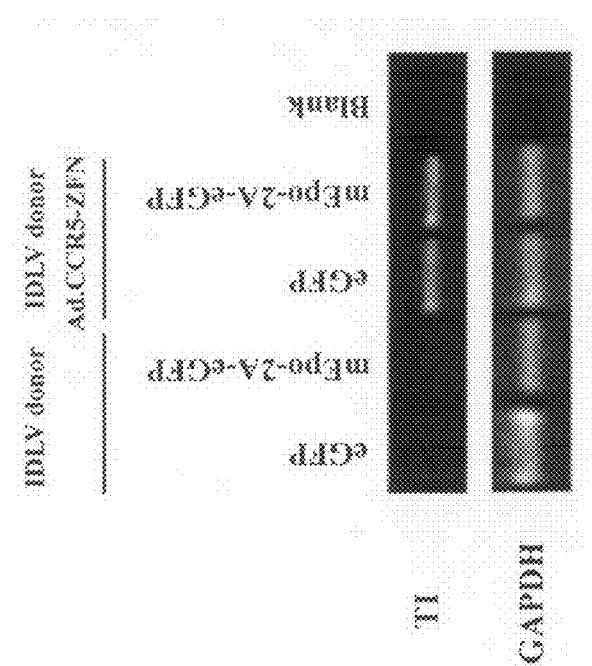

In addition, 1 month post-transduction genomic DNA was isolated from the transduced cells and PCR was performed to detect donor target integration at the CCR5 locus. As shown in FIG. 7, a clear PCR band indicating targeted integration was observed only in the presence of zinc finger nucleases (ZFNs) in Jurkat and K562 cells (FIG. 7A) and human mesenchymal cells (FIG. 7B).

Figure 8:
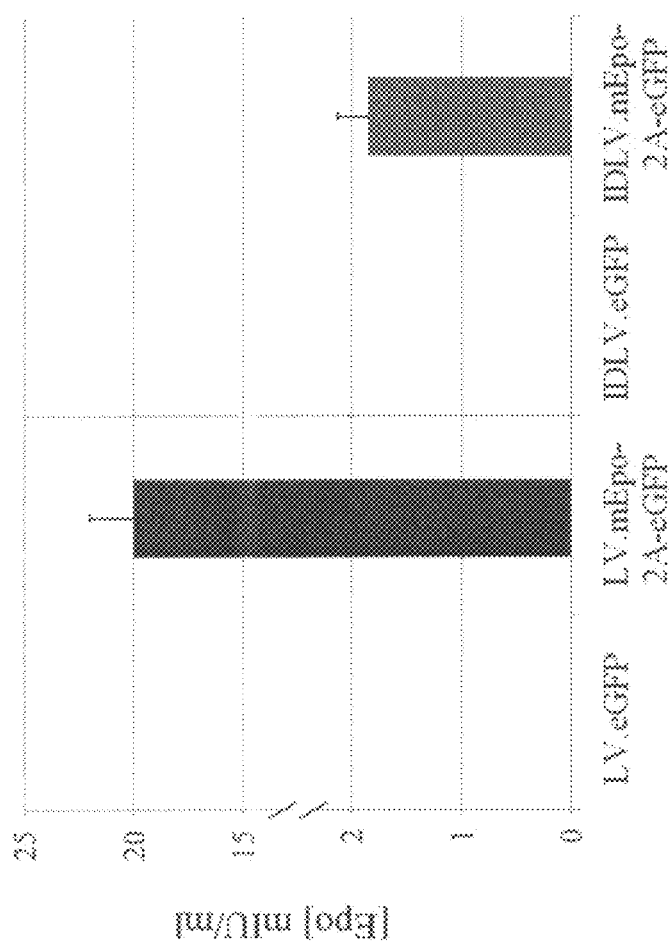
FIG. 8, shows Epo protein expression, as measured by ELISA, in conditioned media of hMSCs transduced with the indicated donor constructs in the presence of an Ad 5/F35 vector encoding the CCR5-ZFNs.

Epo protein concentration in the culture media of the transduced hMSCs was also measured. Briefly, ELISA was performed on 24 hour conditioned media from 100% eGFP positive IDLY donor treated hMSCs 1 month after the transduction with either lentivirus (LV) or with both Ad.ZFN and IDLV donor for eGFP and mEpo-2A-eGFP expression cassettes. As shown in FIG. 8, Epo protein was detected in media from hMSCs transduced with integrating or non-integrating lentiviral donor constructs.

Example 3: In Vivo Activity of ZFN-Modified Stem Cells

Human MSCs expressing mEpo were also administered to mice and effects on hematocrit as well as plasma concentrations of Epo were determined. Briefly, NOD/SCIDγC mice were injected IP either with $10^6$ hMSCs modified with LV-eGFP or LV-mEpo-2A-eGFP, or with $10^7$ hMSCs modified with both Ad.ZFN and IDLV donor (eGFP or mEpo.2A.eGFP expression cassette). The number of MSCs injected was determined following Epo-ELISA where the LV transduced cells showed 10× higher soluble Epo expression than the IDLV transduced cells, perhaps due to an increased number of donor DNAs integrated as compared to the IDLY donor. Peripheral blood was collected from submandibullar vein over a period of 60 days. Hematocrit levels were measured and plasma Epo levels were measured by ELISA.

Figure 9A:
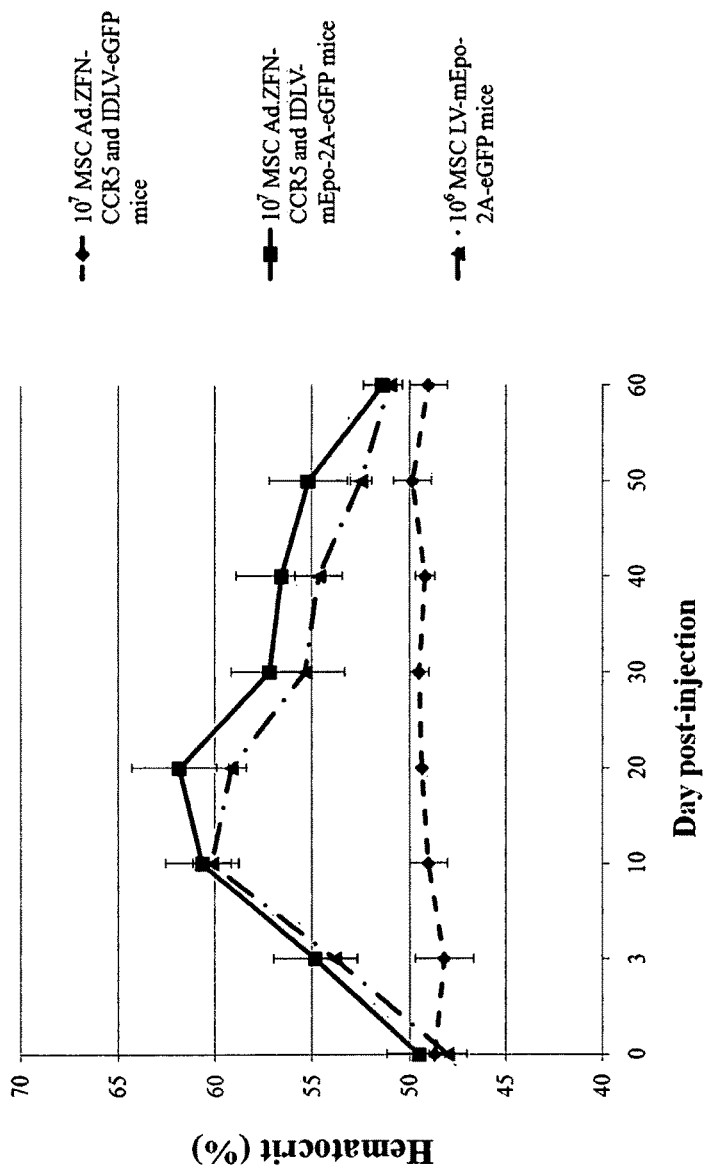
FIG. 9, panels A and B, shows the effect of Epo protein expression on hematocrit (FIG. 9A) and Epo protein levels measured in plasma (FIG. 9B) in mice receiving intraperitoneal (IP) injection of hMSCs with integrated Epo donor constructs. The black diamonds depict Epo protein levels in vivo following administration of $10^7$ hMCSs transduced with an Ad/ZFN-CCR5 construct and the IDLV-eGFP donor construct. The black squares depict Epo protein levels in vivo following administration of $10^7$ hMCSs transduced with an Ad/ZFN-CCR5 construct and the IDLV-mEpo-2A-eGFP donor construct. The black diamonds depict Epo protein in vivo following administration of $10^6$ hMCSs transduced with Ad/ZFN-CCR5 constructs and the integrating LV-mEpo-2A-eGFP donor construct.
Figure 9B:
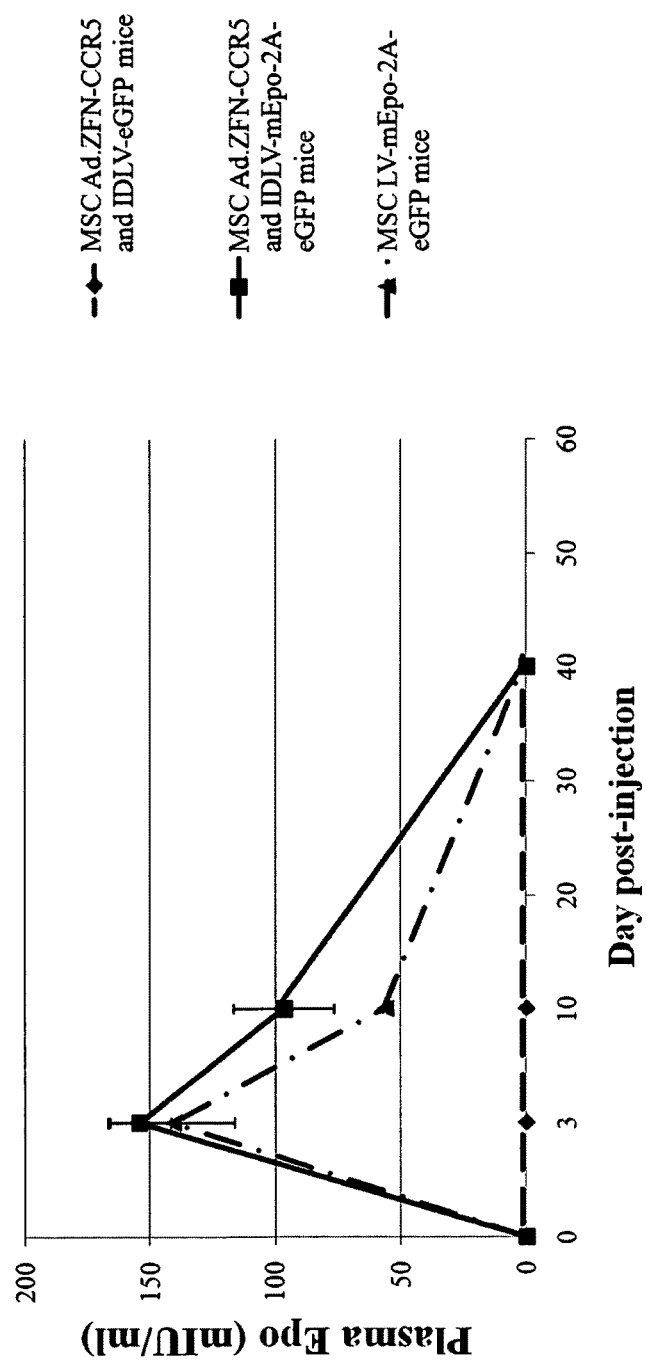

As shown in FIGS. 9A and 9B, hMSCs which had been transduced with IDLV donor constructs gave detectable increases in the levels of Epo protein expression as evidenced in both increases in hematocrit (FIG. 9A) and increases in soluble plasma protein (FIG. 9B).

These results show that a polypeptide coding sequence of interest can be introduced into a stem cell and the polypeptide is expressed in vivo upon administration of the transduced stem cells.

Example 4: Targeted Integration of a Reporter Construct Into the Human OCT4 (POU5F1) Locus To target the human ortholog of the mouse OCT4 gene (also known as POU5F1, herein after referred to as human OCT4) we designed four ZFN pairs (see Table 2 below), which recognize unique sequences in the first intron of the human OCT4 gene (Table 3). ZFNs targeted to human OCT4 were designed and incorporated into plasmids essentially as described in Urnov et al. (2005) *Nature* 435(7042): 646-651, Perez et al (2008) *Nature Biotechnology* 26(7): 808-816, and U.S. Patent Publication 2008/0131962.

TABLE 2

Human OCT 4-specific ZFN recognition helix sequences

| ZFN Name | F1 | F2 | F3 | F4 | F5 | F6 |
|---|---|---|---|---|---|---|
| 16233 (Pair 3, R) | QSGDLTR (SEQ ID NO: 1) | QSSDLRR (SEQ ID NO: 2) | ERGTLAR (SEQ ID NO: 3) | RSDHLTT (SEQ ID NO: 4) | DRSALSR (SEQ ID NO: 5) | RSDNLRE (SEQ ID NO: 6) |
| 16234 (Pair 3, L) | DRSHLSR (SEQ ID NO: 7) | QSGDLTR (SEQ ID NO: 1) | QSGHLSR (SEQ ID NO: 8) | RSANLAR (SEQ ID NO: 9) | RSDNLRE (SEQ ID NO: 6) | N/A |
| 16237 (Pair #1 L) | RSDVLSE (SEQ ID NO: 10) | TSGHLSR (SEQ ID NO: 11) | DRSDLSR (SEQ ID NO: 12) | TSGHLSR (SEQ ID NO: 11) | RSDVLSE (SEQ ID NO: 10) | N/A |
| 16238 (Pair #1, R) | QSSDLSR (SEQ ID NO: 13) | QSADRTK (SEQ ID NO: 14) | RSAHLSR (SEQ ID NO: 15) | QSGDLTR (SEQ ID NO: 1) | RSDNLSE (SEQ ID NO: 16) | RSANLTR (SEQ ID NO: 17) |

TABLE 2-continued

Human OCT 4-specific ZFN recognition helix sequences

| ZFN Name | F1 | F2 | F3 | F4 | F5 | F6 |
|---|---|---|---|---|---|---|
| 16245 | DRSALSR (SEQ ID NO: 5) | RSDALAR (SEQ ID NO: 18) | RSDVLSE (SEQ ID NO: 10) | TSGHLSR (SEQ ID NO: 11) | QSSDLRR (SEQ ID NO: 2) | N/A |
| 16246 | DRSHLSR (SEQ ID NO: 7) | QSGNLAR (SEQ ID NO: 19) | RSDALSA (SEQ ID NO: 20) | NRSDRTR (SEQ ID NO: 21) | N/A | N/A |
| 16247 (Pair #2, L) | NSDHLTN (SEQ ID NO: 22) | DRANLSR (SEQ ID NO: 23) | RSDNLSV (SEQ ID NO: 24) | QNATRIN (SEQ ID NO: 25) | QSGSLTR (SEQ ID NO: 26) | N/A |
| 16248 (Pair #2, R) | RSDHLSA (SEQ ID NO: 27) | DRSNRKT (SEQ ID NO: 28) | RSAALSR (SEQ ID NO: 29) | QSADRTK (SEQ ID NO: 14) | RSANLTR (SEQ ID NO: 17) | N/A |

TABLE 3

Target sites for human OCT 4-specific ZFNs

| ZFN name | Target site |
|---|---|
| 16233 (Pair 2, R) | gcCAGGTCTGGGCAGCTGCAggtgacca (SEQ ID NO: 30) |
| 16234 (Pair 2, L) | ccCAGGAGaGGAGCAGGCagggtcagct (SEQ ID NO: 31) |
| 16237 (Pair #1 L) | tcCTGGGTGCCaGGTCTGggcagctgca (SEQ ID NO: 32) |
| 16238 (Pair #1, R) | agGAGCAGGCAGGGTCAGCTgccctggc (SEQ ID NO: 33) |
| 16245 | aaGCTGGTCTGGTGGCTaggtagatcct (SEQ ID NO: 34) |
| 16246 | ggGCTCTGGAAGGCccacttcagggcct (SEQ ID NO: 35) |
| 16247 (Pair #2, L) | atGTAACAAAGGACTACtcttcccccag (SEQ ID NO: 36) |
| 16248 (Pair #2, R) | atGAGTCAGTGAACAGGgaatgggtgaa (SEQ ID NO: 37) |

To determine the efficiency of the individual ZFN pairs to introduce double-strand breaks (DSBs) at the predicted genomic target location the respective ZFN pairs were transiently expressed in hESCs. Cell culture techniques have been described previously (Soldner et al (2009) Cell 36: 964-977). The hESC line BG01 (NIH Code: BG01; Bresa-Gen, Inc., Athens, Ga.) was maintained on mitomycin C inactivated mouse embryonic fibroblast (MEF) feeder layers in hESC medium [DMEM/F12 (Invitrogen) supplemented with 15% FBS (Hyclone), 5% KnockOut™ Serum Replacement (Invitrogen), 1 mM glutamine (Invitrogen), 1% nonessential amino acids (Invitrogen), 0.1 mM β-mercaptoethanol (Sigma) and 4 ng/ml FGF2 (R&D systems)]. Cultures were passaged every 5 to 7 days either manually or enzymatically with collagenase type IV (Invitrogen; 1.5 mg/ml). The GFP expression cassette was cloned into a FUW-M2rtTA lentiviral vector as described (Hockemeyer et al. (2008) Cell Stem Cell 3:346-353). Briefly, VSVG coated lentiviruses were generated in 293 cells as described previously (Brambrink et al. (2008) Cell Stem Cell 2:151-159). Culture medium was changed 12 hours post-transfection and virus-containing supernatant was collected 60-72 hours post transfection. Viral supernatant was filtered through a 0.45 µm filter. Virus-containing supernatants used to infect hESCs aggregates separated from feeder cells by collagenase treatment and serial washes. Two consecutive infections in the presence of 2 µg/ml of polybrene were performed over a period of 12 hours in suspension. hESC cell aggregates were replated after infection on feeders. Infection efficiencies were determined using FACS analysis for eGFP and SSEA4 of cells cultured in the presence of doxycycline (Sigma-Aldrich; 2 µg/ml) for two days. To enrich for transduced cells, targeted and infected hESCs were FACS sorted as single cell solution for eGFP expressing cells 2 days after doxycycline induction in the presence of ROCK-Inhibitor (FACS-Aria; BD-Biosciences) and subsequently replated in the ROCK-Inhibitor containing ESC medium.

The frequency of ZFN mediated disruption of the target site was analyzed by CEL-I mismatch assays, performed essentially as per the manufacturer's instructions (Trangenomic SURVEYOR™). Three out of four tested ZFN pairs were able to efficiently introduce a DSB at the predicted location in the human OCT4 locus.

Figure 10A:
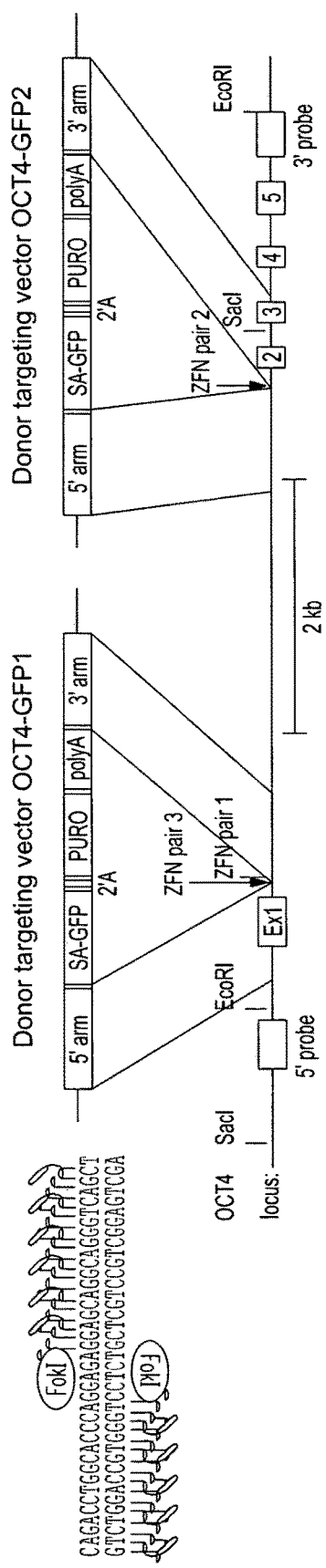
FIG. 10A depicts a schematic overview of the targeting strategy for the OCT4 locus.
Figure 10B:
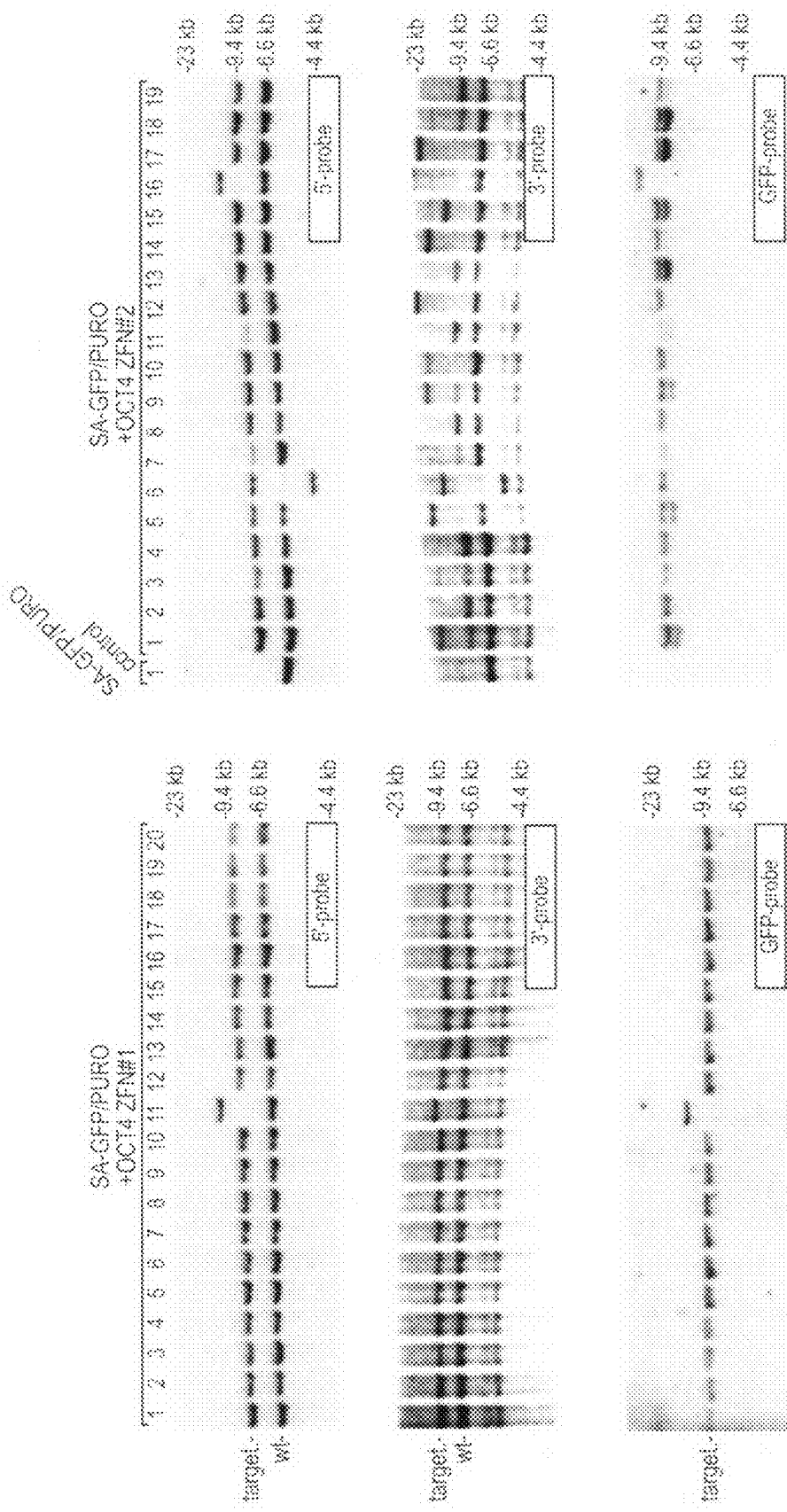
FIG. 10B shows Southern blot analysis of BGO1 cells targeted with the indicated ZFN pairs using the corresponding donor plasmids. Genomic DNA was digested either with EcoRI and hybridized with the external 3'-probes or digested with SacI and hybridized with the external 5'-probe or internal eGFP probe.

Corresponding to these three ZFN pairs we designed donor plasmids, which carried 5' and 3' homology regions covering roughly 700 by of the human OCT4 sequence flanking the DSB target site. These donor plasmids contained a splice acceptor eGFP cassette joined by a 2A self-cleaving peptide sequence to the puromycin resistance gene (puromycin N-acetyl-transferase) followed by a polyadenylation sequence (FIG. 10A). Correct targeting of these donor constructs to the first intron of the human OCT4 locus are predicted to result in the expression of two proteins: a fusion protein comprised of the first 132 aa of human OCT4 fused to eGFP (OCT4EX1-eGFP) and the puromycin N-acetyl-transferase, both under the transcriptional control of the endogenous human OCT4 promoter. Co-electroporation of the donor plasmids with their respective ZFN pairs into $10 \times 10^6$ hESCs (BGO1) resulted in colonies after 14 days of puromycin selection that were expanded to establish independent cells lines. Southern blot analysis was done using genomic DNA that had been separated on a 0.7% agarose gel after restriction digest with the appropriate enzymes, transferred to a nylon membrane (Amersham) and hybridized with 32P random primer (Stratagene) labeled probes. External probes 3' and 5' to the donor homology were used as well as an internal probe against eGFP (see FIG. 10B).

As shown Table 4, isolated and expanded puromycin resistant ZFN-treated clones were typically correctly and efficiently targeted. The results of the experiments shown in Table 4 were all performed in BGO1 cells.

TABLE 4

Results from targeting human OCT4

|  |  |  |  | correct targeted clones | | | |
|---|---|---|---|---|---|---|---|
| ZFN pair | donor | clones picked | # random integration* | targeted + additional integration | hetero- zygous* | homo- zgyous* | Targeting Efficency (%)* |
| control | OCT-GFP #1, 2, 3 | 2/1 | 2/1 | 0 | 0 | 0 | 0 |
| ZFN#1 (2.5 µg) | OCT-GFP #1 | 4/21 | 1 | 0 | 4/20 | 0 | 100/95 |
| ZFN#1 (10 µg) | OCT-GFP #1 | 17 | 1 | 0 | 16 | 0 | 94 |
| ZFN#2 (2.5 µg) | OCT-GFP #2 | 15/24 | 0/9 | 7/4 | 8/11 | 0 | 53/46 |
| ZFN#2 (10 µg) | OCT-GFP #2 | 31 | 1 | 12 | 18 | 0 | 40 |
| ZFN#3 (2.5 µg) | OCT-GFP #3 | 2 | 1 | 0 | 1 | 0 | 50 |
| ZFN#3 (10 µg) | OCT-GFP #3 | 1 | 0 | 1 | 0 | 0 | 0 |

*when two numbers are shown this indicates the results form two independent experiments To verify that the OCT4EX1-eGFP targeted cells maintained a pluripotent state, they were immunostained for the pluripotency markers NANOG, SOX2, Tra-1-60 and SSEA4 known to be characteristic of hESCs. Briefly, cells were fixed in 4% paraformaldehyde in PBS and immunostained according to standard protocols using the following primary antibodies: SSEA4 (mouse monoclonal, Developmental Studies Hybridoma Bank); Tra-1-60, (mouse monoclonal, Chemicon International); hSOX2 (goat polyclonal, R&D Systems); Oct-3/4 (mouse monoclonal, Santa Cruz Biotechnology); hNANOG (goat polyclonal R&D Systems) and appropriate Molecular Probes Alexa Fluor® dye conjugated secondary antibodies (Invitrogen) were used.

Furthermore, when injected into SCID mice, the cells induced teratomas that were able to differentiate into cell types originating from all three developmental germ layers confirming their pluripotent state. hESCs were collected by collagenase treatment (1.5 mg/ml) and separated from feeder cells by subsequent washes with medium and sedimentation by gravity. hESCs aggregates were collected by centrifugation and re-suspended in 250 µl of phosphate buffered saline (PBS). hESCs were injected subcutaneously in the back of SCID mice (Taconic). Tumors generally developed within 4-8 weeks and animals were sacrificed before tumor size exceeded 1.5 cm in diameter. Teratomas were isolated after sacrificing the mice and fixed in formalin. After sectioning, teratomas were diagnosed based on hematoxylin and eosin staining.

Figure 10C:
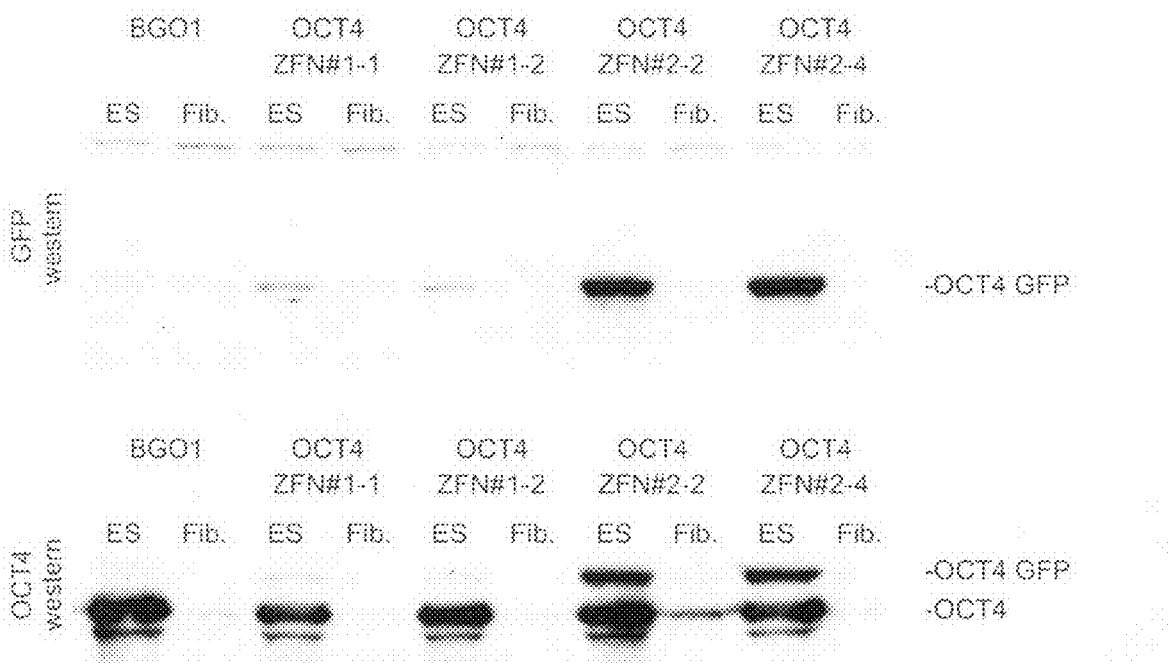
FIG. 10C depicts a Western blot analysis for the expression of OCT4 and eGFP in BGO1 wild type cells and BGO1 cells targeted with the indicated ZFN pairs using the corresponding donor plasmids. Cell extracts were derived from either undifferentiated cells (ES) or in vitro differentiated fibroblast-like cells (Fib.).

In order to functionally validate the correct targeting of the human Oct4 locus in hESCs and the expression of OCT4EX1-GFP under the control of the endogenous promoter, expression of human OCT4 and the predicted OCT4EX1-eGFP fusion protein was confirmed by Western Blot analysis using antibodies against OCT4 and eGFP (FIG. 10C). Briefly, hESCs were collected by collagenase treatment (1.5 mg/ml) and separated from feeder cells by subsequent washes with medium and sedimentation by gravity. hESC derived fibroblasts were collected be trypsinization. Cells pelleted by centrifugation and washed with 1×PBS and again collected by centrifugation. Cells were lysed in ice-cold buffer (50 mM Tris-HCl at pH 7.4, 20% glycerol, 1 mM EDTA, 150 mM NaCl, 0.5% Triton X-100, 0.02% SDS, 1 mM dithiothreitol [DTT], 2 mM phenylmethylsulfonyl fluoride [PMSF]; supplemented with proteinase inhibitor cocktail (Complete Mini, Roche). After 5 min on ice, 5 M NaCl was added to bring the final [NaCl] to 400 mM. After another 5 min on ice, an equal volume of ice-cold water was added and thoroughly mixed before immediate centrifugation in a microfuge (14 krpm, 10 min). Protein concentration of the supernatant was determined by Bradfoard assay and 15 µg of protein was separated using 4-12% Bis-Tris gradient gels (Invitrogen). After transfer to PVDF membranes and probed with OCT4 (mouse monoclonal, Santa Cruz Biotechnology) and GFP (Rbt pAB to GFP Abcam ab290-50) antibodies. ZFN-treated cells expressed OCT4EX1-eGFP protein at varying levels.

Finally, to test whether transgene expression was appropriately regulated, we differentiated targeted hESCs into fibroblasts and found that both OCT4 and OCT4EX1-eGFP proteins were absent in the differentiated cells (FIG. 10C). For EB induced differentiation, hESC colonies were harvested using 1.5 mg/ml collagenase type IV (Invitrogen), separated from the MEF feeder cells by gravity, gently triturated and cultured for 7 days in non-adherent suspension culture dishes (Corning) in DMEM supplemented with 15%. EBs were plated onto adherent tissue culture dishes and passaged according to primary fibroblast protocols using trypsin for at least four passages before the start of experiments. Furthermore, in vitro derived fibroblasts no longer expressed puromycin N-acetyl-transferase as evidenced by their failure to survive in puromycin concentrations as low as 0.5 µg/ml.

These results demonstrate that ZFN mediated gene targeting can be used with high efficiency to generate a reporter system for the pluripotent state of human ES cells.

Example 5: Highly Efficient Targeting of a Safe-Harbor Locus in Human ES Cells

Overexpression studies in hESCs are hampered by the lack of reliable and easy to use expression systems that allow well defined overexpression of transgenes without site-specific clonal variegation and epigenetic silencing effects. The AAVS1 locus on Chromosome 19 represents a previously described and well characterized locus, which has been used to stably express transgenes in multiple transformed and primary cell lines without transgene silencing (Smith et al. (2008) *Stem Cells* 26:496-504). This locus was identified as the viral integration site for adeno-associated viruses (AAVs) thereby disrupting the gene encoding the regulatory subunit 12C of protein phosphatase 1 (PPP1R12C). Furthermore, hESCs targeted in the AAVS1 locus using adeno-associated viral gene delivery techniques showed long-term transgene expression and maintained a pluripotent state (Smith et al., ibid).

In order to establish a robust overexpression system suitable for hESC cultures, we used a ZFN pair to target the first intron of PPP1R12C, which have been previously designed and used to efficiently target transgenes into the AAV locus in multiple transformed human cell lines (see U.S. Publication No: US 20080299580).

We targeted the AAVS1 locus of human ES cells using two different targeting strategies. Because the PPP1R12C gene in the AAVS1 locus is expressed in hESCs, we designed a promoterless donor construct using a splice acceptor-puromycin selection cassette similar to that used to target OCT4 (FIG. 11A). To test whether the high efficiency of ZFN mediated targeting was restricted to using a gene trap approach or could be also achieved by a promoter driven selection cassette we constructed a second AAV donor plasmid that contained a puromycin selection cassette expressed by a human phoshoglycerolkinase (PGK) promoter (FIG. 11A). In parallel experiments we electroporated BGO1 hES cells with the two donor plasmids and ZFNs directed against the AAVS1 locus (fully described in U.S. Patent Application No. 20080299580) and selected for puromycin resistant colonies.

As expected, the promoterless targeting donor plasmid yielded fewer puromycin resistant clones (approximately 50%) than the donor plasmid carrying the PGK-puromycin cassette. Southern blot analysis confirmed that both approaches resulted in correct heterozygous targeting events in the AAV locus (FIG. 11B). In addition, both approaches yielded homozygous targeted clones, in which both AAVS1 alleles showed the correct integration pattern by southern blotting. Quantification of the targeting efficiencies showed that about 50% of the puromycin resistant clones were correctly targeted on one or both alleles (Table 5). Results shown in the first 6 rows of Table 5 show results in BGO1 cells and results shown in the last 3 rows were experiments performed in iPS PD2$^{lox}$-17Puro-5 cells. High targeting efficiency was achieved with both donor plasmids demonstrating that ZFN targeting can be accomplished effectively when using an exogenous promoter driving a selection cassette.

TABLE 5

Targeted integration into the AAVS1 locus of hES cells

| ZFN pair | donor | # clones picked | random integration | targeted + additional integration | hetero-zygous | homo-zgyous | Targeting Efficency (%) |
|---|---|---|---|---|---|---|---|
| control | AAVS1/SA-Puro | 10 | 10 | 0 | 0 | 0 | 0 |
| AAVS1 | AAVS1/SA-Puro | 32 | 2 | 12 | 16 | 2 | 56 |
| control | AAVS1/PGK-Puro | 36 | 36 | 0 | 0 | 0 | 0 |
| AAVS1 | AAVS1/PGK-Puro | 35 | 13 | 5 | 16 | 1 | 49 |
| AAVS1 | AAVS1/TetO-GFP fw | 46 | 5 | 19 | 15 | 7 | 47 |
| AAVS1 | AAVS1/TetO-GFP bw | 35 | 0 | 21 | 10 | 4 | 40 |
| AAVS1 | AAVS1/SA-Puro | 23 | 1 | 8 | 11 | 3 | 61 |
| AAVS1 | AAVS1/PGK-Puro | 15 | 5 | 5 | 5 | 0 | 33 |
| AAVS1 | AAVS1/PGK-Puro | 37 | 9 | 9 | 15 | 4 | 51 |

As with OCT4 targeting discussed in Example 4, a fraction of clones, although targeted, carried additional integrations (Table 5). These were not analyzed further, since the majority of the clones obtained were correctly targeted on one or both ZFN-targeted alleles, and lacked randomly integrated DNA. Importantly, all tested AAVS1-targeted hESCs, including homozygous targeted clones, retained a normal karyotype and a pluripotent state based on immunfluorescence staining for pluripotency markers and teratoma formation assays.

Figure 12:
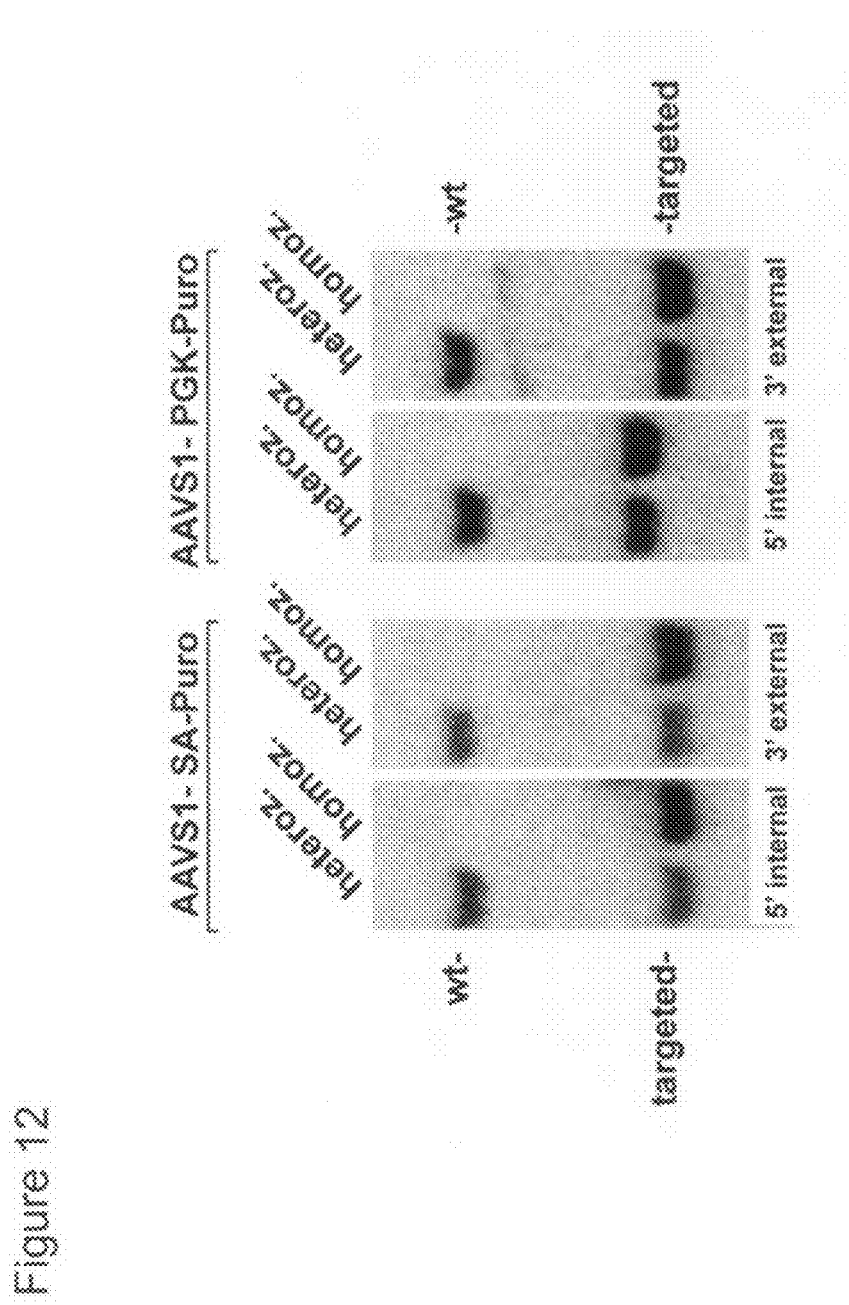
FIG. 12 depicts ZFN mediated gene targeting of the AAVS1 locus in hiPSCs. Southern blot analysis of hiPSC cell line PD21lox17Puro-5 targeted with the indicated ZFN pairs using the corresponding donor plasmids. Genomic DNA was digested with SphI and hybridized with the 32P-labeled external 3' probe or with the internal 5' probe. Fragment size are: PGK-Puro: 5' probe: wt=6.5 kb, targeted=4.2 kb; 3' probe: wt=6.5 kb, targeted=3.7 kb. SA-Puro: 5' probe: wt=6.5 kb, targeted=3.8 kb; 3' probe: wt=6.5 kb, targeted=3.7 kb.

We next addressed whether the ZFN approach could be used to target genes in hiPSCs. For this we targeted the AAVS 1 locus in hiPSC lines previously generated from Parkinson's disease patients (Soldner, F. et al. (2009) Cell 136:964-977) using the same strategies as outlined above for hESCs. As shown in Table 5, ZFN-mediated targeting of hiPSCs using both the splice acceptor and the PGK promoter driven puromycin cassettes resulted in heterozygous and homozygous correctly targeted clones (FIG. 12) with similar efficiency as in hESCs.

Example 6: Expression of Genes Inserted Into the AAVS1 Locus

Figure 13:
FIG. 13 depicts a schematic of a donor nucleotide for a targeting strategy for the PPP1R12C gene in the AAVS1 locus with a donor construct containing a DOX inducible TetO RFP. 2A-GFP is a nucleotide fusion sequence between a nucleotide encoding a self-cleaving 2A peptide fused to GFP. TetO is a tetracycline repressor target ("operator") sequence and it is linked to a minimal CMV promoter, RFP is the nucleotide sequence encoding Red Fluorescent Protein.
Figure 14:
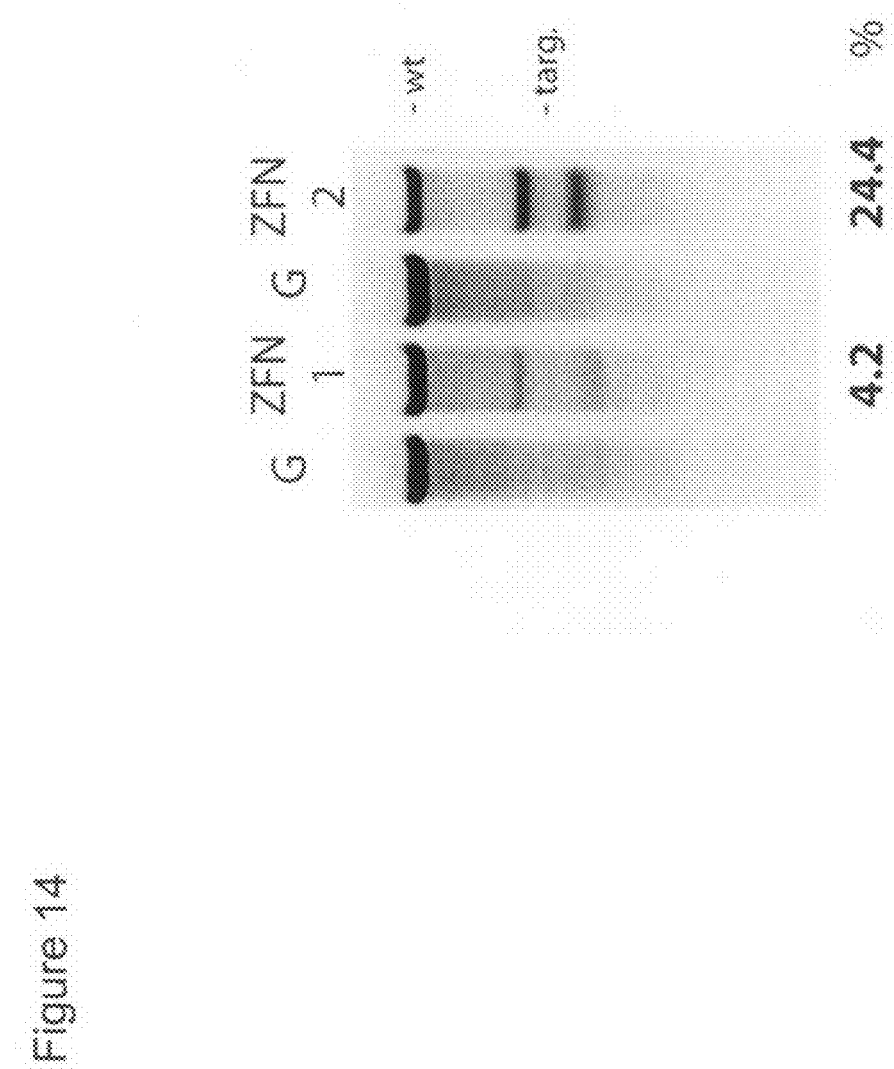
FIG. 14 depicts the results of a PCR analysis for assaying the amount of NHEJ occurring at the PITX3 locus in K562 cells following transfection with two pairs of PITX3-specific ZFNs. The data were generated using a CEL-I mismatch-sensitive endonuclease assay as described (Miller et al. (2007) *Nature Biotechnology* 25(7): 778-85). Percent NHEJ is indicated at the bottom of each lane. 'G' indicates control cells transfected with a GFP expression plasmid.

We are investigating whether the AAVS1 locus can be used to develop an inducible transgenic overexpression system in human ES cells. The previously used promoterless AAVS 1 donor plasmid is redesigned to include an additional expression cassette composed of a minimal CMV promoter and the tetracycline response element driving the Red Fluorescent Protein (RFP) cDNA (TetO-RFP). Included on this donor molecule is a nucleotide sequence encoding the GFP gene linked to a poly-adenylation signal on the 3' end and sequence encoding a self-cleaving 2A peptide on the 5' end (see FIG. 13). In this way, the expression of the GFP is driven by the endogenous promoter and can be used to screen donor positive clones. The donor construct is transfected into K562 cells which serves as a proxy system for hES cells. Correctly targeted K562s are transduced with a lentivirus carrying the M2rtTA reverse transactivator in order to render the cells responsive to DOX. RFP expression is dependent on DOX addition as well as on the presence of M2rtTA.

Example 7: Targeting the PITX3 Locus in Human ESCs and 1PSCs

The observation that an exogenous selection cassette can be used to efficiently target the AAVS1 locus in hESCs and hiPSCs prompted us to explore whether ZFNs could be used to modify genes that are not expressed in hESCs and hiPSCs. To test this we generated two ZFN pairs against the first coding exon of PITX3, a gene encoding a transcription factor that is expressed in differentiated cells such as dopaminergic neurons but not in hESCs. The PITX3 ZFNs and their target sites are shown below in Tables 6 and 7.

TABLE 6

Human PITX3-specific ZFNs (recognition helix sequences)

| ZFN Name | F1 | F2 | F3 | F4 | F5 | F6 |
|---|---|---|---|---|---|---|
| 19255 (pair 1) | RSDHLSR (SEQ ID NO: 39) | QSSDLRR (SEQ ID NO: 2) | QSGHLSR (SEQ ID NO: 8) | RSDALSA (SEQ ID NO: 20) | NRSDRTR (SEQ ID NO: 21) | N/A |
| 19256 (pair 1) | DRSALSR (SEQ ID NO: 5) | QSGHLSR (SEQ ID NO: 8) | DRSDLSR (SEQ ID NO: 12) | RSDHLSA (SEQ ID NO: 27) | QSATRTN (SEQ ID NO: 40) | N/A |
| 19257 (pair 2) | RSDHLSQ (SEQ ID NO: 41) | RSDVRKN (SEQ ID NO: 42) | RSDHLSA (SEQ ID NO: 27) | DRSDLSR (SEQ ID NO: 12) | RSDALSR (SEQ ID NO: 43) | RSDALTQ (SEQ ID NO: 44) |
| 19258 (pair 2) | QSSDLSR (SEQ ID NO: 13) | RNDDRKK (SEQ ID NO: 45) | DRSDLSR (SEQ ID NO: 12) | RSDHLSQ (SEQ ID NO: 41) | QSATRTK (SEQ ID NO: 46) | N/A |

TABLE 7

Target sites for human PITX3-specific ZFNs

| ZFN name | Target Site |
|---|---|
| 19255 (pair 1) | gtGCTCTGGGAGCTGGGggtgcggagtg (SEQ ID NO: 47) |
| 19256 (pair 1) | ctGCAAGGGCCaGGAGCAcagcggtaag (SEQ ID NO: 48) |
| 19257 (pair 2) | gtCTGGGGGCCAGGGTGGGGgcaggtca (SEQ ID NO: 49) |
| 19258 (pair 2) | caGAAAAGGCCTCGGCTtcgctgcccgg (SEQ ID NO: 50) |

Figure 15:
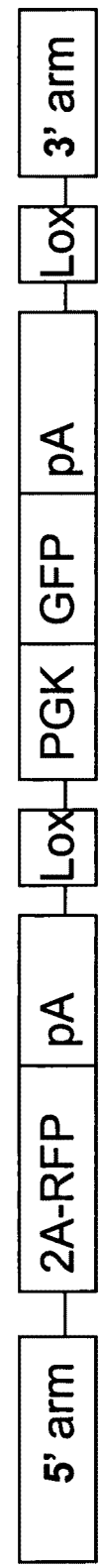
FIG. 15 depicts a schematic of a donor nucleotide for a targeting strategy to generate PITX3-eGFP knock-in cells. 5' arm and 3' arm are homology arms to the endogenous PITX3 locus, 2ARFP-pA indicates an open reading frame comprising a self cleaving 2A peptide linked to a gene encoding Red Fluorescent Protein (RFP) which is linked to a polyA sequence. PGK-GFP-polyA indicates an open reading frame wherein the PGK promoter is linked to the Green Fluorescent Protein (GFP) which is linked to the PGK polyA sequence. lox indicates loxP sites that flank the GFP reading frame.

To generate PITX3-eGFP knock-in cells, donor plasmids are constructed that contain 5' and 3' homologous sequences of approximately 800 by flanking the predicted ZFN target site and include homology to the first coding exon of PITX3. To generate a PITX3 reporter, the PITX3 open reading frame is joined to the reading frame of RFP followed by a polyadenylation signal. The expression of the RFP is thus driven by the PITX3 promoter and associated cis-regulatory elements if they are active. Upstream of the 3' homology arm a PGK-GFP screening cassette is positioned such that it is flanked by loxP sites (FIG. 15). This construct is transfected into hES or hiPSCs as described above.

In order to eliminate the risk of transcriptional interference caused by the PGK-GFP screening cassette, the cassette is subsequently removed by transient expression of the Cre-recombinase. To remove the PGK-GFP screening cassette, cells are harvested using 0.25% trypsin/EDTA solution (Invitrogen) and 1×10$^7$ cells are re-suspended in PBS. They are then electroporated with pTurbo-Cre (40 μg; Genbank Accession Number AF334827) and pEGFP-N1 (10 μg; Clontech) according to manufacturer's instructions (Gene Pulser Xcell System, Bio-Rad: 250 V, 500 μF, 0.4 cm cuvettes). Cre-recombinase expressing cells are enriched by FACS sorting (FACS-Aria; BD-Biosciences) of a single cell suspension for EGFP expressing cells 60 hours after electroporation. Individual colonies are picked 10 to 14 days after electroporation. Using this approach, genes not expressed in hES cells can be targeted and/or modified to generate cell type specific reporter systems.

Example 8: ZFN Targeting of the Factor IX Locus

ZFNs designed to target the Factor IX locus were constructed as described above. The Factor IX-specific ZFNs and their target sites are shown below in Table 8.

To test for the ability to introduce a sequence at a Factor IX locus, a donor plasmid was constructed containing a short (30 bp) tag sequence containing a NheI restriction endonuclease site. The sequence for the 30 bp tag was 5'-gctagc-gatatcgtcgaccatatgggatcc-3' (SEQ ID NO:62). The tag sequence was flanked on both sides by 1000 by regions of homology flanking the ZFN target site in the endogenous gene within intron 1. K562 cells were transfected with a plasmid carrying an expression cassette for the Factor IX-specific ZFNs as well as donor plasmid containing the donor DNA described above. Control experiments were also carried out where donor DNA was used in the absence of the ZFN-expression plasmids; Genomic DNA was extracted at days 3 and 10 and the Factor IX locus was PCR amplified in the presence of radiolabeled dNTPs using primers that hybridize to the region outside the regions homologous to the donor arms. The PCR products were digested with NheI and the products were resolved by a 5% PAGE. The gel was then autoradiographed.

Figure 18:
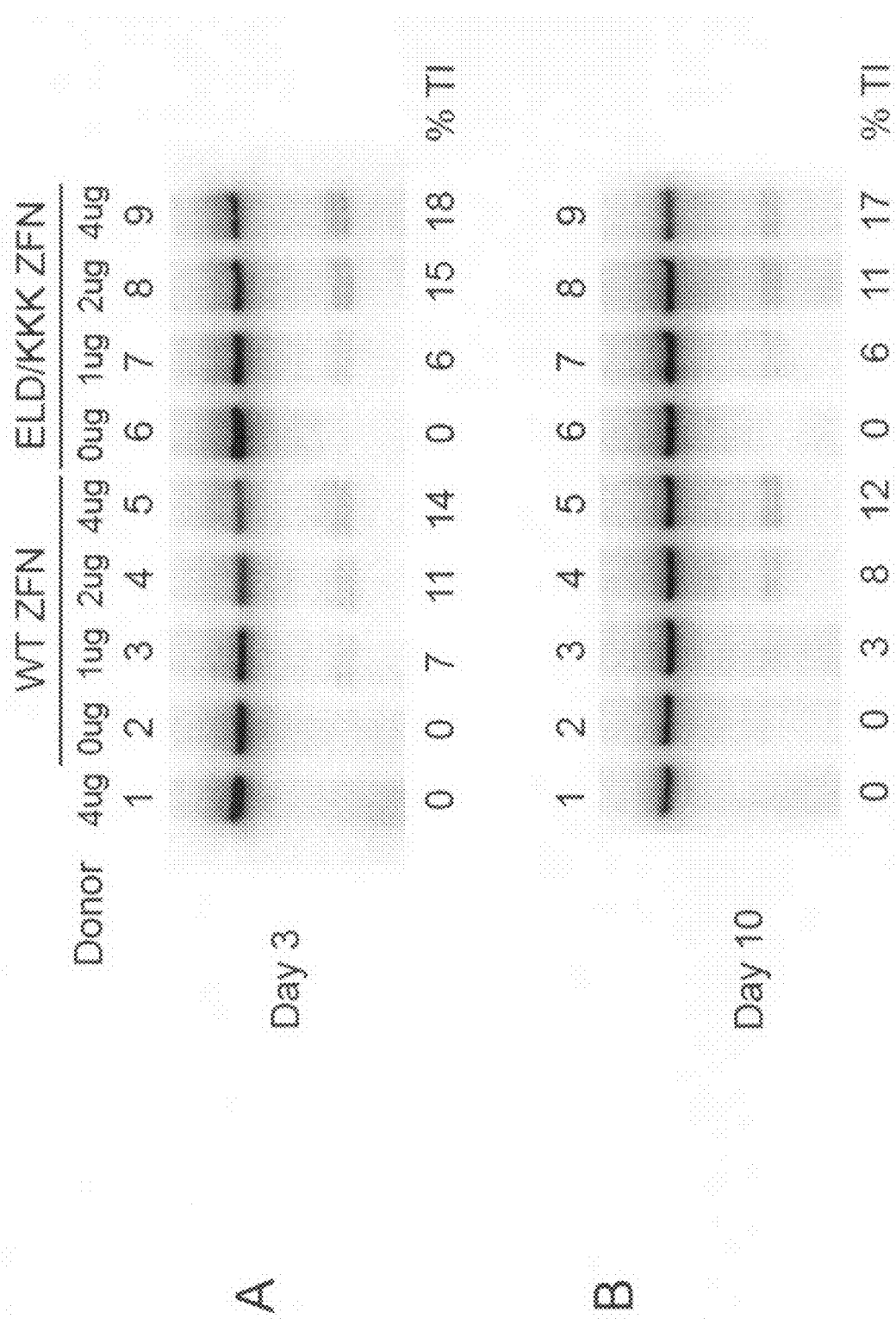
FIG. 18, panels A and B depict the targeted integration of a 30 bp tag containing a restriction endonuclease site into the endogenous Factor IX locus. The figure shows an autoradiograph of a polyacrylamide gel that has resolved products of a NheI digestion of the PCR products of the region containing the integrated tag.

FIG. 18 shows the sensitivity of the repaired DNA to NheI, and demonstrates that ZFN-induced double strand

TABLE 8

Human Factor IX-specific ZFNs

| ZFN Name | F1 | F2 | F3 | F4 | F5 |
|---|---|---|---|---|---|
| SBS#9090 tgACACAGTACCTGgcaccatagttgta (SEQ ID NO: 51) | RSDVLSA (SEQ ID NO: 52) | DRSNRIK (SEQ ID NO: 53) | RSDHLSE (SEQ ID NO: 54) | QSASRKN (SEQ ID NO: 55) | N/A |
| SBS#9022 gtACTAGGGGTATGgggataaaccagac (SEQ ID NO: 56) | RSDLSLV (SEQ ID NO: 57) | TSGHLSR (SEQ ID NO: 11) | RSDHLSQ (SEQ ID NO: 41) | ASSTRIT (SEQ ID NO: 58) | N/A |
| SBS#9802 tgACACAGTACCTGGCAccatagttgta (SEQ ID NO: 51) | QSGDLTR (SEQ ID NO: 1) | RSDVLSE (SEQ ID NO: 10) | DRSNRIK (SEQ ID NO: 53) | RSDNLSE (SEQ ID NO: 16) | QNATRIN (SEQ ID NO: 25) |
| SBS#11004 gtACTAGGGGTATGgggataaaccagac (SEQ ID NO: 56) | RSDSLSV (SEQ ID NO: 57) | TSGHLSR (SEQ ID NO: 11) | RSDHLSQ (SEQ ID NO: 41) | HASTRHC (SEQ ID NO: 59) | N/A |
| SBS#11006 gtACTAGGGGTATGgggataaaccagac (SEQ ID NO: 56) | RSDSLSV (SEQ ID NO: 57) | TSGHLSR (SEQ ID NO: 11) | RSDHLSQ (SEQ ID NO: 41) | HKSTLHA (SEQ ID NO: 60) | N/A |
| SBS#9804 tgACACAGTACCTGGCAccatagttgta (SEQ ID NO: 51) | QSGDLTR (SEQ ID NO: 1) | RSDVLSE (SEQ ID NO: 10) | DNANRTK (SEQ ID NO: 61) | RSDNLSE (SEQ ID NO: 16) | QNATRIN (SEQ ID NO: 25) |

Figure 16:
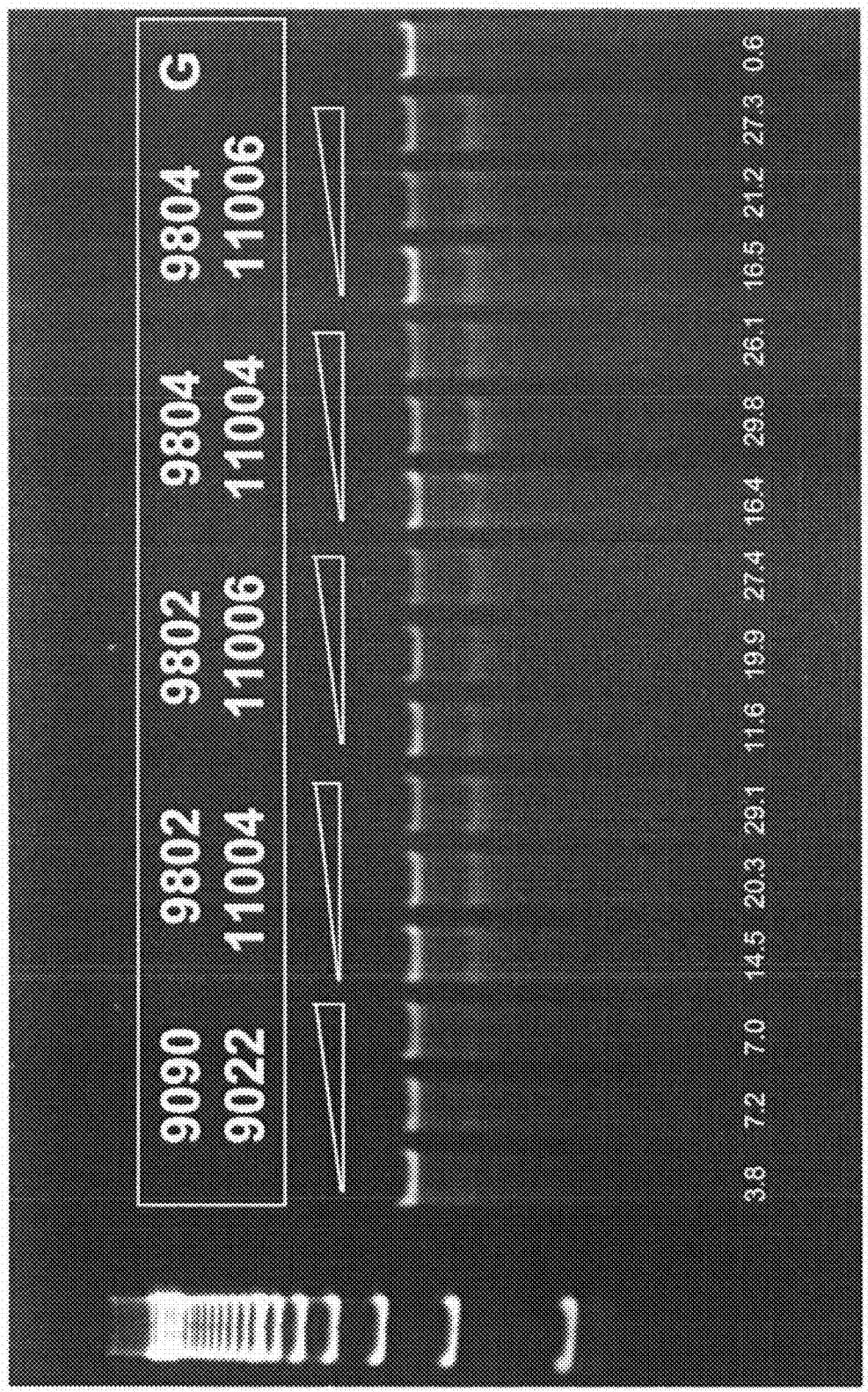
FIG. 16 depicts an agarose gel showing the results of a CEL-I mismatch assay. The gel shows the percent of NHEJ that has occurred in K562 cells following transfection with Factor IX specific ZFNs. Percent NHEJ is indicated at the bottom of each lane. Pairs of ZFNs are indicated above the lanes, and each set shows the results from either 1, 2, or 4 ug of transfecting ZFN-encoding plasmid. 'G' indicates the results following transfection with ZFNs that are specific for GFP.
Figure 17:
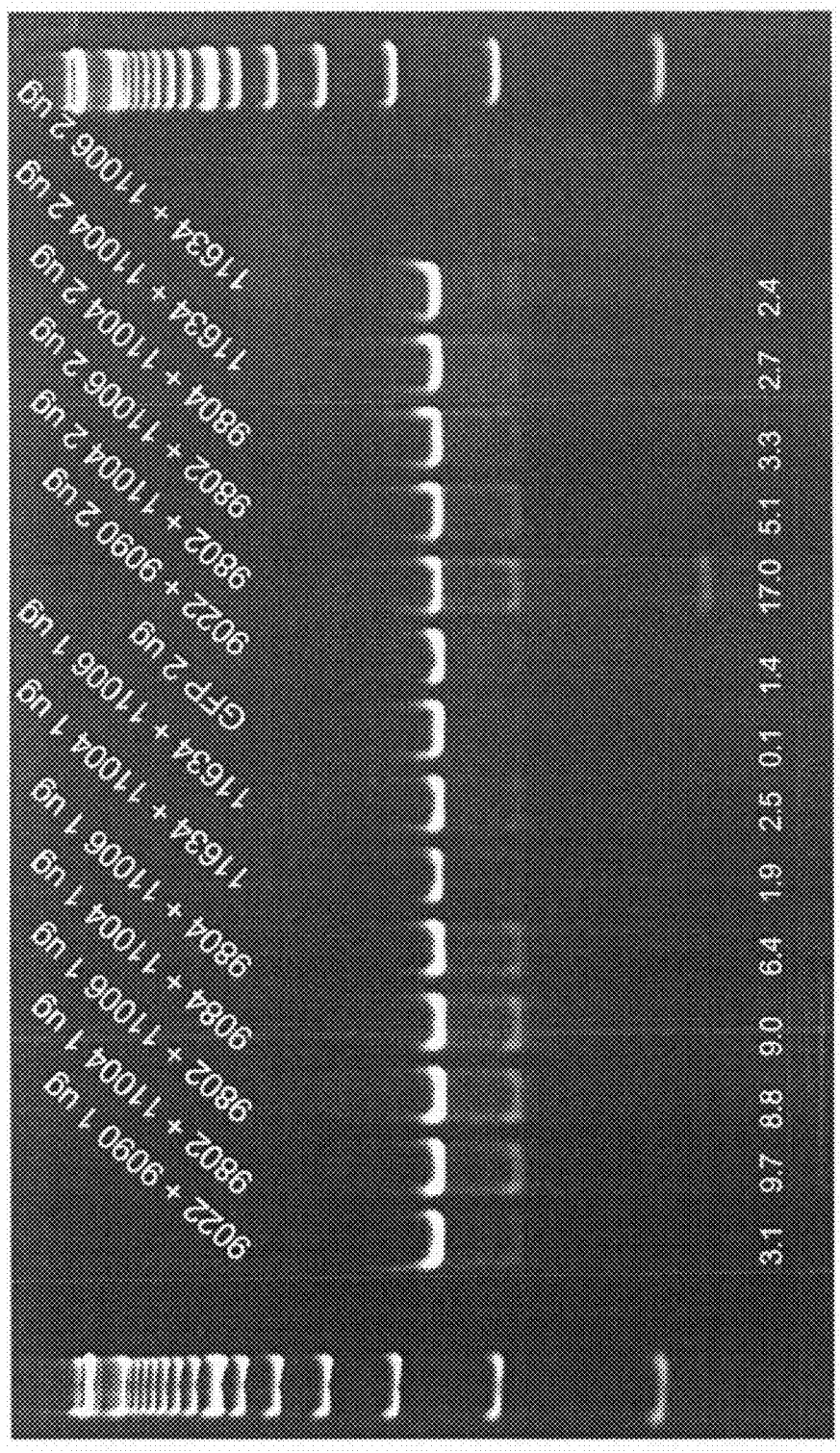
FIG. 17 depicts an agarose gel showing the results of a CEL-I mismatch assay. The gel shows the percent of NHEJ that has occurred in Hep3B cells following transfection with Factor IX specific ZFNs. Percent NHEJ is indicated at the bottom of each lane. Pairs of ZFNs used in each lane are indicated above the lanes, along with the amount of transfecting plasmid used. 'GFP' indicates the results from a control transfection of GFP-specific ZFNs.

ZFN expression plasmids were introduced into either K562 or Hpe3B cells as described above using 1, 2 or 4 μg of ZFN pairs for nucleofection, as is indicated by the increasing triangles shown in FIG. 16 for K562 cells, where the small side of the triangle indicates 1 μg while the large side indicates 4 μg. FIG. 17 shows similar data for Hep3B cells. Three days following nucleofection, cells were harvested and genomic DNA was isolated as described previously.

FIGS. 16 and 17 show that the Factor IX-specific ZFN pairs efficiently induced DSBs at the predicted target site in K562 and Hep3Bcells as analyzed by Surveyor (CEL-I) Nuclease Assay. The percentage of modified alleles as determined by NHEJ is indicated at the bottom of each lane. These results demonstrate that ZFNs specific for human Factor IX can efficiently cleave in both K562 and Hep3B cells.

breaks can lead to efficient, homology-based targeted integration of a desired nucleic acid into the endogenous human Factor IX locus.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated pluripotent or multipotent stem cell comprising a transgene, wherein the transgene is integrated into an endogenous PITX3 or Factor IX gene of the stem cell using a pair of zinc finger nucleases that bind to and cleave the endogenous PITX3 or Factor IX gene, wherein the pair of zinc finger nucleases bind to paired target sites of SEQ ID NO:47 and SEQ ID NO:48 of the PITX3 gene, or paired target sites of SEQ ID NO:49 and SEQ ID NO:50 of the PITX3 gene, or to paired target sites of SEQ ID NO:51 and SEQ ID NO:56 of the Factor IX gene, and further wherein the pair of zinc finger nucleases cleaves the PITX3 or Factor IX gene within or between the paired target sites such that the transgene is integrated into the PITX3 or Factor IX gene.

2. The isolated stem cell of claim 1, wherein the stem cell is selected from the group consisting of a hematopoietic stem cell, a mesenchymal stem cell, an embryonic stem cell, a neuronal stem cell, a muscle stem cell, a liver stem cell, a skin stem cell, and an induced pluripotent stem cell.

3. The isolated stem cell of claim 1, wherein the stem cell is a mammalian stem cell.

4. The isolated stem cell of claim 3, wherein the stem cell is a human induced pluripotent stem cell (hiPSC).

5. The isolated stem cell of claim 1, wherein the transgene is flanked by recombinase sites.

6. The isolated stem cell of claim 1, further comprising a sequence encoding a reporter construct.

7. A stem cell according to claim 1, wherein the isolated transgene comprises a sequence encoding a lineage-specific or cell fate marker as shown in Table 1.

* * * * *